United States Patent
Gordeev et al.

(12)

(10) Patent No.: US 6,441,005 B1
(45) Date of Patent: Aug. 27, 2002

(54) OXAZOLIDINONE COMPOUNDS AND COMPOSITIONS, AND METHODS OF USING THE SAME

(75) Inventors: Mikhail F. Gordeev, Castro Valley; Gary W. Luehr, Hayward; Dinesh V. Patel, Freemont, all of CA (US); Robert C. Gadwood, Portage, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/625,756

(22) Filed: Jul. 26, 2000

Related U.S. Application Data

(60) Provisional application No. 60/146,012, filed on Jul. 28, 1999.

(51) Int. Cl.[7] .................... A61K 31/422; A61K 31/433; C07D 263/04; C07D 401/12; C07D 417/12
(52) U.S. Cl. .................... 514/340; 514/363; 514/364; 514/369; 514/371; 514/376; 544/212; 544/137; 546/271.4; 548/136; 548/143; 548/127; 548/184; 548/195; 548/231; 548/232
(58) Field of Search .................... 544/212; 546/271.4; 548/136, 143, 127, 184, 195, 231, 232; 514/340, 363, 364, 369, 371, 376

(56) References Cited

U.S. PATENT DOCUMENTS

| | | | |
|---|---|---|---|
| 4,705,799 A | 11/1987 | Gregory | 514/376 |
| 4,948,801 A | 8/1990 | Carlson et al. | 514/307 |
| 4,977,173 A | 12/1990 | Brittelli et al. | 514/376 |
| 5,182,403 A | 1/1993 | Brickner | 548/231 |
| 5,225,565 A | 7/1993 | Brickner | 548/229 |
| 5,547,950 A | 8/1996 | Hutchinson et al. | 514/252 |
| 5,684,023 A | 11/1997 | Riedl et al. | 514/337 |
| 5,792,765 A | 8/1998 | Riedl et al. | 514/236.8 |
| 5,827,857 A | 10/1998 | Riedl et al. | 514/301 |
| 5,869,659 A | 2/1999 | Stolle et al. | 544/114 |
| 5,922,708 A | 7/1999 | Riedl et al. | 514/236.8 |
| 5,977,373 A | 11/1999 | Gadwood et al. | 548/128 |
| 6,069,160 A | 5/2000 | Stolle et al. | 514/367 |

FOREIGN PATENT DOCUMENTS

| | | |
|---|---|---|
| DE | 196 01 264 | 7/1997 |
| DE | 196 04 223 | 8/1997 |
| EP | 0 789 026 | 8/1987 |
| EP | 316594 | 5/1989 |
| EP | 359418 | 3/1990 |
| EP | 694544 | 1/1996 |
| EP | 0 738 726 | 10/1996 |
| EP | 738726 | 10/1996 |
| EP | 785200 | 7/1997 |
| EP | 785201 | 7/1997 |
| EP | 789025 | 8/1997 |
| EP | 789026 | 8/1997 |
| JP | 11 322 729 | 11/1999 |
| WO | WO 98/54161 | 12/1998 |
| WO | WO 99/02525 | 1/1999 |
| WO | WO 99/03846 | 1/1999 |
| WO | WO 99/12914 | 3/1999 |
| WO | WO 99/37630 | 7/1999 |
| WO | WO 99/37641 | 7/1999 |
| WO | WO 99/37652 | 7/1999 |
| WO | WO 99/40094 | 8/1999 |
| WO | WO 00/27830 | 5/2000 |
| WO | WO 00/29396 | 5/2000 |
| WO | WO 00/29409 | 5/2000 |

OTHER PUBLICATIONS

Written Opinion in International Application No. PCT/US00/20332, dated May 2, 2001.

W.A. Gregory et al., "Antibacterials. Synthesis and Structure–Activities Studies of 3–aryl–2–oxooxazolidines", J. of Med. Chem., vol. 32, No. 8, pp. 1673–1681 (Aug. 1989).

International Search Report in International Application No. PCT/US00/20332, dated Nov. 16, 2000.

Chia–Lin J. Wang et al., "Chiral Synthesis of Dup 721, A New Antibacterial Agent," *Tetrahedron*, vol. 45, No. 5, pp. 1323–1326 (1989).

Charles Z. Ding et al., "Transformation of Heterocyclic Reversible Monamine Oxidase–B Inactivators into Irreversible Inactivators by N–Methylation," *J. Med. Chem.*, vol. 36, pp. 3606–3610 (1993).

J. Lizondo et al., "Linezolid," *Drugs of the Future*, vol. 21, No. 11, pp 1116–1123 (1996).

Scott E. Schauss et al., "Dynamic Kinetic Resolution of Epichlorohydrin via Enantioselective Catalytic Ring Opening With $TMSN_3$: Practical Syntehesis of Aryl Oxazolidinone Antibacterial Agents," *Tetrahedron Letters*, vol. 37, No. 44, pp. 7937–7940 (1996).

Cecilia Anaya de Parrodi et al., "Preparation of Enantiomerically Pure cis–and trans–N–(propionyl)hexahydrobenzoxazolidin–2–ones," *Tetrahedron: Asymmetry*, vol. 8, No. 7, pp. 1075–1082 (1997).

*Primary Examiner*—Fiona T. Powers
(74) *Attorney, Agent, or Firm*—Marshall, Gerstein & Borun

(57) ABSTRACT

Oxazolidinones and methods for their synthesis are provided. Further provided are methods of making biologically active oxazolidinones as well as pharmaceutically acceptable compositions comprising the oxazolidinones. Oxazolidinones as disclosed herein can be readily synthesized and used in a variety of applications including use as antimicrobial agents. In one embodiment, a variety of thioamidomethyloxazolidinones and methods for their synthesis and use are provided.

60 Claims, 6 Drawing Sheets

OXAZOLIDINONE COMPOUNDS AND COMPOSITIONS, AND METHODS OF USING THE SAME

CROSS-REFERENCE TO RELATED APPLICATIONS

This application claims the benefit of provisional U.S. patent application Serial No. 60/146,012, filed Jul. 28, 1999.

FIELD OF THE INVENTION

The present invention is directed to oxazolidinones, oxazolidinone compositions, and methods for their preparation and use.

BACKGROUND ART

Oxazolidinones are compounds where an amine group and a hydroxyl group on adjacent carbon atoms have been cyclized to form a 5-membered ring containing a carbonyl group. Certain oxazolidinones have been shown to exhibit a variety of biological activities. For example, some oxazolidinones are inhibitors of monoamine oxidase-B, an enzyme implicated in Parkinson's disease. See, for example, Ding et al., *J. Med. Chem.* 36:3606–3610 (1993).

Scientists have reported that certain oxazolidinone derivatives exhibit beneficial antibacterial effects. For instance, N-[3-[3-fluoro-4-(morpholin-4-yl)phenyl]2-oxooxazolidin-5(s)-ylmethyl]acetamide (below) has been reported to be useful for the treatment of bacterial infections. Lizondo et al., *Drugs of the Future*, 21:1116–1123 (1996).

A ten step synthesis of oxazolidinone antibiotics has been described. U.S. Pat. No. 5,547,950. A four step synthesis of the antibacterial compound U-100592 also has been reported. Schauss et al., *Tetrahedron Letters*, 37:7937–7940 (1996). A five step preparation of enantiomerically pure cis- and trans-N-(propionyl)hexahydrobenzoxazolidin-2-ones further was reported. De Parrodi et al., *Tetrahedron: Asymmetry*, 8:1075–1082 (1997).

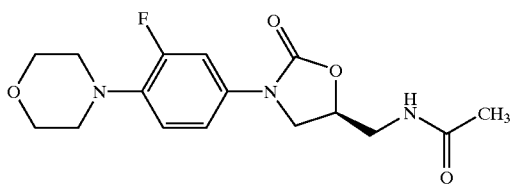

The synthesis of the oxazolidinone antibacterial agent shown below has been reported. Wang et al., *Tetrahedron*, 45:1323–1326 (1989). This oxazolidinone was made using a process that included the reaction of an aniline with glycidol to provide an amino alcohol, and the diethylcarbonate mediated cyclization of the amino alcohol to afford an oxazolidinone.

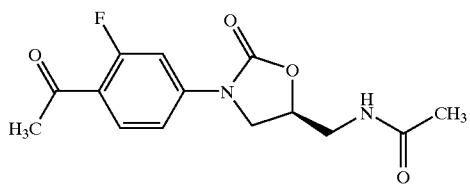

The synthesis of oxazolidinone antibacterial agents, including the compound shown below has been reported. U.S. Pat. No. 4,705,799. The process used to make the compound shown below included a metal mediated reduction of a sulfonyl chloride to provide a sulfide.

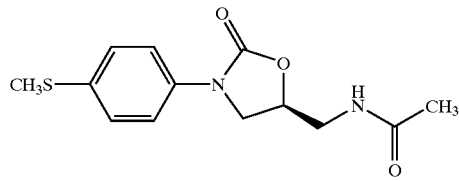

The synthesis of oxazolidinone antibacterial agents, including the pyridyl compound shown below has been reported. U.S. Pat. No. 4,948,801. The process used included an organometallic mediated coupling of an organotin compound and an aryl iodide.

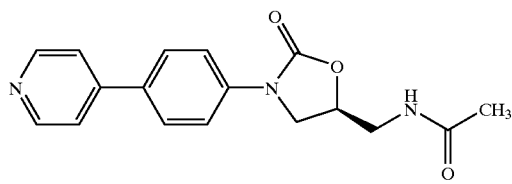

Other reports of syntheses of oxazolidinone compounds are described in DE 196 01 264 A1, EP 0 789 026 A1, DE 196 04 223 A1, EP 0 738 726 A1, and PCT WO 98/54161.

The synthesis of oxazolidinone compounds also is described in U.S. patent application Ser. No. 09/012,535, filed Jan. 23, 1998, U.S. patent application Ser. No. 09/086,702, filed May 28, 1998, U.S. patent application Ser. No. 09/235,771, filed Jan. 22, 1999, and PCT/US99/01318, filed Jan. 22, 1999, the disclosures of which are incorporated herein by reference in their entirety.

SUMMARY OF INVENTION

Provided are oxazolidinones, compositions comprising oxazolidinones, as well as methods of their synthesis and use. Also provided are compositions for the treatment or prevention of an infectious disorder comprising an effective amount of any oxazolidinone compound disclosed herein and a pharmaceutically acceptable carrier. Methods are provided of treating or preventing an infectious disorder in a human or other animal subject, comprising administering to the subject an effective amount of any oxazolidinone compound disclosed herein.

DETAILED DESCRIPTION

Definitions

Figure 1:
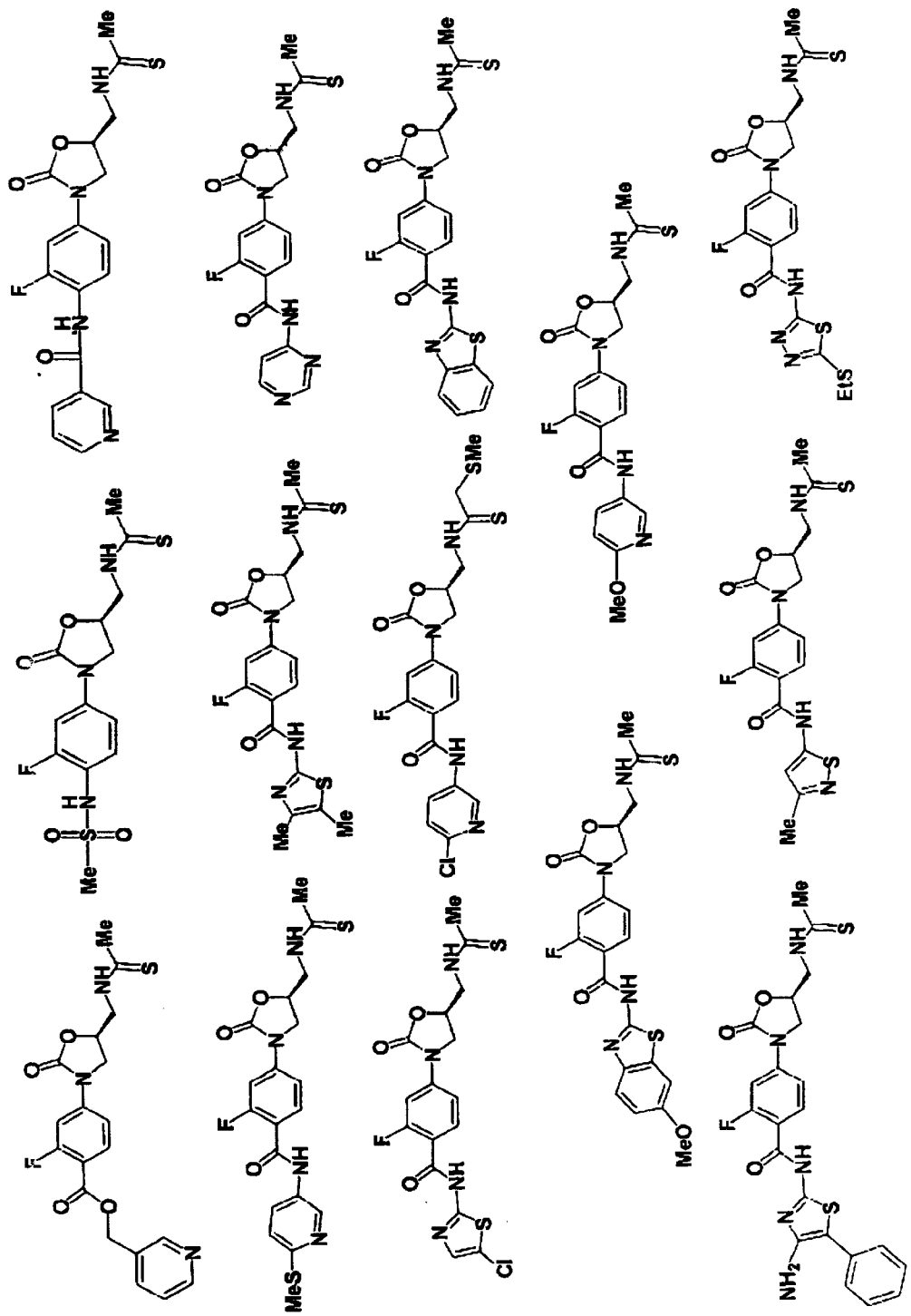
FIG. 1 shows the structure of some exemplary thiocarbonyl oxazolidinone compounds.
Figure 2:
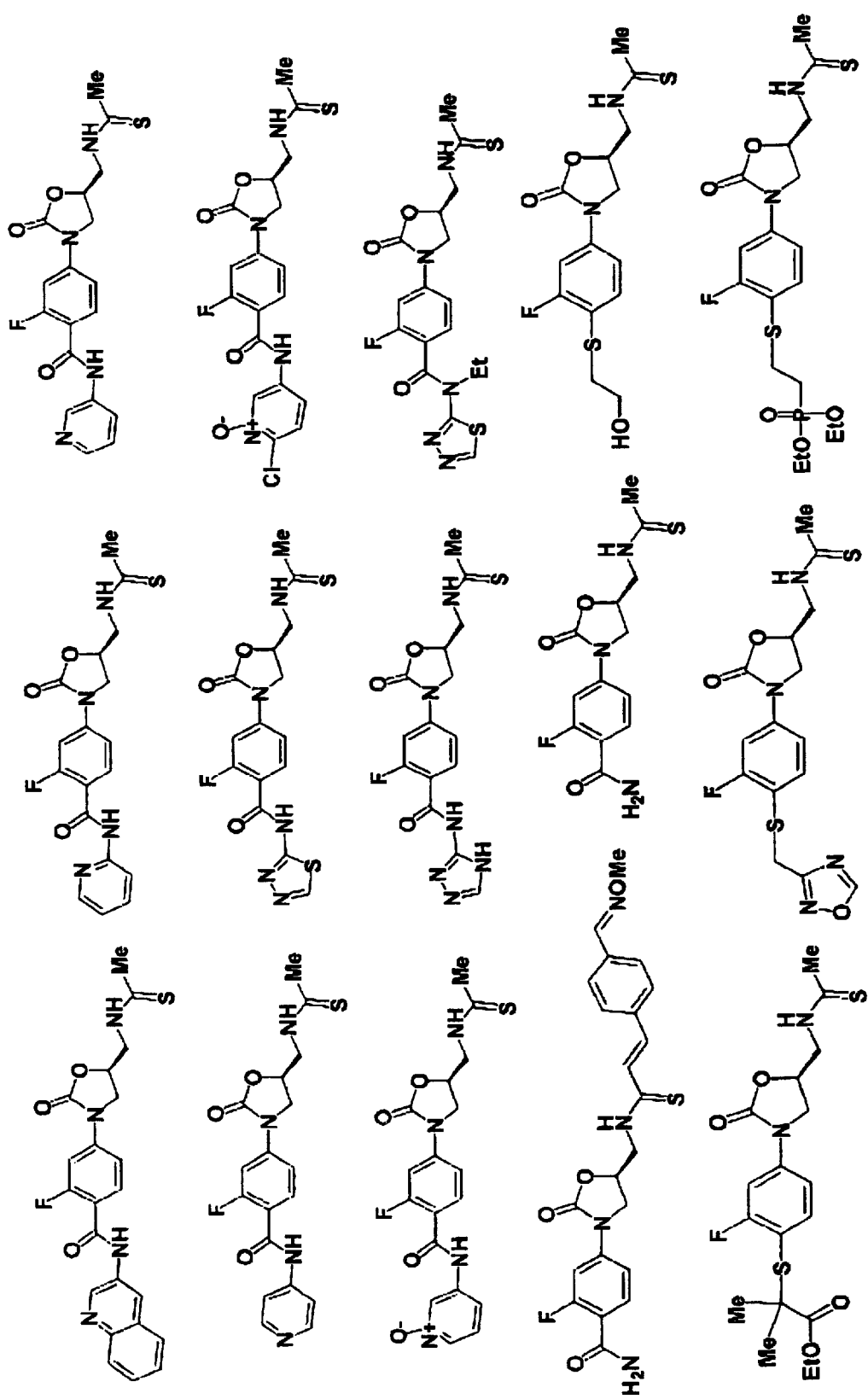
FIG. 2 shows another embodiment of structures of some exemplary thiocarbonyl oxazolidinone compounds.
Figure 3:
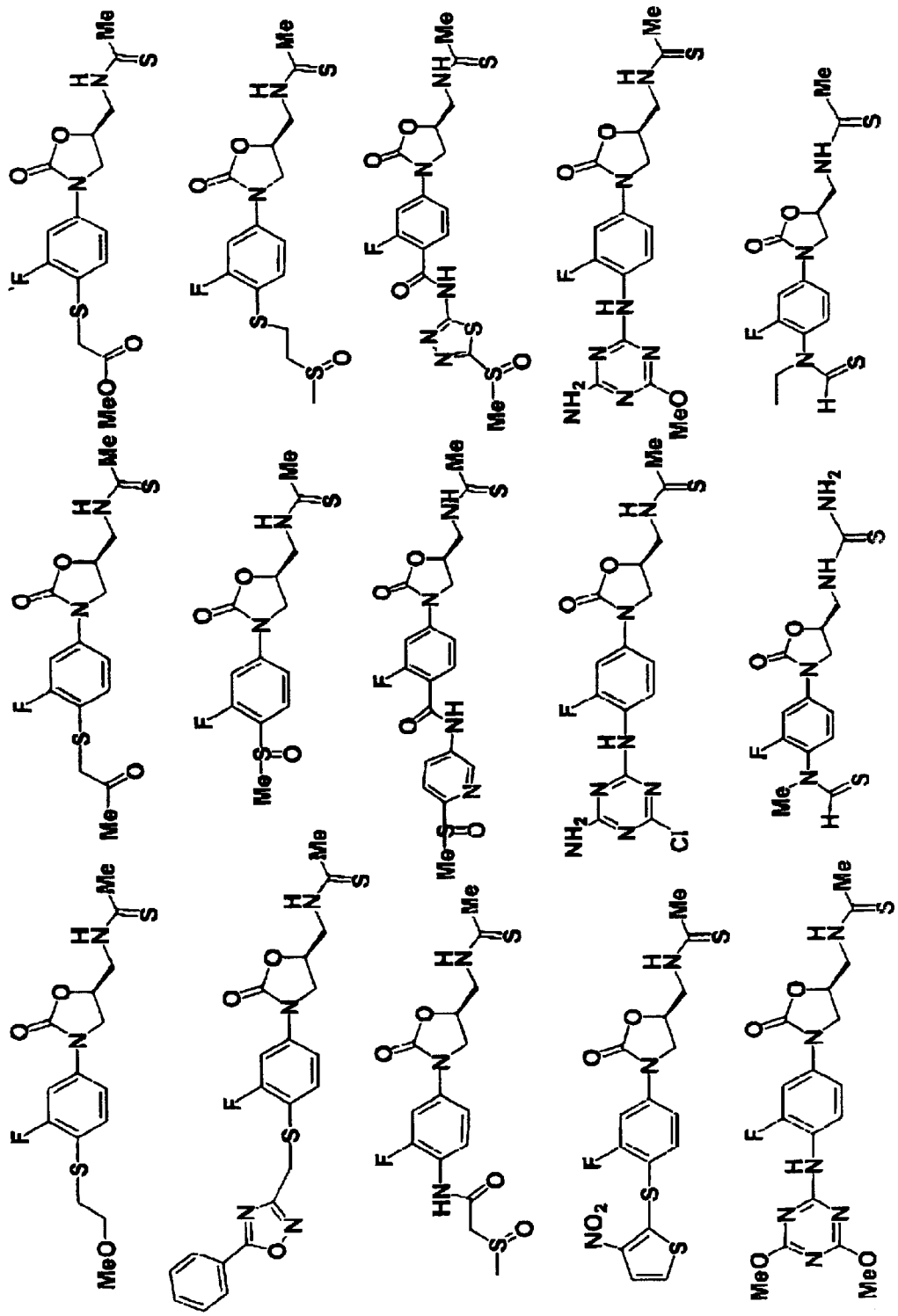
FIG. 3 shows further embodiments of the structure of some exemplary thiocarbonyl oxazolidinone compounds.
Figure 4:
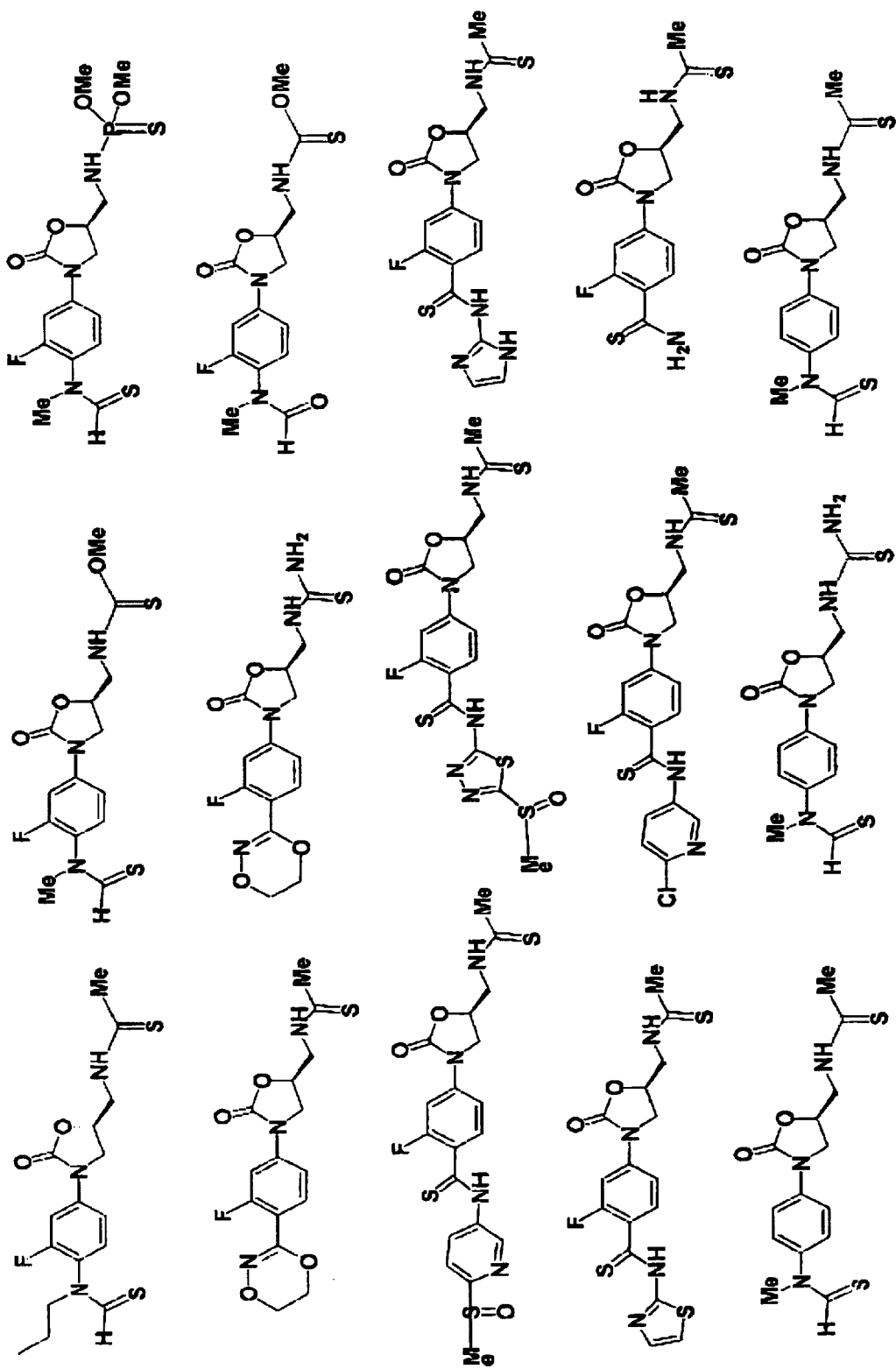
FIG. 4 shows further embodiments of the structure of some exemplary thiocarbonyl oxazolidinone compounds.
Figure 5:
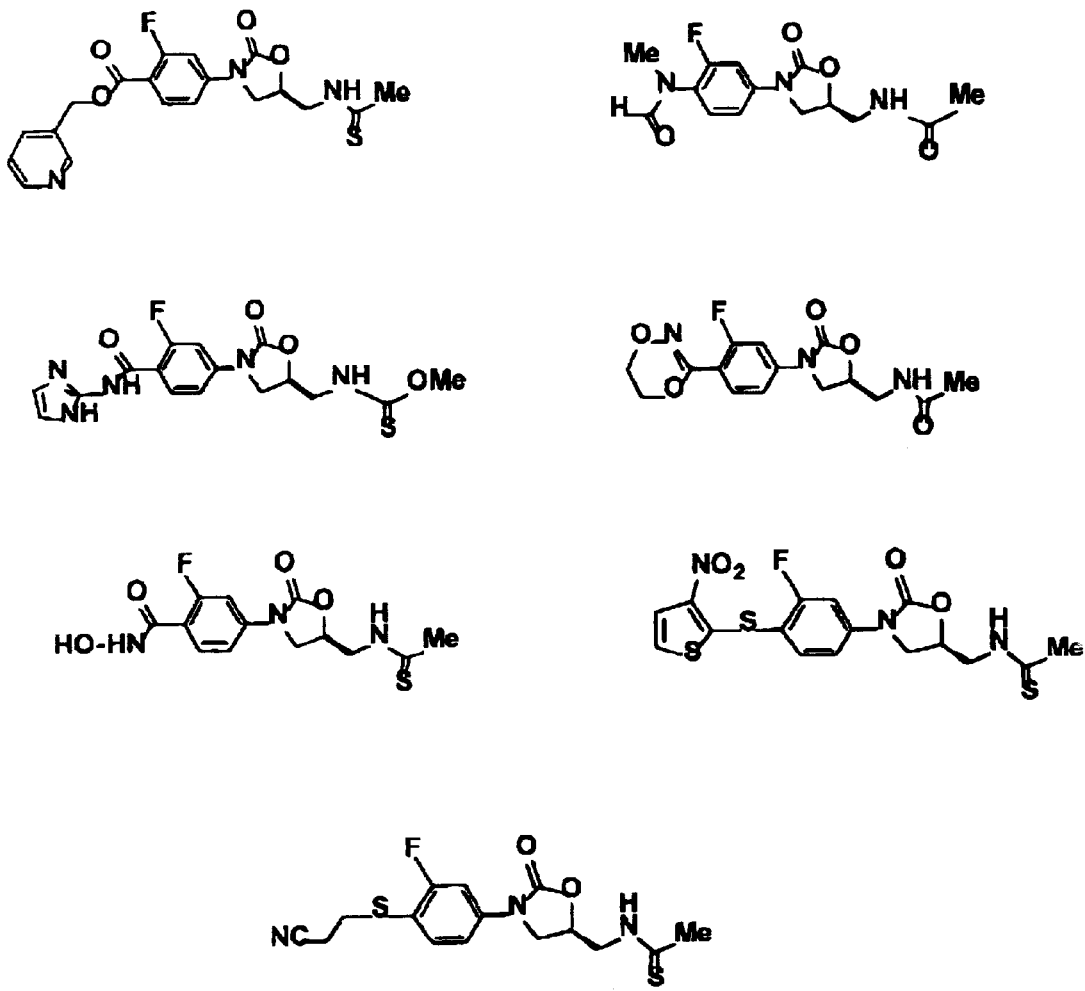
FIG. 5 shows further embodiments of the structure of some exemplary thiocarbonyl oxazolidinone compounds.

As used herein, the terms and phrases have the meanings and definitions known in the art. Some of the more commonly used phrases are described in more detail below.

"Combinatorial library" or "array" is an intentionally created collection of differing molecules which can be prepared synthetically and screened for biological activity in a variety of different formats (e.g., libraries of soluble molecules, libraries of molecules bound to a solid support). Typically, combinatorial libraries contain between about 6 and two million compounds. In one embodiment, combinatorial libraries contain between about 48 and 1 million compounds. For example, combinatorial libraries may contain between about 96 and 250,000 compounds. In another embodiment, combinatorial libraries may contain about 40 to 100 compounds.

"Alkyl" refers to a cyclic, branched or straight chain chemical group containing only carbon and hydrogen, such as methyl, pentyl, and adamantyl. Alkyl groups can either be unsubstituted or substituted with one or more substituents, e.g., halogen, alkoxy, acyloxy, amino, hydroxyl, mercapto, carboxy, benzyloxy, phenyl, and benzyl. Alkyl groups can be saturated or unsaturated (e.g., containing —C=C— or —C≡C— subunits), at one or several positions. Typically, alkyl groups will comprise about 1 to 12 carbon atoms, for example about 1 to 10, or about 1 to 8 carbon atoms.

"Heteroalkyl" refers to a cyclic, branched or straight chain chemical group containing carbon, hydrogen and at least one heteroatom. The heteroatom will be typically nitrogen, oxygen or sulfur. Heteroalkyl groups can either be unsubstituted or substituted with one or more substituents, e.g., halogen, alkoxy, acyloxy, amino, hydroxyl, mercapto, carboxy, benzyloxy, phenyl, benzyl. Where the heteroalkyl group contains a nitrogen atom, the nitrogen atom can be primary, secondary, tertiary, quaternary or can be in various forms such as an amide or sulfonamide. Heteroalkyl groups can contain one or more unsaturated (e.g., —C=C— or —C≡C—) subunits. Typically, heteroalkyl groups will comprise 1 to 12 atoms, for example 1 to 8, or 1 to 4 carbon atoms.

"Aryl" refers to a monovalent unsaturated aromatic carbocyclic group having a single ring (e.g. phenyl), multiple rings (e.g. biphenyl), or multiple condensed rings (e.g. naphthyl or anthryl). Aryl groups can be optionally unsubstituted or substituted with amino, hydroxyl, alkyl, heteroalkyl, alkoxy, halo, mercapto and other substituents. Typically, the aryl group is a substituted single ring compound. For example, the aryl group is a substituted phenyl ring.

"Heteroaryl" refers to a monovalent unsaturated aromatic carbocyclic group having a single ring (e.g., pyridyl or furyl) or multiple condensed rings (e.g., indolizinyl or benzothienyl) and having at least one heteroatom within the ring. The heteroatom in the ring is preferably nitrogen, oxygen or sulfur. Heteroaryl groups can be optionally unsubstituted or substituted with amino, hydroxyl, alkyl, heteroalkyl, alkoxy, halo, mercapto and other substituents. In one embodiment, the heteroaryl group is substituted.

"Electron withdrawing group" refers to a substituent that draws electrons to itself more than a hydrogen atom would if it occupied the same position in a molecule. This definition according to field effect is discussed in March, "Advanced Organic Chemistry," 3d Edition, pp. 16–17, Wiley-Interscience, New York. It should be contrasted with a definition based on resonance effects. Examples of electron withdrawing groups include —NR$_2$, —COOH, —OR, —SR, —F, —COR, —Cl, —SH, —NO$_2$, —Br, —NH$_2$, —SO$_2$R, —I, —OH, —CN, —C=CR$_2$, where R is alkyl, heteroalkyl, aryl or heteroaryl.

"Chemical module" refers to a general class of molecules that can be incorporated into a combinatorial library at a discrete step in the library synthesis. For example, thiols are chemical modules that can be coupled to a substrate, where the synthetic route employs a nucleophile to displace a solid support bound leaving group; isocyanates are chemical modules that can be coupled to a substrate, where the synthetic route employs an electrophile to react with a solid support bound amine. Chemical modules can contain tens, hundreds or thousands of different individual members.

"Protecting group" refers to a chemical group that exhibits the following characteristics: (1) reacts selectively with the desired functionality in good yield to give a protected substrate that is stable to the projected reactions for which protection is desired; 2) is selectively removable from the protected substrate to yield the desired functionality; and 3) is removable in good yield by reagents compatible with the other functional group(s) generated in such protection reactions. Examples of protecting groups can be found in Greene et al. (1991) *Protective Groups in Organic Synthesis,* 2nd Ed. (John Wiley & Sons, Inc., New York).

"Biologically active oxazolidinone compounds" or "bioactive oxazolidinone compounds" refers to an oxazolidinone compound that exhibits biological activity. For instance, a biologically active oxazolidinone can inhibit the interaction between an enzyme or receptor and its respective substrate(s) or endogenous ligand(s), or inhibit cell growth of a microorganism, by about at least 15% at a solution concentration of $10^{-3}$ molar or lower (i.e., it has inhibitory activity). For example, the biologically active oxazolidinone will inhibit such processes at solution concentrations of about $10^{-4}$ M or lower, or $10^{-5}$ M or lower, or, e.g., of about $10^{-6}$ M or lower.

Oxazolidinones

Provided are oxazolidinones, and compositions comprising oxazolidinones, as well as methods for their synthesis, for example, by solid phase synthesis methods, and methods for their use. A variety of oxazolidinones are provided that optionally have biological activity, such as antimicrobial activity.

In one embodiment, oxazolidinones 1 are provided:

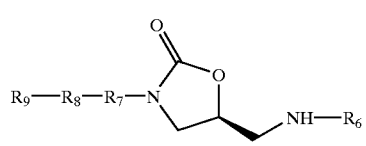

1 wherein in one embodiment:

$R_6$ is thioacyl, aminocarbonyl, alkoxycarbonyl, aminothiocarbonyl, alkoxythiocarbonyl, alkylthio(carbonyl), or alkylthio(thiocarbonyl);

$R_7$ is aryl or heteroaryl;

$R_8$ is alkyl (e.g., $C_1$–$C_7$ alkyl), alkenyl (e.g., $C_1$–$C_7$ alkenyl), alkynyl (e.g., $C_1$–$C_7$ alkynyl), NR, O, S, C(=O)NR, NRC(=O), C(=O), C(=O)O, OC(=O), OC(=O)NR, NRC(=O)O, C(=S)NR, NRC(=S), C(=S), C(=S)O, OC(=S), OC(=S)NR, NRC(=S)O, S(=O), SO$_2$, SO$_2$NR, NRSO$_2$, NRCONR', NRC (=S)NR', or $(CH_2)_nO$, wherein n=0–20, e.g., 0–6, and wherein R and R' are independently H, alkyl, heteroalkyl, aryl or heteroaryl; and $R_9$ is hydrogen, OH, OR", SR", NR"R"', alkyl, aryl, heteroalkyl, or heteroaryl, and wherein R" and R"' are independently H, alkyl, heteroalkyl, aryl or heteroaryl.

In one embodiment of the compounds of formula 1:

$R_8$ is NR, S, C(=O)NR, NRC(=O), C(=O)O, OC(=O), OC(=O)NR, C(=S)NR, NRC(=S), OC(=S)NR, NRC(=S)O, or NRC(=S)NR', wherein R and R' are independently H, alkyl, heteroalkyl, aryl or heteroaryl; and $R_9$ is hydrogen, OR", SR", NR"R"', alkyl, aryl, or heteroaryl, wherein each R" and R"' are independently H, alkyl, aryl or heteroaryl.

In one embodiment of the compounds of formula 1, $R_6$ is a thioacyl group. Exemplary thioacyl groups include C(=S)CH_3, C(=S)CH_2CH_3, C(=S)H, and C(=S)cyclopropyl.

Figure 6:
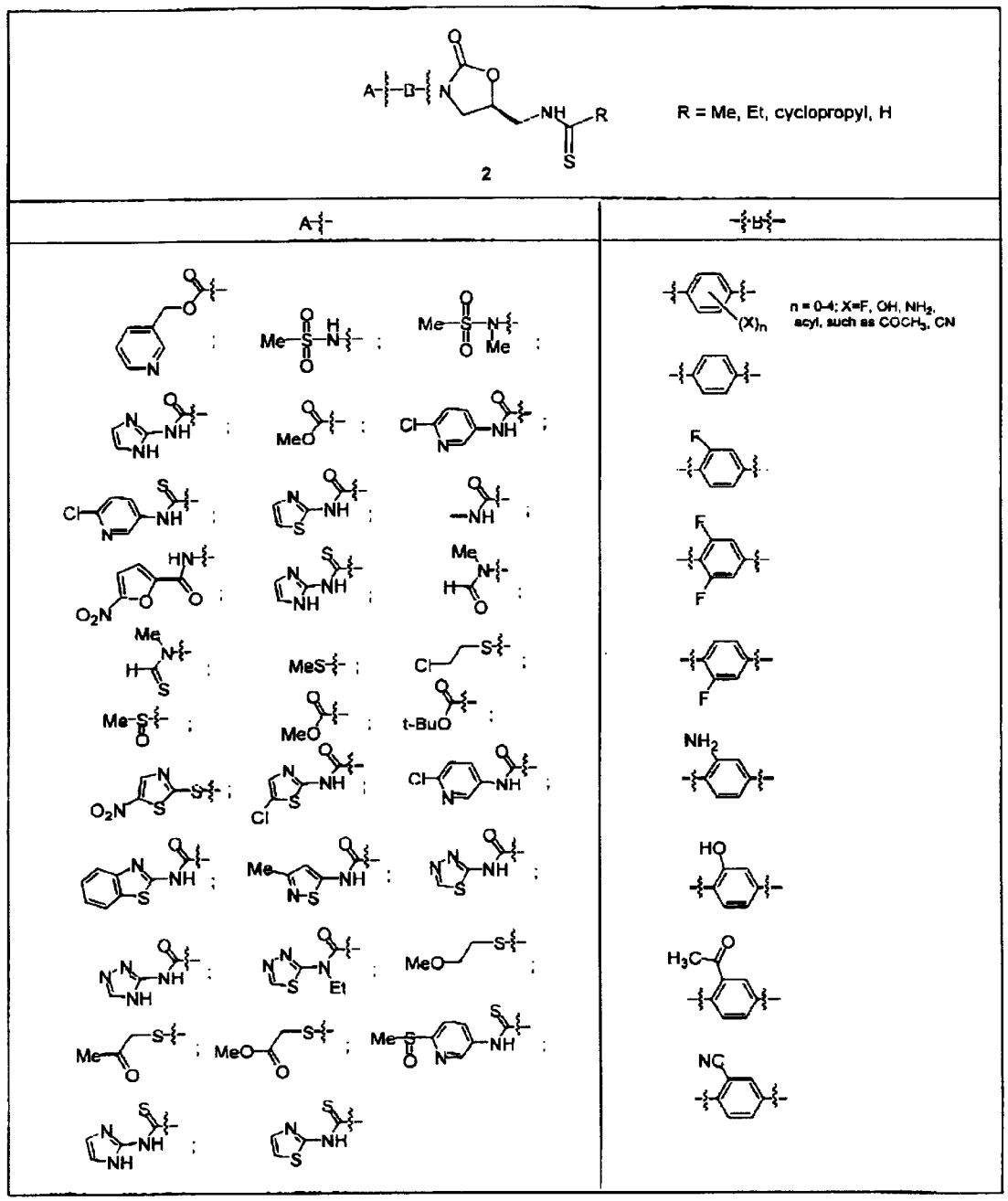
FIG. 6 shows structures of some exemplary oxazolidinone compounds of formula 2.

Examples of oxazolidinone compounds are provided in FIGS. 1–5. FIG. 6 further provides examples of oxazolidinone compounds of formula 2.

In one embodiment of the compounds of formula 1, $R_8$ is not aryl, heteroaryl, morpholino, piperazino, thiomorpholino, indolino, or thiopyrano. In one preferred embodiment, $R_7$ and $R_9$ are not directly bonded.

Also provided are compounds of formula 3:

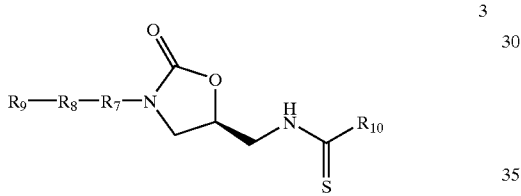

3 wherein in one embodiment:

$R_7$ is aryl or heteroaryl;

$R_8$ is alkyl (e.g., $C_1$–$C_7$ alkyl), alkenyl (e.g., $C_1$–$C_7$ alkenyl), alkynyl (e.g., as $C_1$–$C_7$ alkynyl), NR, O, S, C(=O)NR, NRC(=O), C(=O), C(=O)O, OC(=O), OC(=O)NR, NRC(=O)O, C(=S)NR, NRC(=S), C(=S), C(=S)O, OC(=S), OC(=S)NR, NRC(=S)O, S(=O), $SO_2$, $SO_2NR$, $NRSO_2$, NRCONR', NRC(=S)NR', or $(CH_2)_nO$, wherein n=0–20, e.g., 0–6, and wherein each R and R' are independently H, alkyl, heteroalkyl, aryl or heteroaryl;

$R_9$ is hydrogen, OH, OR", SR", NR"R"', alkyl, aryl, heteroalkyl, or heteroaryl, and wherein each R" and R"' are independently H, alkyl, heteroalkyl, aryl or heteroaryl; and $R_{10}$ is H, alkyl, heteroalkyl, aryl or heteroaryl.

In one embodiment of the compounds of formula 3, $R_{10}$ is H; alkyl such as $C_{1-4}$ alkyl; substituted alkyl such as $C_{1-4}$ alkyl substituted with 1–3 F, 1–2 Cl, CN, $NO_2$ or $COOC_1$–$C_4$ alkyl; or $R_{10}$ is a $C_{3-6}$ cycloalkyl.

In one embodiment, $R_{10}$ is $CH_3$, $CH_2CH_3$, or cyclopropyl.

In another embodiment of the compounds of formula 3, $R_8$ is NR, S, C(=O)NR, NRC(=O), C(=O)O, OC(=O), OC(=O)NR, C(=S)NR, NRC(=S), OC(=S)NR, NRC(=S)O, or NRC(=S)NR', wherein R and R' are independently H, alkyl, heteroalkyl, aryl or heteroaryl; and $R_9$ is hydrogen, OR", SR", NR"R"', alkyl, aryl, or heteroaryl, wherein R" and R"' are independently H, alkyl, aryl or heteroaryl.

There further is provided compounds of formula 4:

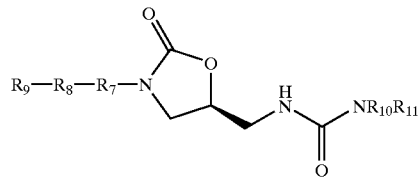

4 wherein:

$R_7$ is aryl or heteroaryl;

$R_8$ is NR, S, C(=O)NR, NRC(=O), C(=O)O, OC(=O), OC(=O)NR, C(=S)NR, NRC(=S), OC(=S)NR, NRC(=S)O, or NRC(=S)NR', wherein R and R' are independently H, alkyl, heteroalkyl, aryl or heteroaryl; and $R_9$ is hydrogen, OR", SR", NR"R"', alkyl, aryl, or heteroaryl, wherein R" and R"' each are independently H, alkyl, heteralkyl, aryl or heteroaryl; and $R_{10}$ and $R_{11}$ are independently hydrogen, alkyl, heteroalkyl, aryl or heteroaryl, or $NR_{10}R_{11}$ is $NH_2$, $NHC_{1-4}$ alkyl, $N(C_1-C_4alkyl)_2$, or $N(CH_2)_{2-5}$.

There further are provided compounds of formula 5:

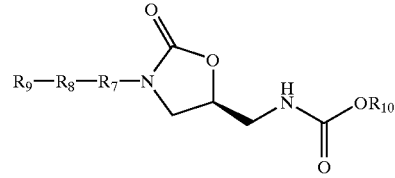

5 wherein, in one embodiment:

$R_7$ is aryl or heteroaryl;

$R_8$ is NR, S, C(=O)NR, NRC(=O), C(=O)O, OC(=O), OC(=O)NR, C(=S)NR, NRC(=S), OC(=S)NR, NRC(=S)O, or NRC(=S)NR', wherein R and R' are independently H, alkyl, heteroalkyl, aryl or heteroaryl; and $R_9$ is hydrogen, OR", SR", NR"R"', alkyl, aryl, or heteroaryl, wherein R" and R"' each are independently H, alkyl, heteroalkyl, aryl or heteroaryl; and $R_{10}$ is alkyl, $C_1$–$C_4$ alkyl, heteroalkyl, aryl or heteroaryl.

Also provided are compounds of formula 6:

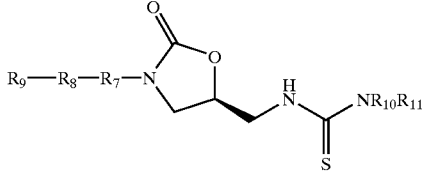

6 wherein in one embodiment:

$R_7$ is aryl or heteroaryl;

$R_8$ is alkyl (such as $C_1$–$C_7$ alkyl), alkenyl (such as $C_1$–$C_7$ alkenyl), alkynyl (such as $C_1$–$C_7$ alkynyl), NR, O, S, C(=O)NR, NRC(=O), C(=O), C(=O)O, OC(=O), OC(=O)NR, NRC(=O)O, C(=S)NR, NRC(=S), C(=S), C(=S)O, OC(=S), OC(=S)NR, NRC(=S)O, S(=O), $SO_2$, $SO_2NR$, $NRSO_2$, NRCONR', NRC(=S)NR', or $(CH_2)_nO$, wherein n=0–20, such as 0–6, and wherein R and R' are independently H, alkyl, heteroalkyl, aryl or heteroaryl;

$R_9$ is hydrogen, OH, OR", SR", NR"R''', alkyl, aryl, heteroalkyl, or heteroaryl, and wherein R" and R''' are independently H, alkyl, heteroalkyl, aryl or heteroaryl;

$R_{10}$ and $R_{11}$ are independently hydrogen, alkyl, heteroalkyl, aryl or heteroaryl; or $NR_{10}R_{11}$ is $NH_2$, $NHC_{1-4}$ alkyl, $N(C_1-C_4 alkyl)_2$, or $N(CH_2)_{2-5}$.

In one embodiment, there are provided compounds of formula 6, wherein:

$R_9$ is NR, S, C(=O)NR, NRC(=O), C(=O)O, OC(=O), OC(=O)NR, C(=S)NR, NRC(=S), OC(=S)NR, NRC(=S)O, or NRC(=S)NR', wherein R and R' are independently H, alkyl, heteroalkyl, aryl or heteroaryl; and $R_9$ is hydrogen, OR", SR", NR"R''', alkyl, aryl, or heteroaryl, wherein R" and R''' are independently H, alkyl, aryl or heteroaryl.

Further provided are compounds of formula 7:

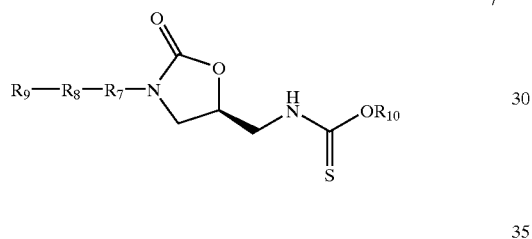

7 wherein in one embodiment:

$R_7$ is aryl or heteroaryl;

$R_8$ is alkyl (such as $C_1-C_7$ alkyl), alkenyl (such as $C_1-C_7$ alkenyl), alkynyl (such as $C_1-C_7$ alkynyl), NR, O, S, C(=O)NR, NRC(=O), C(=O), C(=O)O, OC(=O), OC(=O)NR, NRC(=O)O, C(=S)NR, NRC(=S), C(=S), C(=S)O, OC(=S), OC(=S)NR, NRC(=S)O, S(=O), $SO_2$, $SO_2NR$, $NRSO_2$, NRCONR', NRC(=S)NR', or $(CH_2)_nO$, wherein n=0–6, and wherein R and R' are independently H, alkyl, heteroalkyl, aryl or heteroaryl;

$R_9$ is hydrogen, OH, OR", SR", NR"R''', alkyl, aryl, heteroalkyl, or heteroaryl, and wherein R" and R''' are independently H, alkyl, heteroalkyl, aryl or heteroaryl; and $R_{10}$ is alkyl, heteroalkyl, aryl or heteroaryl.

In one embodiment of the compounds of formula 7:

$R_8$ is NR, S, C(=O)NR, NRC(=O), C(=O)O, OC(=O), OC(=O)NR, C(=S)NR, NRC(=S), OC(=S)NR, NRC(=S)O, or NRC(=S)NR', wherein R and R' are independently H, alkyl, heteroalkyl, aryl or heteroaryl; and $R_9$ is hydrogen, OR", SR", NR"R''', alkyl, aryl, or heteroaryl, wherein R" and R''' are independently H, alkyl, aryl or heteroaryl.

Also provided are compounds of the structure 1b:

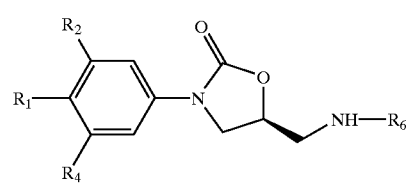

1b wherein, in one embodiment:

$R_2$ and $R_4$ are, independently, hydrogen, alkyl, heteroalkyl, heteroaryl or an electron withdrawing group;

$R_6$ is thioacyl, aminocarbonyl, alkoxycarbonyl, aminothiocarbonyl, alkoxythiocarbonyl, alkylthio (carbonyl), or alkylthio(thiocarbonyl); and $R_1$ is:

$C(O)NR_7R_8$, $C(S)NR_7R_8$, $OC(O)NR_7R_8$, $OC(S)NR_7R_8$, $NR_7C(O)N R_8R_9$, $NR_7C(S)N R_8R_9$, wherein $R_7$, $R_8$, and $R_9$ are, independently, hydrogen, alkyl, heteroalkyl, aryl or heteroaryl;

$C(O)OR_{10}$, wherein $R_{10}$ is hydrogen, alkyl, heteroalkyl, aryl or heteroaryl;

$C(O)R_{11}$, wherein $R_{11}$ is hydrogen, alkyl, heteroalkyl, aryl or heteroaryl;

$SR_{12}$, $S(O)_2R_{12}$, or $S(O)R_{12}$, wherein $R_{12}$ is hydrogen, alkyl, heteroalkyl, aryl or heteroaryl;

$NR_{13}R_{14}$ wherein $R_{13}$ and $R_{14}$ are, independently, hydrogen, acyl, sulfonyl, alkyl, heteroalkyl, aryl or heteroaryl;

2-oxazolyl comprising $R_{15}$ at the 4-position and $R_{16}$ at the 5-position of the oxazolyl, wherein $R_{15}$ and $R_{16}$ are, independently, hydrogen, alkyl, heteroalkyl, aryl, heteroaryl or an electron withdrawing group;

2-aminothiazolyl comprising $R_{17}$ at the 4-position and $R_{18}$ at the 5-position of the thiazole, wherein $R_{17}$ and $R_{18}$, are, independently, hydrogen, alkyl, heteroalkyl, aryl, heteroaryl or an electron withdrawing group; and $CH_2NR_{19}R_{20}$, wherein $R_{19}$ and $R_{20}$ are, independently, hydrogen, alkyl, heteroalkyl, aryl, heteroaryl, acyl or sulfonyl;

2-(1,3,4-thiadiazolyl) comprising $R_{21}$ at the 5-position of the 1,3,4-thiadiazole, wherein $R_{21}$ is hydrogen, alkyl, heteroalkyl, amino($C_{1-4}$ alkyl), acylamino ($C_{1-4}$ alkyl), thioacylamino($C_{1-4}$ alkyl), sulfonamido ($C_{1-4}$ alkyl), heterocarbonylamino($C_{1-4}$ alkyl), aryl, heteroaryl, an electron withdrawing group, or $NR_{22}R_{23}$, wherein $R_{22}$ and $R_{23}$ are, independently, hydrogen, acyl, thioacyl, sulfonyl, alkyl, heteroalkyl, aryl or heteroaryl;

$CH=CHR_{24}$ or $C\equiv CR_{24}$, wherein $R_{24}$ is $C(O)NR_7R_8$, $C(S)NR_7R_8$, $OC(O)NR_7R_8$, $OC(S)NR_7R_8$, $NR_7C(O)N R_9 R_9$, $NR_7C(S)N R_8R_9$, $C(O)OR_{10}$, $C(O)R_{11}$, $SR_{12}$, $S(O)_2R_{12}$, $S(O)R_{12}$, $NR_{13}R_{14}$, $CH_2NR_{19}R_{20}$, alkyl, aryl, or heteroaryl; or 5,6-dihydro-1,4,2-dioxazine-3-yl, wherein $R_{25}$ is at the 5-position of dioxazine, and $R_{26}$ is at the 6-position of dioxazine, and wherein $R_{25}$ and $R_{26}$, are, independently, hydrogen, alkyl, heteroalkyl, aryl, heteroaryl or an electron withdrawing group; and wherein optionally $R_1$ and $R_2$ together are a quinolone heterocycle $C(=O)C(COOH)=CHNR_{27}$, or $R_1$ and $R_2$ together are a benzotriazole heterocycle $NNNR_{27}$, or $NN(R_{27})N$, wherein $R_{27}$ is alkyl, aryl, or heteroaryl.

Exemplary structures are shown below:

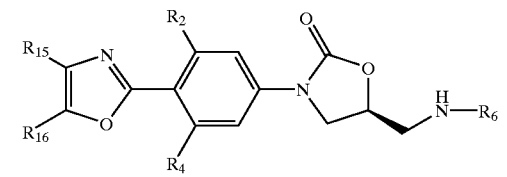

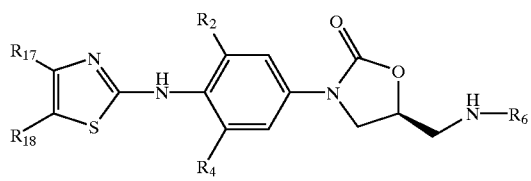

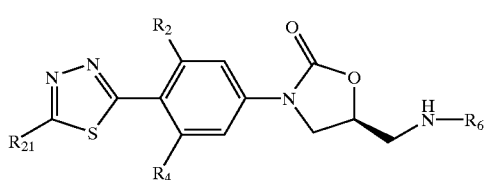

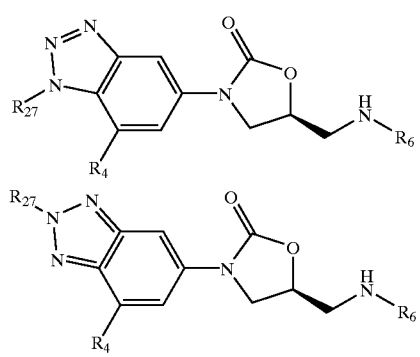

In one embodiment of the compounds of formula 1b: $R_1$ is $C(O)NR_7R_8$, $SR_{11}$, $C(S)NR_7R_8$, $C(O)OR_{10}$, $C(O)R_{11}$, $SR_{12}$, $S(O)_2R_{12}$, $S(O)R_{12}$ or $NR_{13}R_8$, In another embodiment of the compounds of formula 1b: $R_1$ is $NR_x(C=O)R_y$, wherein $R_x$ and $R_y$ are independently hydrogen, alkyl, heteroalkyl, aryl, or heteroaryl. In another embodiment, $R_1$ is $NR_x(SO_2)R_y$, wherein $R_x$ and $R_y$ are independently hydrogen, alkyl, heteroalkyl, aryl, or heteroaryl with the proviso that $R_y$ is not H. In another embodiment, $R_1$ is 2-oxazolyl, wherein $R_{15}$ is at the 4-position and $R_{16}$ is at the 5-position of the oxazole group. In a further embodiment, $R_1$ is 2-aminothiazolyl, wherein $R_{17}$ is at the 4-position and $R_{18}$ is at the 5-position of the aminothiazolyl group.

In one embodiment of the compounds of formula 1b, $R_4$ is hydrogen; $R_2$ is fluorine; $R_6$ is $C(S)C_{1-7}$ alkyl or $C(S)C_{3-6}$ cycloalkyl; $R_1$ is $C(O)NR_7R_8$ and $R_7$ is hydrogen; and/or $R_8$ is heteroaryl. In another embodiment, $R_4$ is hydrogen; $R_2$ is fluorine; and/or $R_6$ is $C(S)CH_3$, and $NR_7R_8$ is NH(5'-(5-aminopyridine-2-yl)thiopyridine-3'-yl) or NH(pyridine-3-yl) or NH(5-chloropyridine-3-yl).

Exemplary compounds of formula 1 are as follows. MIC refers to the minimal inhibitory concentration which was determined as described in Example 37.

In one embodiment, the compound shown below is provided, with, for example, an MIC of 4–8 Tg/mL (*S. aureus*).

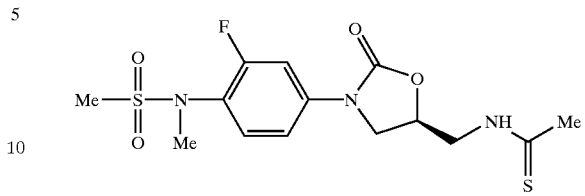

In another embodiment, the five compounds shown below are provided, with, for example, an MIC of 0.25 to 4 Tg/mL (*S. aureus*).

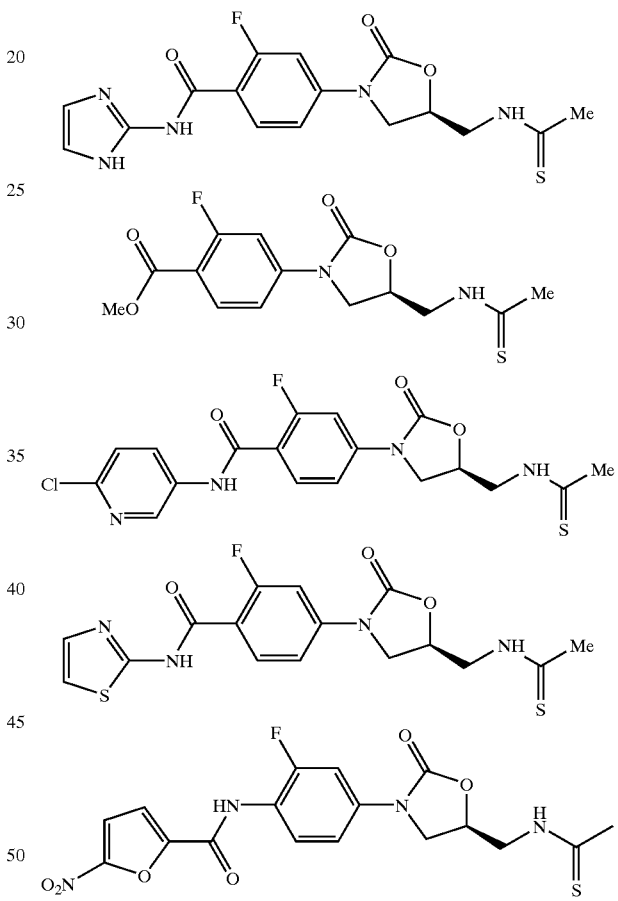

Other exemplary compounds include:

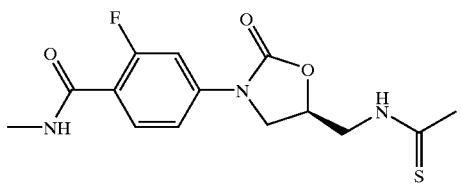

Exemplary compounds active against a fastidious Gram-negative microorganism *H. influenzae* are the following five compounds with an MIC of 2–8 Tg/nmL (*H. influenzae*):

or $(CH_2)_nO$, wherein n=0–20, such as 0–6, and wherein R and R' are independently H, alkyl, heteroalkyl, aryl or heteroaryl; and $R_9$ is hydrogen, OH, OR", SR", NR"R'", alkyl, aryl, heteroalkyl, or heteroaryl, and wherein R" and R'" are independently H, alkyl, heteroalkyl, aryl or heteroaryl.

In one embodiment of the compounds of formula 3c:

$R_6$ is $C(S)C_{1-7}$ alkyl or $C(S)C_{3-6}$ cycloalkyl;

$R_7$ is aryl;

$R_8$ is S; and $R_9$ is alkyl or heteroalkyl.

In another embodiment of the compounds of formula 3c:

$R_6$ is $C(S)C_{1-7}$ alkyl or $C(S)C_{3-6}$ cycloalkyl;

$R_7$ is aryl;

$R_8$ is S(=O); and $R_9$ is alkyl.

In another embodiment of the compounds of formula 3c:

$R_6$ is $C(S)C_{1-7}$ alkyl or $C(S)C_{3-6}$ cycloalkyl;

$R_7$ is aryl;

$R_8$ is OC(=O); and $R_9$ is alkyl.

Examples of compounds of formula 3c include the following compound with MIC 4–8 Tg/mL (*S. aureus*).

Examples of compounds also include the following five compounds with MIC 0.25–4 Tg/mL (*S. aureus*).

Also provided are compounds of formula 3c:

3c wherein in one embodiment:

$R_2$ and $R_4$ are, independently, hydrogen, alkyl, heteroalkyl, heteroaryl or an electron withdrawing group;

$R_6$ is thioacyl, aminocarbonyl, alkoxycarbonyl, aminothiocarbonyl, alkoxythiocarbonyl, alkylthio(carbonyl), or alkylthio(thiocarbonyl);

$R_8$ is alkyl (such as $C_1$–$C_7$ alkyl), alkenyl (such as $C_1$–$C_7$ alkenyl), alkynyl (such as $C_1$–$C_7$ alkynyl), NR, O, S, C(=O)NR, C(=S)NR, NRC(=O), NRC(=S), C(=O), C(=O)O, C(=S)O, OC(=O), OC(=S), S(=O), $SO_2$, $SO_2NR$, $NRSO_2$, NRCONR', NRCSNR', -continued

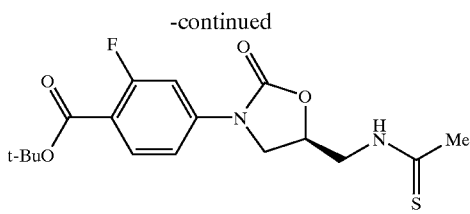

Also provided are compounds of formula 4c:

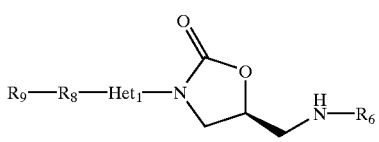

wherein in one embodiment:
- $R_6$ is thioacyl, aminocarbonyl, alkoxycarbonyl, aminothiocarbonyl, alkoxythiocarbonyl, alkylthio(carbonyl), or alkylthio(thiocarbonyl);
- $Het_1$ is heteroaryl;
- $R_8$ is alkyl (such as $C_1-C_7$ alkyl), alkenyl (such as $C_1-C_7$ alkenyl), alkynyl (such as $C_1-C_7$ alkynyl), NR, O, S, C(=O)NR, C(=S)NR, NRC(=O), NRC(=S), C(=O), C(=O)O, C(=S)O, OC(=O), OC(=S), S(=O), $SO_2$, $SO_2NR$, $NRSO_2$, NRCONR', NRCSNR', or $(CH_2)_nO$, wherein n=0–20, e.g., 0–6, and wherein R and R' are independently H, alkyl, heteroalkyl, aryl or heteroaryl; and
- $R_9$ is hydrogen, OH, OR", SR", NR"R'", alkyl, aryl, heteroalkyl, or heteroaryl, and wherein R" and R'" are independently H, alkyl, heteroalkyl, aryl or heteroaryl.

Also provided are compounds of formula 5c:

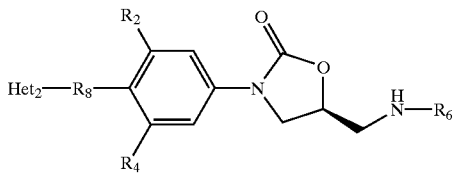

wherein:
- $R_2$ and $R_4$ are, independently, hydrogen, alkyl, heteroalkyl, heteroaryl or an electron withdrawing group;
- $R_6$ is thioacyl, aminocarbonyl, alkoxycarbonyl, aminothiocarbonyl, alkoxythiocarbonyl, alkylthio(carbonyl), or alkylthio(thiocarbonyl);
- $R_8$ is alkyl (such as $C_1-C_7$ alkyl), alkenyl (such as $C_1-C_7$ alkenyl), alkynyl (such as $C_1-C_7$ alkynyl), NR, O, S, C(=O)NR, C(=S)NR, NRC(=O), NRC(=S), C(=O), C(=O)O, C(=S)O, OC(=O), OC(=S), S(=O), $SO_2$, $SO_2NR$, $NRSO_2$, NRCONR', NRCSNR', or $(CH_2)_nO$, wherein n=0–20, e.g., 0–6, and wherein R and R' are independently H, alkyl, heteroalkyl, aryl or heteroaryl; and
- $Het_2$ is a heterocyclic group.

In one embodiment of the compounds of formula 5c:
- $R_6$ is $C(S)C_{1-7}$ alkyl or $C(S)C_{3-6}$ cycloalkyl;
- $R_7$ is aryl;
- $R_8$ is S; and $Het_2$ is a thienylphenyl or thiazolyl group.

In another embodiment of the compounds of formula 5c:
- $R_6$ is $C(S)C_{1-7}$ alkyl or $C(S)C_{3-6}$ cycloalkyl;
- $R_7$ is aryl;
- $R_8$ is NH; and
- $Het_2$ is 1,3,5-triazinyl.

In one embodiment, the compound has the structure:

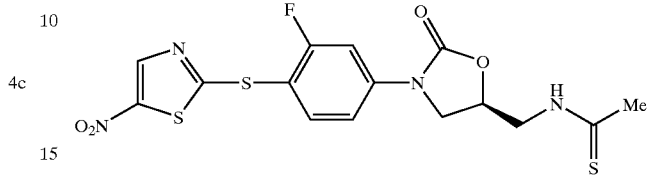

Other Oxazolidinone Compounds

In another embodiment, there are provided compounds of formula 8:

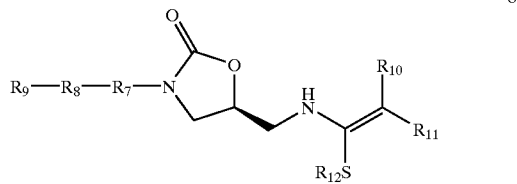

wherein:
- $R_7$ is aryl or heteroaryl;
- $R_9$ is $C_1-C_7$ alkyl, $C_1-C_7$ alkenyl, $C_1-C_7$ alkynyl, NR, O, S, C(=O)NR, NRC(=O), C(=O), C(=O)O, OC(=O), OC(=O)NR, NRC(=O)O, C(=S)NR, NRC(=S), C(=S), C(=S)O, OC(=S), OC(=S)NR, NRC(=S)O, S(=O), $SO_2$, $SO_2NR$, $NRSO_2$, NRCONR', NRC(=S)NR', or $(CH_2)_nO$, wherein n=0–6, and wherein: R and R' are independently H, alkyl, heteroalkyl, aryl or heteroaryl;
- $R_9$ is hydrogen, OH, OR", SR", NR"R'", alkyl, aryl, heteroalkyl, or heteroaryl, and wherein R" and R'" are independently H, alkyl, heteroalkyl, aryl or heteroaryl;
- $R_{10}$ and $R_{11}$ are independently hydrogen, alkyl, heteroalkyl, aryl, heteroaryl, acyl, thioacyl, CN, $NO_2$, alkoxycarbonyl, $COOC_{1-4}$ alkyl, sulfonyl, aminocarbonyl, aminothiocarbonyl, or alkoxythiocarbonyl; and
- $R_{12}$ is hydrogen, alkyl, heteroalkyl, aryl, or heteroaryl.

Also provided are compounds of formula 9:

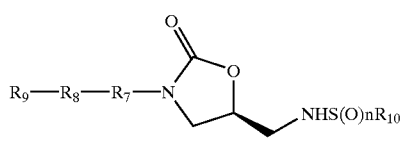

wherein:
- $R_7$ is aryl or heteroaryl;
- $R_8$ is $C_1-C_7$ alkyl, $C_1-C_7$ alkenyl, $C_1-C_7$ alkynyl, NR, O, S, C(=O)NR, NRC(=O), C(=O), C(=O)O, OC(=O), OC(=O)NR, NRC(=O)O, C(=S)NR, NRC(=S), C(=S), C(=S)O, OC(=S), OC(=S)NR, NRC(=S)O, S(=O), $SO_2$, $SO_2NR$, $NRSO_2$, NRCONR', NRC(=S)NR', or $(CH_2)_nO$, wherein n=0–6, and wherein R and R' are independently H, alkyl, heteroalkyl, aryl or heteroaryl;

$R_9$ is hydrogen, OH, OR", SR", NR"R'", alkyl, aryl, heteroalkyl, or heteroaryl, and wherein R" and R'" are independently H, alkyl, heteroalkyl, aryl or heteroaryl; and $R_{10}$ is alkyl, heteroalkyl, aryl, or heteroaryl, and n=0–2.

Further provided are compounds of formula 11:

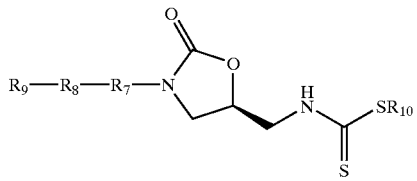

11 wherein:

$R_7$ is aryl or heteroaryl;

$R_8$ is $C_1$–$C_7$ alkyl, $C_1$–$C_7$ alkenyl, $C_1$–$C_7$ alkynyl, NR, O, S, C(=O)NR, NRC(=O), C(=O), C(=O)O, OC(=O), OC(=O)NR, NRC(=O)O, C(=S)NR, NRC(=S), C(=S), C(=S)O, OC(=S), OC(=S)NR, NRC(=S)O, S(=O), $SO_2$, $SO_2$NR, $NRSO_2$, NRCONR', NRC(=S)NR', or $(CH_2)_nO$, wherein n=0–6, and wherein R and R' are independently H, alkyl, heteroalkyl, aryl or heteroaryl;

$R_9$ is hydrogen, OH, OR", SR", NR"R'", alkyl, aryl, heteroalkyl, or heteroaryl, and wherein R" and R'" are independently H, alkyl, heteroalkyl, aryl or heteroaryl; and $R_{10}$ is alkyl, $C_{1-4}$ alkyl, heteroalkyl, aryl or heteroaryl.

In another embodiment, there are provided compounds of formula 12:

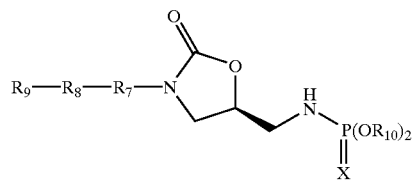

12 wherein:

$R_7$ is aryl or heteroaryl;

$R_8$ is $C_1$–$C_7$ alkyl, $C_1$–$C_7$ alkenyl, $C_1$–$C_7$ alkynyl, NR, O, S, C(=O)NR, NRC(=O), C(=O), C(=O)O, OC(=O), OC(=O)NR, NRC(=O)O, C(=S)NR, NRC(=S), C(=S), C(=S)O, OC(=S), OC(=S)NR, NRC(=S)O, S(=O), $SO_2$, $SO_2$NR, $NRSO_2$, NRCONR', NRC(=S)NR', or $(CH_2)_nO$, wherein n=0–6, and wherein R and R' are independently H, alkyl, heteroalkyl, aryl or heteroaryl;

$R_9$ is hydrogen, OH, OR", SR", NR"R'", alkyl, aryl, heteroalkyl, or heteroaryl, and wherein R" and R'" are independently H, alkyl, heteroalkyl, aryl or heteroaryl;

$R_{10}$ is alkyl, heteroalkyl, aryl or heteroaryl; and

X=O, S.

Further provided are compounds of formula 13:

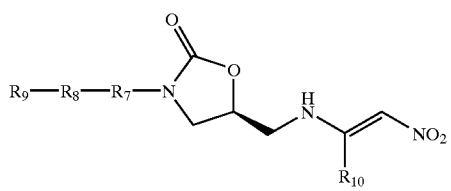

13 wherein:

$R_7$ is aryl or heteroaryl;

$R_8$ is $C_1$–$C_7$ alkyl, $C_1$–$C_7$ alkenyl, $C_1$–$C_7$ alkynyl, NR, O, S, C(=O)NR, NRC(=O), C(=O), C(=O)O, OC(=O), OC(=O)NR, NRC(=O)O, C(=S)NR, NRC(=S), C(=S), C(=S)O, OC(=S), OC(=S)NR, NRC(=S)O, S(=O), $SO_2$, $SO_2$NR, $NRSO_2$, NRCONR', NRC(=S)NR', or $(CH_2)_nO$, wherein n=0–6, and wherein R and R' are independently H, alkyl, heteroalkyl, aryl or heteroaryl;

$R_9$ is hydrogen, OH, OR", SR", NR"R'", alkyl, aryl, heteroalkyl, or heteroaryl, and wherein R" and R'" are independently H, alkyl, heteroalkyl, aryl or heteroaryl; and $R_{10}$ is hydrogen, thiol, alkyl, heteroalkyl, aryl or heteroaryl.

Synthesis of Oxazolidinones

Oxazolidinones such as 3-(heteroaryl)oxazolidinones may be synthesized by a variety of routes as disclosed herein. Exemplary methods of synthesis of oxazolidinone compounds are described in U.S. patent application Ser. No. 09/012,535, filed Jan. 23, 1998, U.S. patent application Ser. No. 09/086,702, filed May 28, 1998, U.S. patent application Ser. No. 09/235,771, filed Jan. 22, 1999, and PCT/US99/01318, filed Jan. 22, 1999, the disclosures of which are incorporated herein by reference in their entirety.

In one embodiment, oxazolidinone compounds can be synthesized by: attaching a plurality of aryl or heteroaryl oxazolidinones to a plurality of solid supports; functionalizing the substituents in aryl or heteroaryl groups of the attached oxazolidinones; removing the oxazolidinones from the solid supports in form of 5-aminomethyloxazolidinones; and functionalizing the amino group of cleaved 5-aminomethylox azolidinones with an appropriate thioacylating reagent(s) to produce 5-(thiocarbonyl) aminooxazolidinone derivatives.

The final thioacylation step can be performed, e.g., with alkyl dithiocarboxylate. The final thioacylation step can be performed, for example, with a polymeric reagent of the structure

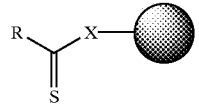

wherein

R is an alkyl, aryl, heteroaryl, alkoxy, alkylthio, or amino group;

X is O, S, N-(alkoxy)amine, benzotriazole, benzimidazolone, imidazole, or alike electron withdrawing N-heterocyclic group; and the polymer carrier is polystyrene, polyethyleneglycol (PEG), PEG grafted polystyrene, or alike polymer.

The polymeric thioacylating reagent can be produced by thioacylation of an alcohol, thiol, or NH-functionalized polymer carrier. The polymeric thioacylating reagent can be produced by stepwise reaction involving (i) acylation of NH-functionalized polymer, and (ii) conversion of the amide intermediate into reactive thioamide with thionation reagents, such as Lawesson, Davy, Yokoyama, or Belleau reagents, $Na_2P_4S_{11}$, $Na_2P_4S_{10}O$, or alike known compounds capable of converting amides into thioamides. The polymeric thioacylating reagent can be produced by reaction of dithiocarboxylates with appropriate polymeric alkylation reagents, such as chloroalkyl functionalized resins.

In another embodiment, a method of preparing an oxazolidinone compound is provided, the method comprising: attaching an aryl or heteroaryl oxazolidinone to a solid support to form a linkage between a functional group on the support and the nitrogen of a 5-aminomethyl group of the oxazolidinone; acylating the 5-aminomethyloxazolidinone group of the attached oxazolidinone to form a 5-amidomethyl group; functionalizing a substituent in an aryl or heteroaryl group of the attached oxazolidinone; converting the 5-amidomethyl group of an attached oxazolidinone into a 5-thioamido group; and removing the 5-thioamidomethyloxazolidinone from the polymer carrier.

In another embodiment, a method for a solid phase synthesis of oxazolidinone compounds is provided comprising the treatment of an amide precursor comprising a group such as $NC(O)R_{10}$, immobilized on a support, wherein $R_{10}$ is a substituent such as alkyl, heteroalkyl, aryl or heteroaryl, with a thionation reagent; and release of a compound of formula 3 from the support. One embodiment is illustrated in Scheme 2 below.

Synthetic Schemes

Embodiments of schemes for synthesis of oxazolidinone compounds are shown below by way of example. Based on the disclosure herein a wide variety of oxazolidinones as defined herein may be synthesized. The specific structures, such as the fluorophenyl ring, are shown by way of example, and are not to be considered to be limiting. The synthesis may be readily conducted with other starting materials, including compounds comprising other substituted or unsubstituted phenyl rings.

As illustrated in Scheme 1, below, for example, N-substituted 5-(S)-aminomethyloxazolidinones can be produced by transformations of 5-(S)-aminomethyloxazolidinones with various known electrophilic reagents capable of reacting with a primary or secondary amines with or without use of organic or inorganic bases.

In one embodiment, such syntheses can be performed in solution using 5-(S)-aminomethyloxazolidinone derivatives as primary amine reagents. In another embodiment, 5-(S)-aminomethyloxazolidinone or 5-(S)-azidomethyloxazolidinones can be first immobilized on polymeric supports using appropriate linker groups (e.g., aldehyde or benzyl halide-type acid- or photo-cleavable linkers) to produce an immobilized 5-(S)-aminomethyloxazolidinone. The latter functionalized compounds can be treated with appropriate electrophilic reagents to introduce the desired N-substituent(s). Resulting tethered products can be released from supports using cleavage reagents (e.g., trifluororacetic acid) or light (when photo-cleavable linkers are employed).

Scheme 1. Examples for general synthesis of N-substituted 5-(S)-aminomethyloxazolidinone derivatives.

1. Solution synthesis from 5-(S)-aminomethyloxazolidinone derivatives:

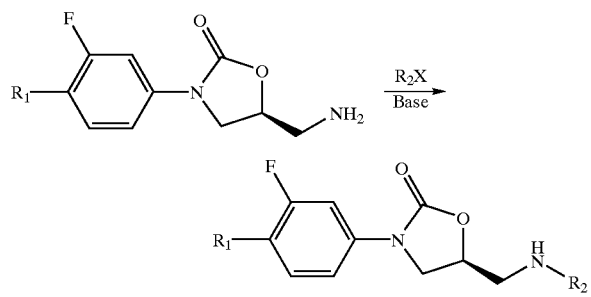

2. Solid phase syntheses from immobilized 5-(S)-aminomethyloxazolidinone derivatives:

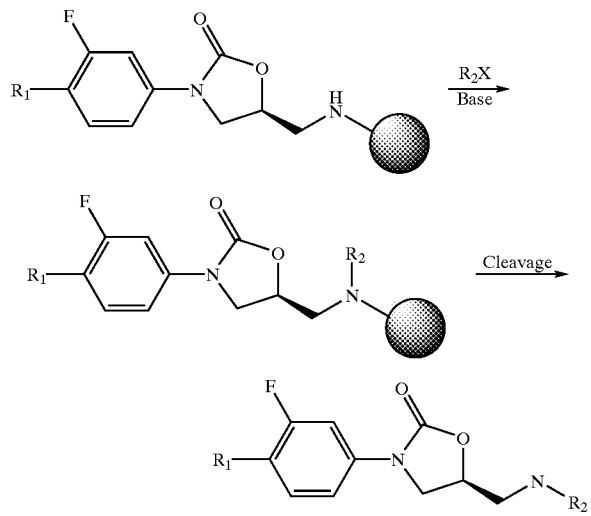

$R_2$ = For example, RC(═S), ROC(═S), RNR'C(═S), RSC(═S), RS(═O), $(RO)_2P$(═O), $(RO)_2P$(═S), where R, $R_1$ and R' are substituents such as alkyl or heteroalkyl.
X = Cl, Br, SR, OR, $SO_2R$, benzotriazole, or other electron withdrawing leaving group.

The synthesis is shown generally below in Scheme 1a.

Scheme 1a. Examples for general sythesis of N-substituted 5-(S)-aminomethyloxazolidinone deriviatives.

1. Synthesis from 5-(S)-aminomethyl derivatives and electrophilic capping reagents

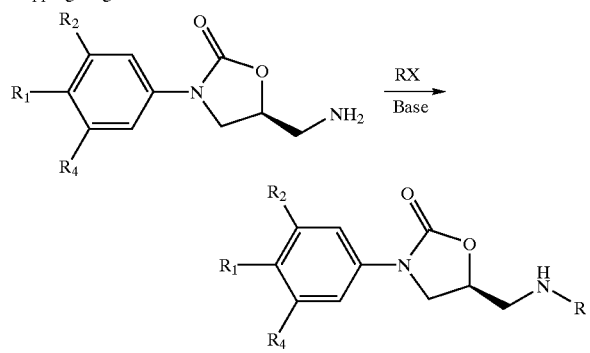

-continued

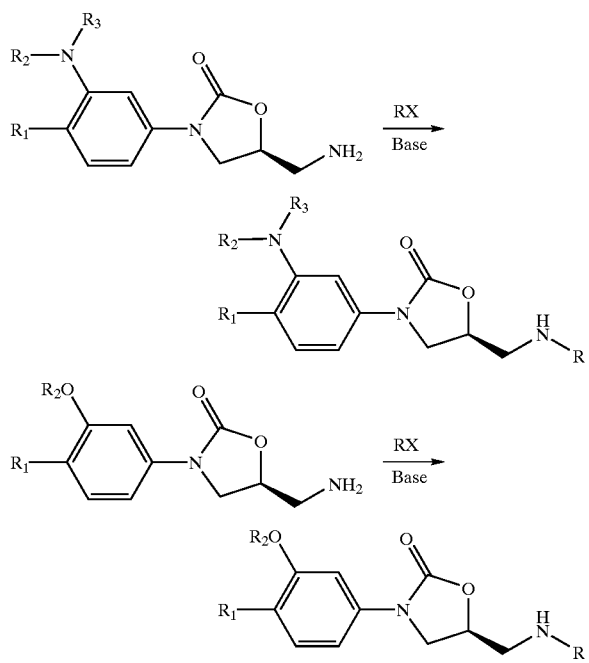

R = For example, RC(=S), ROC(=S), RNR'C(=S),
RSC(=S), RS(=O), (RO)₂P(=O), (RO)₂P(=S),
X = Cl, Br, SR, OR, SO₂R, benzotriazole, or other electron withdrawing leaving group.
Examples: RX = RC(=S)SAlk, ROC(=S)Cl, RSC(=S)SAlkl, RS(=O)Cl, (RO)₂P(=O)Cl, (RO)₂P(=S)Cl;
All R$_{1-5}$, R, and R' groups are independently different substituents such as alkly and heteroalkyl.

2. Synthesis from 5-(S)-amidomethyl derivatives and thionation reagents

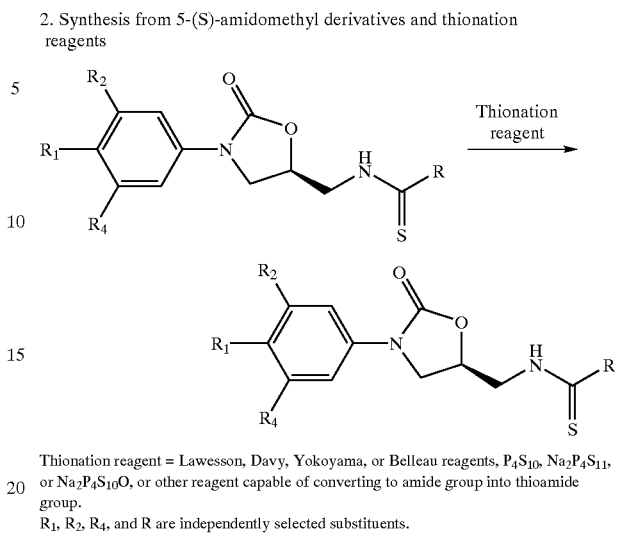

Thionation reagent = Lawesson, Davy, Yokoyama, or Belleau reagents, P₄S₁₀, Na₂P₄S₁₁, or Na₂P₄S₁₀O, or other reagent capable of converting to amide group into thioamide group.
R₁, R₂, R₄, and R are independently selected substituents.

In another embodiment, the resulting tethered N-substituted 5-(S)-aminomethyloxazolidinone derivatives can be subjected to various chemical transformations in other parts of the molecule prior to the cleavage from supports, analogously to such transformations of immobilized 5-(S)-amidomethyloxazolidinones as described in U.S. patent application Ser. No. 09/235,771 (PCT/US99/0138).

Embodiments for the synthesis of 5(S) thioamidomethyloxazolidinone derivatives are shown below in Scheme 2.

Scheme 2. General syntheses of 5-(S)-thioamidomethyloxazolidinone derivatives.

1. Synthesis from 5-(S)-aminomethyl derivatives and dithiocarboxylates :

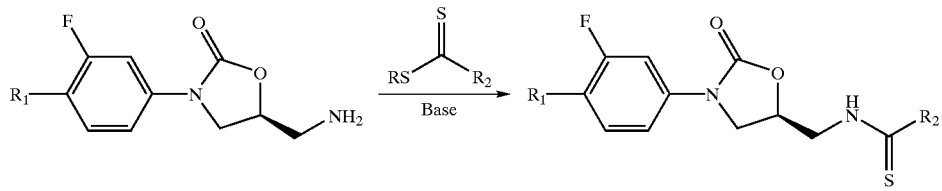

2. Synthesis from 5-(S)-amidomethyl derivatives and Lawesson reagent:

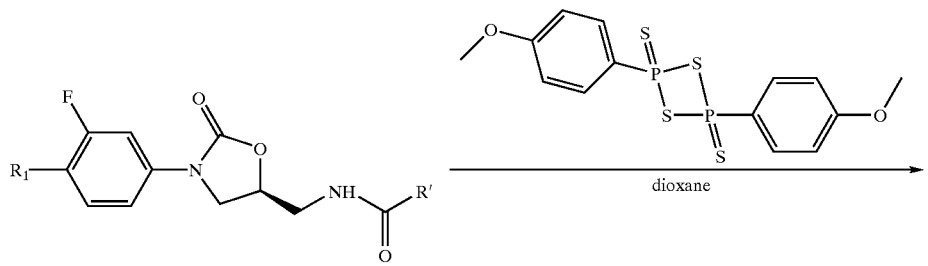

-continued

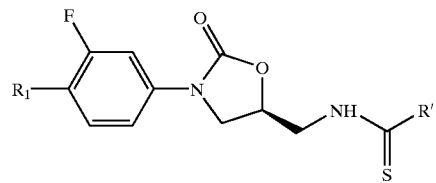

3. Synthesis from 5-(S)-amidomethyl derivatives and thionation reagent s:

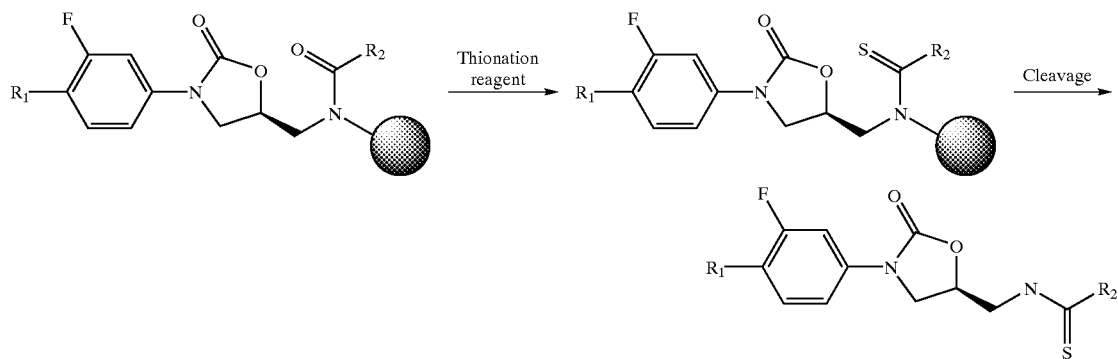

Thionation reagent = Lawesson, Davy, Yokoyama, or Belleau reagents, $P_4S_{10}$, $Na_2P_4S_{11}$, or $Na_2P_4S_{10}O$, or other reagent capable of converting the amide group into thioamide group, and $R_1$ and $R_2$ are independently substituents such as alkyl and heteroalkyl.

Exemplay synthetic routes are also shown generally below in Scheme 2a.

Scheme 2a. General syntheses of 5-(S)-thioamidomethyloxazolidinone de rivatives.

1. Synthesis from 5-(S)-aminomethyl derivatives and dithiocarboxylates :

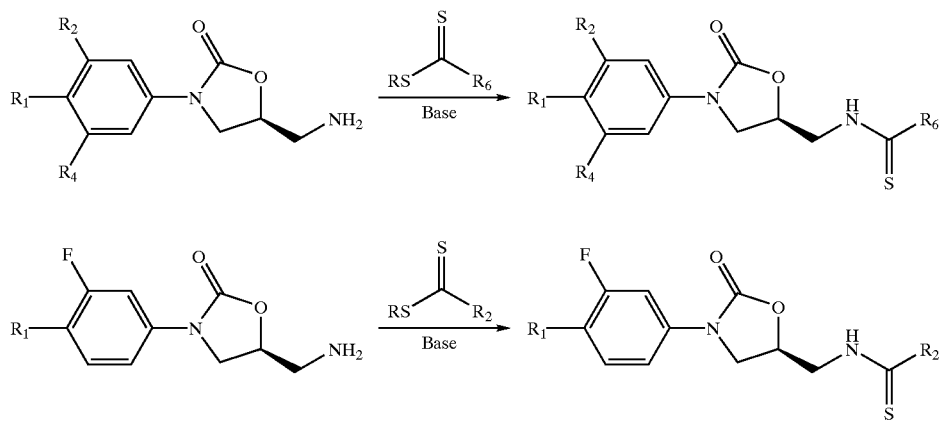

2. Synthesis from 5-(S)-amidomethyl derivatives and Lawesson reagent:

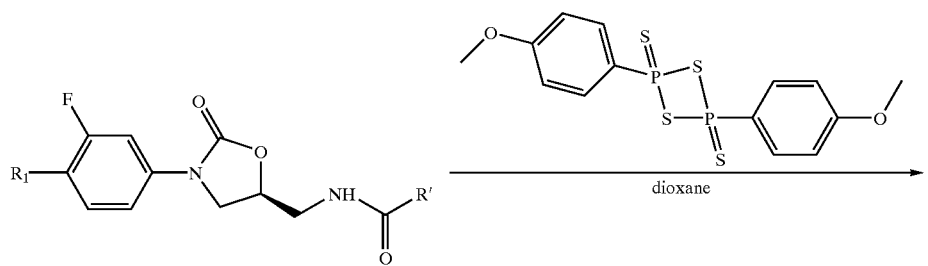

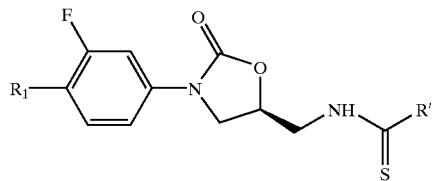

3. Synthesis from 5-(S)-amidomethyl derivatives and thionation reagent s:

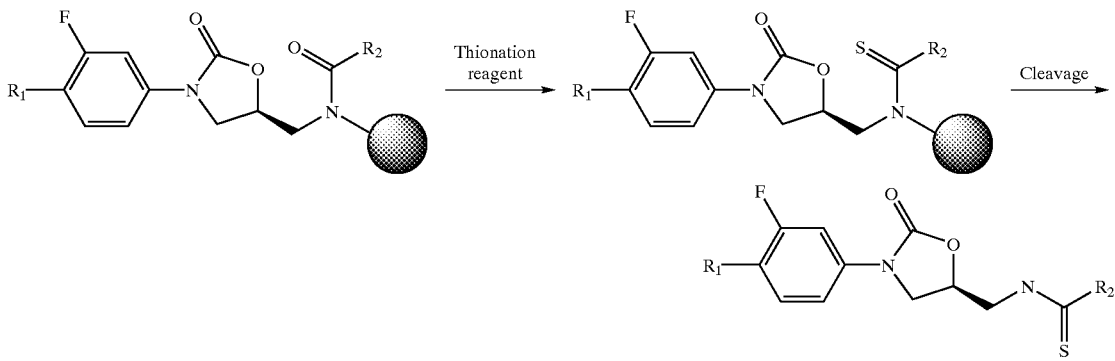

Thionation reagent = Lawesson, Davy, Yokoyama, or Belleau reagents, $P_4S_{10}$, $Na_2P_4S_{11}$, or $Na_2P_4S_{10}O$, or alike reagent capable of converting the amide group into thioamide group. $R_{1-6}$, and $R'$ are independently selected substituents such as alkyl and heteroalkyl.

In one embodiment, 5-(S)-thioamidomethyloxazolidinone derivatives can be produced in solution by transformation of 5-(S)-aminomethyloxazolidinones with various electrophilic reagents capable of thioacylation of the primary amine groups.

In another embodiment, 5-(S)-aminomethyloxazolidinones can be first acylated to produce 5-(S)-amidomethyloxazolidinones intermediates. The latter then can be converted into desired thioamides using various thionation reagents, such as Lawesson, Dayy, Yokayama or Belleau reagents. For a decription of Lawesson reagents, se M. P. Cava, M. I. Levinson, *Tetrahedron* (1985), 41:5061. For a description of Davy reagents, see H. Davy, *Chem. Commun.*, (1982) p. 457. For a description of Yokoyama reagents, see M. Yokoyama et al., *Synthesis,* (1984) p. 827. For a description of Belleau reagents, see *Tetrahedron Lett.,* 1983, 24, p. 3815. For a decription of Heimgartner reagents, see P. Wipf, C. Jenny, and H. Heimgartner. *Helv. Chim. Acta,* (1987) 70, p. 1001. For a description of $P_4S_{10}$ and related reagents, see E. Campaigne, *The Chemistry of the Carbonyl Group* (Ed. S. Patai), Chap. 17. Interscience, New York, 1966. For a description of $Na_2P_4S_{11}$ reagents, see D. Brillon., *Synth. Commun.*, (1992) 22, p. 1397. For a description of $Na_2P_4S_{10}O$ reagents, see D. Brillon, *Synth. Commun.*, (1990), 20, p. 3085. The disclosure of these and all other publications referred to herein are incorporated herein by reference in their entirety.

In another embodiment, the thionation step can be performed on immobilized 5-(S)-amidomethyloxazolidinones. Resulting products can be released from supports using chemical cleavage reagents (such as TFA for acid-cleavable resins) or light (when photocleavable linker resin is employed).

Another illustrative example of a general synthetic scheme for the synthesis of substituted aminomethyl-3-aryloxazolidinone compounds is shown below in scheme 3a.

Scheme 3a
Examples for general syntheses of substituted 5-(S)-aminomethyl-3-aryloxazolidinone derivatives

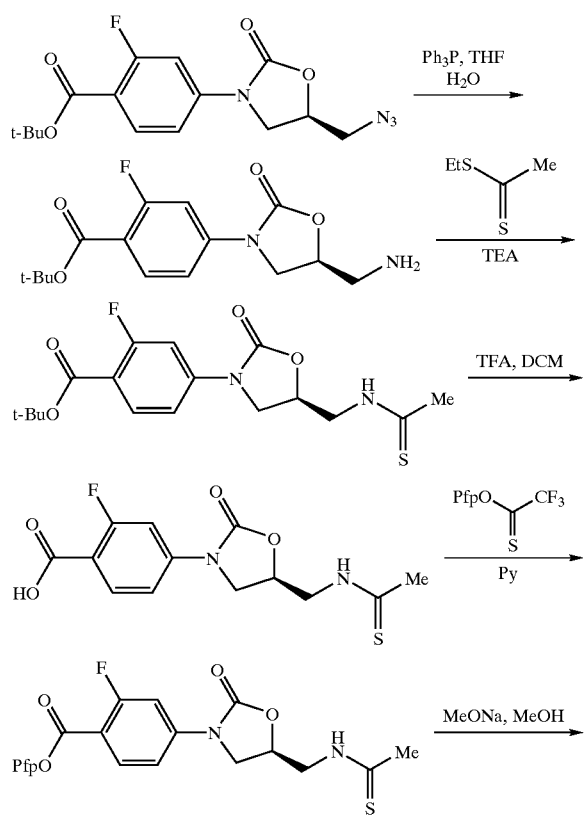

-continued

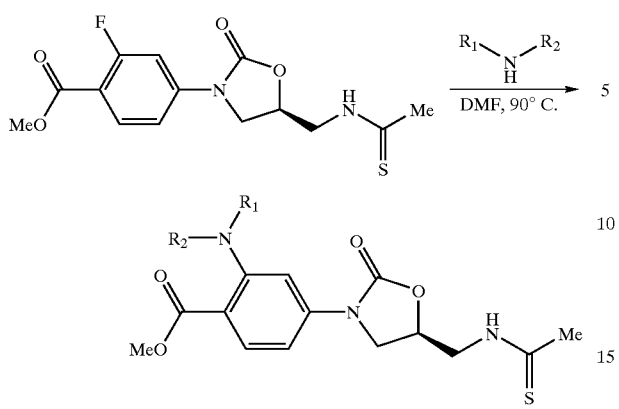

R1, and R2 are independently substituents such as alkyl and heteroalkyl

In another embodiment, either tethered 5-(S)-thioamidomethyloxazolidinone derivatives or their 5-(S)-amidomethyl-oxazolidinone precursors can be subjected to various chemical transformations on solid supports prior to the cleavage or transformation into thioamides analogously to such reaction s of immobilized 5-(S)-amidomethyloxazolidinones described in U.S. patent application Ser. No. 09/235,771).

In another example, oxazolidinone compounds are synthesized in part on a solid support as shown below in scheme 3:

Scheme 3
A general synthesis of an array of 5-(thiocarbonyl)aminoooxazolidinines involving (i) immobilization of amine reagents on polymeric supports, (ii) functionalizations in position 4 of the aromatic group, (iii) cleavage of 5-aminomethyl-oxazolidinones from resin, and (iv) functionalization with appropriate thioacylating reagent(s)

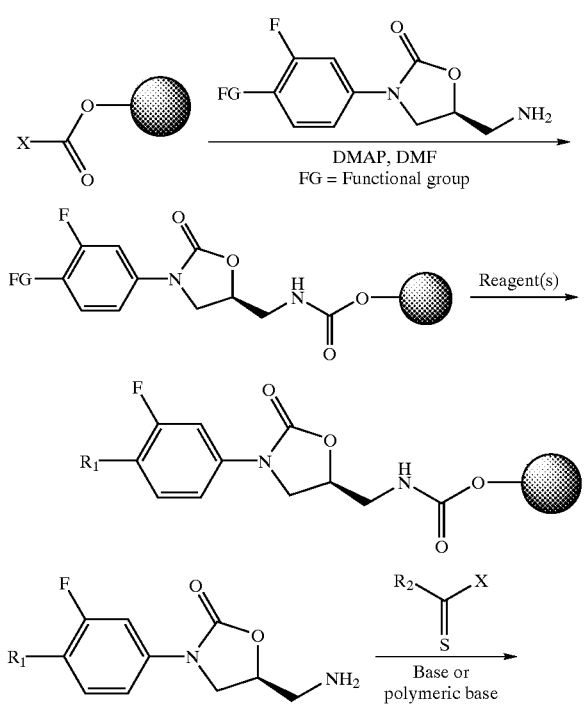

-continued

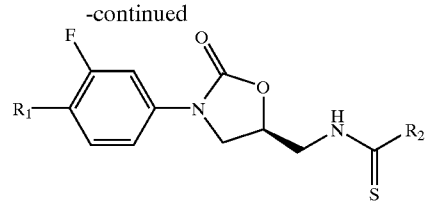

$R_2$ = a substituent such as alkyl, aryl, heteroatom, NHR, OR, SR; S = SR′, OR′, Cl, benzotriazole, imidazole, or other leaving group, where $R_1$, $R_2$, R, and R′ are independently substituents such as alkyl or heteroalkyl.

5-(S)-aminomethyloxazolidinone derivatives can be immobilized on polymeric supports to produce reactive tethered intermediates. The latter can be further modified in various part of the molecule using functional group transformations to derive the desired structures. These can be cleaved from a support in form of the novel 5-(S)-aminomethyloxazolidinone structures that can be converted into thioamides using various thioacylating reagents as described for a solution synthesis of such compounds.

In another embodiment, oxazolidinone compounds can be synthesized as shown below in Scheme 4.

Scheme 4
An example of oxazolidinone thioamide synthesis involving (i) immobilization of amine oxazolidinone reagent on solid supports, (ii) cleavage of the 5-aminomethyloxazolidinone intermediate from resin, and (iii) thioacylation to provide 5-thioamidomethyloxazolidinone

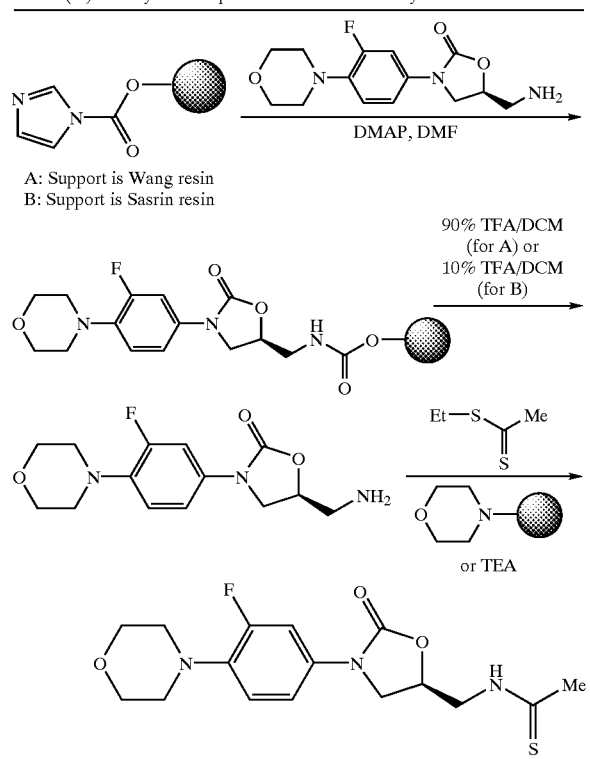

A: Support is Wang resin
B: Support is Sasrin resin

For example, 5-(S)-aminomethyloxazolidinone derivatives can be reacted with Wang or Sasrin imidazole carbamate resins to produce oxazolidinones immobilized via acid cleavable carbamate linkage. 5-(S)-Aminomethyloxazolidinone can be released from such supports by TFA treatment and further converted into thioamide derivatives via thioacylation with alkyl dithiocarboxylate reagents in solution.

Scheme 5 below shows an example of the synthesis of an oxazolidinone thioamide using a polymeric thioacylating agent:

Scheme 5. An example of oxazolidinone thioamide synthesis involving cleavage of the 5-aminomethyloxazolidinone intermediate from resin and thioacylation with a polymeric thioacylating reagent to provide 5-thioamidomethyloxazolidinone.

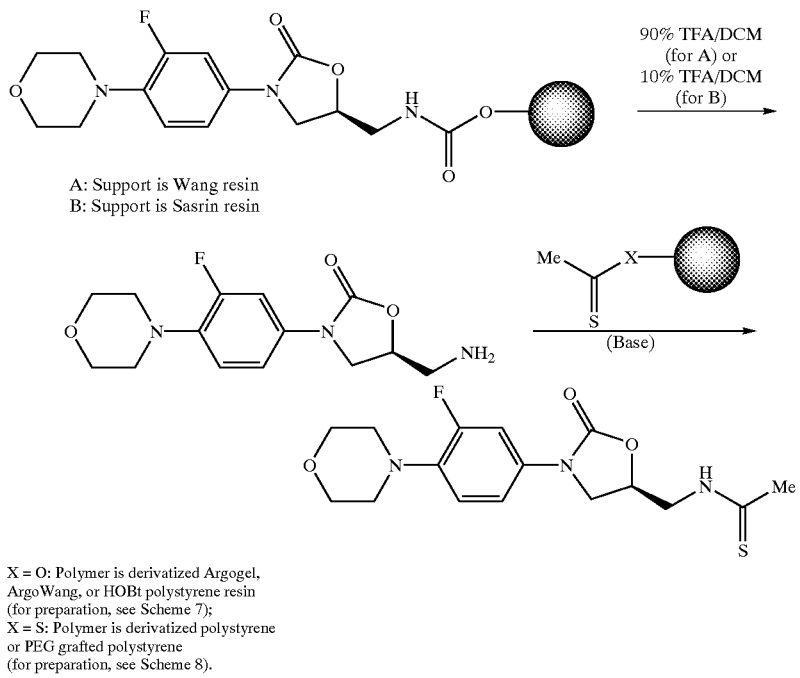

A: Support is Wang resin
B: Support is Sasrin resin

X = O: Polymer is derivatized Argogel, ArgoWang, or HOBt polystyrene resin (for preparation, see Scheme 7);
X = S: Polymer is derivatized polystyrene or PEG grafted polystyrene (for preparation, see Scheme 8).

Transformation of 5-(S)-aminomethyloxazolidinones into thioamides can be effected using polymeric thioacylating reagents to provide an advantage of easy products separation. In one embodiment, this can be performed using dithiocarboxylate resin derivatives.

In one embodiment, polymeric thioacylating reagents can be produced by thioacylation of suitable OH, SH, or NH-functionalized supports with reagents capable of this transformation in solution phase, as shown below in Scheme 6.

Scheme 6. Examples for general syntheses of the polymeric thioacylating reagents via thioacylation of appropriate OH, SH, or NH-derivatized polymers.

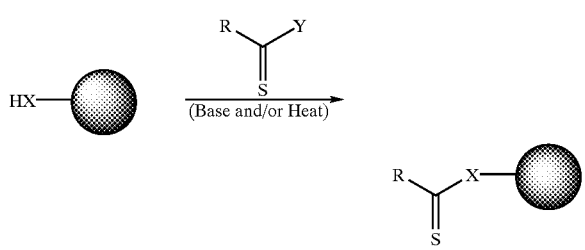

X = O, S, heterocyclic NH group, (RO)NR' group, or other functionality.
Polymer is polystyrene, polyethyleneglycol (PEG), PEG grafted polystyrene, or alike resin.
R = Substituents such as alkyl, aryl, heteroalkyl, NHR', OR', SR'; and R' is a substituent.
Y = Cl, SR, OR, imidazole, benzotriazole, nitrobenzotriazole, benzimidazolone, (fluoro or nitro)benzimidazolone, or alike leaving group.

In another embodiment, polymeric thioacylating reagents can be produced by alkylation of dithiocarboxylate salts with a polymeric support comprising reactive alkylation functionalities, such as benzyl or alkyl chloride groups, as shown below in Scheme 7.

Scheme 7. Examples for general syntheses of the polymeric thioacylating reagents via reaction of dithiocarboxylates with polymer alkylating agents.

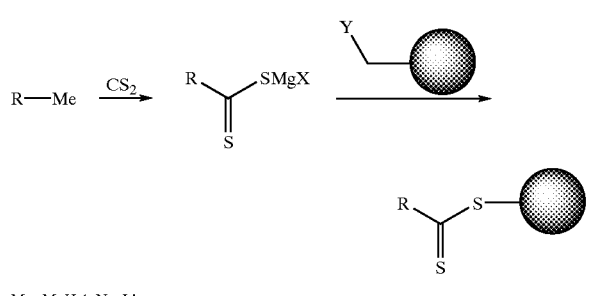

M = MgHal, Na, Li, or other metal group
Y = Cl, Br, TsO, or other leaving group.
Polymer is polystyrene, polyethyleneglycol (PEG), PEG grafted polystyrene, or alike resin.
R is a substituent such as alkyl.

Scheme 8 below shows the general synthesis of polymeric thioacylating agents.

Scheme 8. Example for general syntheses of the polymeric thioacylating reagents via thionation of appropriate acylated NH-functionalized polymers.

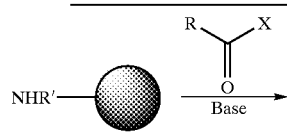

29
-continued

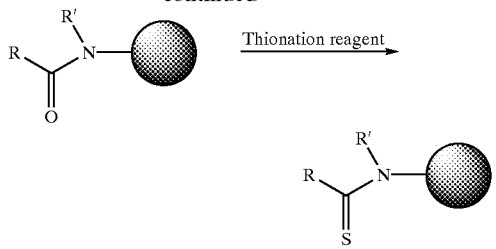
Thionation reagent →

NHR' = heterocyclic NH group, such as imidazole,benzotriazole, nitrobenzotriazole,benzimidazolone,(fluoro or nitro)benzimidazolone; (RO)NR' group; or other acidic NH functionality.
Polymer is polystyrene, polyethyleneglycol (PEG), PEG grafted polystyrene, or alike resin.
R = is a substituent such as alkyl, aryl, heteroatom, or heteroalkyl
X = Cl, SR, OR, or other leaving group.

Thioacylating polymeric reagents can be produced by transformation of suitable immobilized amides into thioamides using thionation reagents, such as Lawesson, Davy, Yokoyama, or Belleau reagents, phosphorus pentasulfide and other chemicals capable of the transformation. Resulting thioamides comprising a thiocarbonyl group attached to an electron withdrawing nitrogen atom can be used to thioacylate the primary amine group of 5-(S)-aminomethyloxazolidinone derivatives.

An example of the use of polymeric thioacylating reagents in the preparation of oxazolidinones is shown below in Scheme 9.

Scheme 9. Example for syntheses of polymeric thioacylating reagents used in preparation of 5-thioamidomethyloxazolidinones.

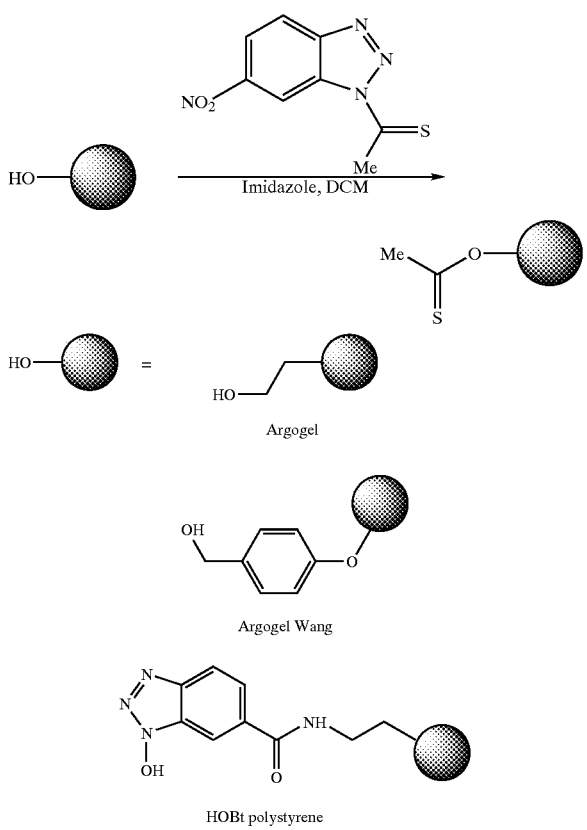

Polymeric thioacylating reagents can be produced by thioacylation of an alcohol group functionalized polymers.

30

Resulting thionoester resin can be used to effect the conversion of 5-(S)-aminomethyloxazolidinones into reactive thioamide derivatives.

Examples of the use of polymeric thioacylating agents for the preparation of oxazolidinones is shown below in Scheme 10.

Scheme 10. Example for preparation of polymeric thioacylating reagents used for preparation of 5-thioamidomethyloxazolidinones.

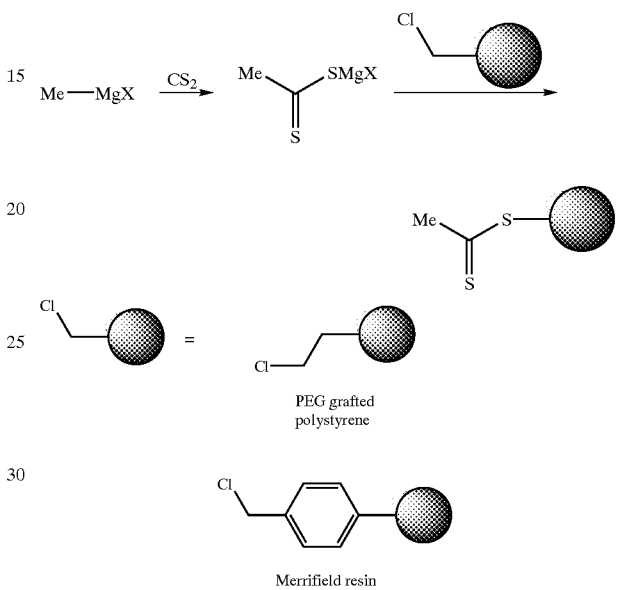

The thioacylating reagent can be made from Grignard reagents, carbon disulfide, and chloroalkyl functionalized polymer, such as polyethyleneglycol grafted polystyrene, cross-linked divinylbenzene-polystyrene, and other similar polymeric materials.

As shown in Scheme 11 below, in another embodiment, 5-(S)-aminomethyloxazolidinone derivatives can be immobilized on a polymeric support(s) with a suitable linker functionality (such as aldehyde or benzyl chloride type group) and then acylated to produce immobilized 5-(S)-amidomethyloxazolidinone derivatives. These tethered amide intermediates can be converted into thioamides on a solid phase using thionation reagents capable of transformation of a secondary amine group into thioamide functionality. Resulting products can be released from the support using chemical or photo-cleavage depending on the nature of the linker group.

Scheme 11. Example for a general synthesis of 5-thioamidomethyloxazolidinone synthesis involving a thionation of oxazolidinone amide derivative attached to a polymeric carrier.

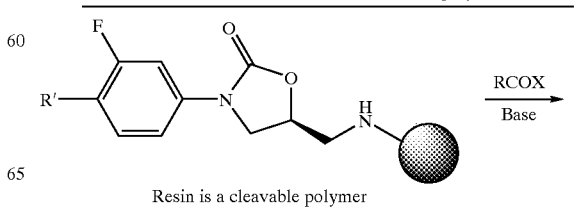

Resin is a cleavable polymer

-continued

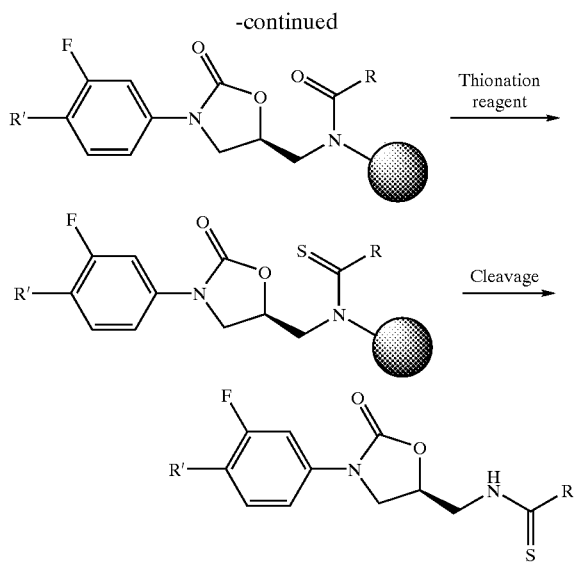

Thionation reagent = Lawesson, Davy, Yokoyama, or Belleau reagents, $P_4S_{10}$, $Na_2P_4S_{11}$, or $Na_2P_4S_{10}O$, or other reagent capable of converting the amide group into thioamide functionality. R and R' are substituents such as alkyl, aryl, heteroalkyl.

For example, as shown below in Scheme 12, BAL linker immobilized 5-(S)-amidomethyl-3-[4'-morpholino-3'-fluoro]phenyloxazolidine-2-one was converted into respective thioamide using Lawesson reagent in dioxane. The resulting product was released from the support using TFA cleavage.

Solid Supports

The solid phase synthesis of the compositions provided herein in one embodiment is performed on a solid support. "Solid support" includes an insoluble substrate that has been appropriately derivatized such that a chemical module can be attached to the surface of the substrate through standard chemical methods. Solid supports include, but are not limited to, beads and particles such as peptide synthesis resins. For example, see Merrifield (1963) *J. Am. Chem. Soc.* 85:2149–2154; U.S. Pat. No. 4,631,211; and Geysen et al. (1984) *Proc. Natl. Acad. Sci. USA* 81:3998–4002.

Solid supports can consist of many materials, limited primarily by the capacity of the material to be functionalized through synthetic methods. Examples of such materials include, but are not limited to, polymers, plastics, resins, polysaccharides, silicon or silica based materials, carbon, metals, inorganic glasses and membranes. Preferred resins include Sasrin resin (a polystyrene resin available from Bachem Bioscience, Switzerland), Wang resin or p-nitrophenylcarbonate Wang resin (PNP resin, Novabiochem), and TentaGel S AC, TentaGel PHB, or TentaGel S $NH_2$ resin (polystyrene-polyethylene glycol copolymer resins available from Rapp Polymere, Tubingen, Germany or from Perseptive, Boston).

The solid support can be purchased with suitable functionality already present such that a chemical module can be attached to the support surface (e.g., Novabiochem, Bachem Bioscience, Rapp Polymere). Alternatively, the solid support can be chemically modified such that a chemical module can be attached to the support surface. Grant (1992) *Synthetic Peptides. A User's Guide*, W. H. Freeman and Co.; and Herinkens et al. (1996) *Tetrahedron* 52:4527–4554. One of ordinary skill in the art will understand that the choice of

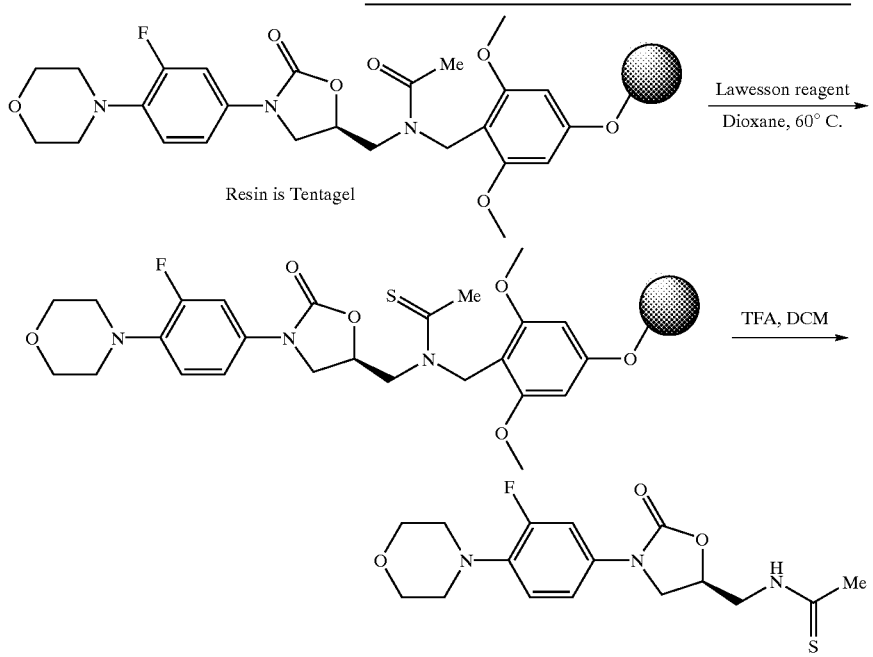

Scheme 12. An example for 5-thioamidomethyloxazolidinone synthesis involving a thionation of oxazolidinone amide derivative attached to a polymeric carrier.

As will be appreciated by those skilled in the art, using these and other methods disclosed herein, based on the teachings of the specification, the oxazolidinones disclosed herein can be readily synthesized.

functionality used for attaching a molecule to the solid support will depend on the nature of the compound to be synthesized and the type of solid support. Examples of functionality present on the solid support that can be used to attach a chemical module include, but are not limited to, alkyl or aryl halides, aldehydes, alcohols, carbonates, ketones, amines, sulfides, carboxyl groups, aldehyde groups and sulfonyl groups.

The functional group on the solid support that permits the attachment of a chemical module is, for example, an alcohol, an amine, an aldehyde, a carbonate, or a diol group. Gordon et al. (1994) *J. Med. Chem.* 37:1385–1401; and Hermkens et al. (1996) *Tetrahedron* 52:4527–4554.

For making certain combinatorial libraries, one can purchase a solid support with an existing, protected chemical module already attached. An example of such a support is FmocGly Sasrin, which is commercially available from Bachem. Typically, however, the first step of the combinatorial library synthesis is the attachment of a chemical module to the solid support through the existing functionality on the support surface. Examples of chemical reactions that can be used to attach a chemical module to the support include, but are not limited to, nucleophilic displacement of a halide or other leaving group, etherification of an alcohol, esterification of an alcohol, amidation of an amine, carbamation of an amine, reductive amination of a carbonyl compound, acetalization of an aldehyde and ketalization of a ketone. Hermkens et al. (1996) *Tetrahedron* 52:4527–4554.

The reaction used to attach the chemical module to the solid support is, for example, a carbamation of an amine, a reductive amination of a carbonyl compound or a nucleophilic displacement of a halide or other leaving group. For example, see Hermkens et al. (1996).

For the attachment of certain chemical modules to the solid support, it may be necessary to mask functionality that is not involved in the attachment process, but that is incompatible with the mode of attachment. A non-limiting example of this type of process is the esterification of an alcohol functionalized solid support, using a hydroxyl-substituted carboxylic acid as the coupling partner. Prior to the esterification reaction, the hydroxyl group of the carboxylic acid would be "protected" through alkylation, silylation, acetylation, or through another method known to one of skill in the art. Strategies for the use of masking or protecting groups have been well-described in the art, such as in Green (1985) *Protecting Groups in Organic Synthesis,* Wiley.

Methods of Compound Cleavage from a Solid Support

The cleavage of oxazolidinones from a solid support to produce the corresponding "free" compounds can be accomplished using a variety of methods. For example, a compound can be photolytically cleaved from a solid support (Wang et al. (1976) *J. Org. Chem.* 41:3258; Rich et al. (1975) *J. Am. Chem. Soc.* 97:1575–1579), and through nucleophilic attack (U.S. Pat. No. 5,549,974), or through hydrolysis (Hutchins et al. (1994) *Tetrahedron Lett.* 35:4055–4058). The cleavage of compounds from a solid support to produce soluble compounds is accomplished, for example, using hydrolytic conditions, such as through the addition of trifluoroacetic acid.

Screening

The oxazolidinone compounds can be screened to identify bioactive molecules with different biological activities using methods available in the art. The bioactive molecules, for example, can possess activity against a cellular target, including but not limited to enzymes and receptors, or a microorganism. A target cellular ligand or microorganism is one that is known or believed to be of importance in the etiology or progression of a disease. Examples of disease states for which compounds can be screened for biological activity include, but are not limited to, inflammation, infection, hypertension, central nervous system disorders, and cardiovascular disorders.

In one embodiment of screening, for example, an enzyme solution can be mixed with a solution of the compound(s) under conditions favorable to enzyme-ligand binding. See Bush et al. (1993) *Antimicrobial Agents and Chemotherapy* 37:851–858; and Daub et al. (1989) *Biochemistry* 27:3701–3708. Specific binding of compounds to the enzyme can be detected, for instance, by any of the numerous enzyme inhibition assays which are well known in the art. Compounds which are bound to the enzyme are separated readily from compounds which remain free in solution by applying the solution to a suitable separation material such as Sephadex G-25 gel filtration column. Free enzyme and enzyme-ligand complexes pass through the column quickly, while free compounds are retarded in their progress through the column. The mixture of enzyme-ligand complex and free enzyme is then treated with a suitable denaturing agent, such as guanidinium hydrochloride or urea, to cause release of the ligand from the enzyme. The solution is then injected onto an HPLC column (for example, a Vydac C-4 reverse-phase column, and eluted with a gradient of water and acetonitrile ranging from 0% acetonitrile to 80% acetonitrile). Diode array detection provides discrimination of the compounds of the combinatorial library from the enzyme. The compound peaks are then collected and subjected to mass spectrometry for identification.

Finding a compound that inhibits an enzyme is performed most readily with free compound in solution. The compounds can also be screened while still bound to a resin used for synthesis; in some applications, this may be the preferable mode of finding compounds with the desired characteristics. For example, if a compound that binds to a specific antibody is desired, the resin-bound library of compounds is contacted with an antibody solution under conditions favoring a stable antibody-compound-resin complex. A fluorescently labeled second antibody that binds to the constant region of the first antibody is then contacted with the antibody-compound-resin complex. This allows identification of a specific bead as carrying the compound recognized by the first antibody binding site. The bead is then physically removed from the resin mixture and subjected to mass spectral analysis. If the synthesis is conducted in a manner such that only one compound is likely to be synthesized on a particular bead, then the binding compound has been identified. If the synthesis is carried out so that many compounds are present on a single bead, the information derived from analysis can be utilized to narrow the synthetic choices for the next round of synthesis and identification.

The enzyme, antibody, or receptor target need not be in solution. Antibody or enzyme can be immobilized on a column. The compound(s) is then passed over the column, resulting in the retention of strongly binding compounds on the column after weaker-binding and non-binding compounds are washed away. The column is then washed under conditions that dissociate protein-ligand binding, which removes the compounds retained in the initial step. These compounds are then analyzed, and synthesized separately in quantity for further testing. Similarly, cells bearing surface receptors are contacted with a solution of compounds. The cells bearing bound compounds are readily separated from the solution containing non-binding compounds. The cells are then washed with a solution which dissociates the bound ligand from the cell surface receptor. Again, the cells are separated from the solution, and the solution analyzed.

The compounds also may be assayed for P-lactamase inhibition using methods available in the art.

Pharmaceutical Compositions

The present invention also provides pharmaceutical compositions which comprise a bioactive oxazolidinone compound or a salt such as a pharmaceutically acceptable salt thereof and optionally a pharmaceutically acceptable carrier. The compositions include those in a form adapted for oral, topical or parenteral use and can be used for the treatment of bacterial infection in mammals including humans.

The compounds, such as antibiotic compounds, also referred to herein as antimicrobial compounds, according to the invention can be formulated for administration in any convenient way for use in human or veterinary medicine, by analogy with other bioactive agents such as antibiotics. Such methods are known in the art and are not described in detail herein.

The composition can be formulated for administration by any route known in the art, such as subdermal, by-inhalation, oral, topical or parenteral. The compositions may be in any form known in the art, including but not limited to tablets, capsules, powders, granules, lozenges, creams or liquid preparations, such as oral or sterile parenteral solutions or suspensions.

The topical formulations of the present invention can be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present, for example, from about 1% up to about 98% of the formulation. For example, they may form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods will known in normal pharmaceutical practice.

Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavoring or coloring agents.

For parenteral administration, fluid unit dosage forms are prepared utilizing the compound and a sterile vehicle, water being preferred. The compound, depending on the vehicle and concentration used, can be either suspended or dissolved in the vehicle or other suitable solvent. In preparing solutions, the compound can be dissolved in water for injection and filter sterilized before filling into a suitable vial or ampoule and sealing. Advantageously, agents such as a local anesthetic preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain, for example, from about 0.1% by weight, e.g., from about 10–60% by weight, of the active material, depending on the method of administration. Where the compositions comprise dosage units, each unit will contain, for example, from about 50–500 mg of the active ingredient. The dosage as employed for adult human treatment will range, for example, from about 100 to 3000 mg per day, for instance 1500 mg per day depending on the route and frequency of administration. Such a dosage corresponds to about 1.5 to 50 mg/kg per day. Suitably the dosage is, for example, from about 5 to 20 mg/kg per day.

Pharmaceutical Applications

The oxazolidinones disclosed herein can be used in a variety of pharmaceutical applications. In one embodiment, the compounds may be used as antimicrobial agents for the treatment of infectious disorders that are caused by microbial agents, such as bacteria.

In one embodiment, compositions, for treating or preventing infectious disorders are provided, comprising an oxazolidone compound as disclosed herein in combination with a pharmaceutically acceptable carrier.

In another embodiment, there is provided a dosage amount of an oxazolidinone as disclosed herein in an effective amount for the treatment, prevention or alleviation of a disorder, such as an infectious disorder.

Oxazolidinones can be screened for activity against different microbial agents and appropriate dosages may be determined using methods available in the art.

The compounds may be used to treat a subject to treat, prevent, or reduce the severity of an infection. Subjects include animals, plants, blood products, cultures and surfaces such as those of medical or research equipment, such as glass, needles and tubing.

In one embodiment, methods of treating or preventing an infectious disorder in a subject, such as a human or other animal subject, are provided, by administering an effective amount of an oxazolidinone as disclosed herein to the subject. In one embodiment, the compound is administered in a pharmaceutically acceptable form optionally in a pharmaceutically acceptable carrier. As used herein, an "infectious disorder" is any disorder characterized by the presence of a microbial infection, such as bacterial infections. Such infectious disorders include, for example central nervous system infections, external ear infections, infections of the middle ear, such as acute otitis media, infections of the cranial sinuses, eye infections, infections of the oral cavity, such as infections of the teeth, gums and mucosa, upper respiratory tract infections, lower respiratory tract infections, genitourinary infections, gastrointestinal infections, gynecological infections, septicemia, bone and joint infections, skin and skin structure infections, bacterial endocarditis, burns, antibacterial prophylaxis of surgery, and antibacterial prophylaxis in immunosuppressed patients, such as patients receiving cancer chemotherapy, or organ transplant patients. The compounds and compositions comprising the compounds can be administered by routes such as topically, locally or systemically. Systemic application includes any method of introducing the compound into the tissues of the body, e.g., intrathecal, epidural, intramuscular, transdermal, intravenous, intraperitoneal, subcutaneous, sublingual, rectal, and oral administration. The specific dosage of antimicrobial to be administered, as well as the duration of treatment, may be adjusted as needed.

The compounds of the invention may be used for the treatment or prevention of infectious disorders caused by a variety of bacterial organisms. Examples include Gram positive and Gram negative aerobic and anaerobic bacteria, including Staphylococci, for example *S. aureus;* Enterococci, for example *E. faecalis;* Streptococci, for example *S. pneumoniae;* Haemophilus, for example *H. influenza;* Moraxella, for example *M. catarrhalis;* and Escherichia, for example *E. coli.* Other examples include Mycobacteria, for example *M. tuberculosis;* intercellular microbes, for example Chlamydia and Rickettsiae; and Mycoplasma, for example *M. pneumoniae.*

The following examples are provided to illustrate but not limit the claimed invention.

EXAMPLES

Abbreviations: ACN, acetonitrile; CDI, carbonyldiimidazole; DIEA, diethylisopropylamine; DCM, dichloromethane; DIC, diisopropyldiimide; DMF, dimethylformamide; HATU, O-(7-azabenzotriazol-1-yl)-1,1,3,3-bis(tetramethylene)-uronium hexafluorophosphate; NMM, N-methyl morpholine; mCPBA, m-chloro-peroxybenzoic acid; TFA, trifluoroacetic acid; THF, tetrahydrofuran; TMOF, trimethylorthoformate; PTLC, preparative thin layer chromatography.

General. Reagents were obtained from Aldrich (St. Louis, Mo.), Sigma (St. Louis, Mo.), Bachem Biosciences, Rapp Polymere, Perseptive, and Novabiochem, and used without further purification. The resin Tentagel S NTi was purchased from Rapp Polymere. Concentration of solutions after workup was performed by reduced pressure rotary evaporation, or using the Savant's SpeedVac instrument. Reactions with moisture-sensitive reagents were performed under nitrogen atmosphere.

Mass-spectra were obtained using ESI technique. HTLC analysis and purification were performed using Beckman System Gold R®; detection at 220 nm. Analytical EPLC was performed on YMC 5 micron C18 (4.6 mm×50 mm) reverse phase column (gradient from 100% of the aq. 0.1% TFA to 100% of 0.1% TFA in MECN over 6 min', flow rate 2.0 mL/min). Preparative TLC was performed using EM silica gel 60 $F_{254}$ plates (20×20 cm, thickness 2 min).

NMR spectra were obtained on a Varian Gemini 300 MHz instrument with $CDCl_3$ as solvent, unless otherwise noted. 1H NMR spectra were reported as follows: chemical shift relative to tetramethylsilane (0.00 ppm), multiplicity (s=singlet, d=doublet, t=triplet, q=quartet, m=multiplet, b=broad), coupling, and integration.

Example 1
General Methods for Preparation of 5-(S)-Thioamidomethyloxazolidinones A. Synthesis from 5-(S)-Aminomethyloxazolidinone Derivatives and Ethyl Dithioacetate.

A solution of an appropriate 5-(S)-aminomethyloxazolidinone derivative (1.0 mmol) and ethyl dithioacetate (0.130 ml, 1.13 mmol) with triethylamine (0.215 ml, 1.54 mmol) in dichloromethane was stirred at room temperature overnight. The reaction mixture was concentrated under vacuum and the residue purified by PTLC (MeOH-DCM mixtures) or crystallization from appropriate solvent.

B. Synthesis from 5-(S)-Amidomethyloxazolidinone Derivatives and Lawesson Reagent.

A mixture of an appropriate 5-(S)-amidomethyloxazolidinone derivative (0.3 mmol) and Lawesson's reagent (0.0654 g, 0.15 mmol) in dioxane (3 ml) was stirred and heated at 65° C. for 2 hours. The solution was concentrated under vacuum and the crude product purified by PTLC.

C. Solid Phase Synthesis from Immobilized 5-(S)-Amidomethyl-oxazolidinone Derivatives.

A mixture of an appropriate 5-(S)-amidomethyloxazolidinone immobilized derivative (such as described in U.S. patent application Ser. No. 09/235,771 and in PCT US99/01318) (0.1 mmol) and an appropriate thionation reagent (0.1–1.0 mmol) in dioxane or THF (2–10 mL) Lawesson's reagent (0.15 was stirred at 0–65° C. for 2–10 hours (preferably, at 0–25° C. for $P_4D_{10}$, $Na_2P_4S_{11}$ or $Na_2P_4S_{10}O$, and at 40–65° C. for Lawesson, Belleau, or Davy reagents). The resin was washed liberally with DMF, DCM, MeOH, and dried under vacuum. The product was cleaved from support with 10% TFA in DCM (2–4 mL, r.t., 2 h), solvents removed under vacuum, and the crude product purified by PTLC.

Example 2
Synthesis of Intermediates

2-Fluoro-4-nitrobenzoic Acid

Concentrated sulfuric acid (32 ml) was added carefully with stirring to a solution of 2-fluoro-4-nitrotoluene (16.5 g, 0.106 mol) in acetic acid (200 ml). The mixture was warmed up to 95 ° C., and solution of chromium trioxide (37.1 g, 0.371 mol) in water (32 ml) was added dropwise with stirring over 2 h. The mixture was heated with stirring for another 30 minutes, allowed to cool down to r.t., and poured into water (1000 ml). The product was extracted with diethyl ether (3×200 ml). Combined ether layers were washed with water and evaporated to dryness. The residue was dissolved in 10% aqueous potassium carbonate and washed with ether. The aqueous layer was acidified with con. HCl, and the resulting white precipitate filtered and dried (16.3 g, 83%), m.p. 174–177° C.

tert-Butyl 2-fluoro-4-nitrobenzoate

Thionyl chloride (45 ml, 0.62 mol) was added to 2-fluoro-4-nitrobenzoic acid (23.0 g, 0.124 mol), and the mixture was stirred under reflux for 2 h. Solvent was removed under vacuum, and the residue thoroughly dried under vacuum to give crystalline acid chloride (25.2 g, 99%). The acid chloride was dissolved in tetrahydrofuran (150 ml) under nitrogen, and 1M lithium tert-butoxide in tetrahydrofuran (136 ml, 0.136 mol) was added dropwise with stirring at room temperature. The mixture was stirred overnight, diluted with water (300 ml) and extracted with ether. The ether layer was washed with saturated aqueous sodium bicarbonate, brine, and dried ($MgSO_4$). Solvent was removed under vacuum to gave the product as a white crystalline solid (24.2 g, 81%); mp 81–82 ° C.

tert-Butyl-2-fluoro-4-aminobenzoate

Tert-butyl 2-fluoro-4-nitrobenzoate (24.2 g, 0.100 mol) was added to a warm (95° C.) solution of ammonium chloride (53.5 g, 1.00 mol), dissolved in ethanol (300 ml) and water (150 ml). Iron powder (325 mesh, 16.8 g, 0.300 mol) was added with stirring in small portions over about 1 h. The reaction mixture was stirred and heated at 95° C. for another 30 minutes and then filtered while still warm. The filter cake was washed thoroughly with excess ethanol. The filtrate and washings were diluted with water (1 L) and extracted with ether (3×150 ml). Combined ether extracts were washed with water and brine, dried (MgSO$_4$), and evaporated to give the product as an off-white solid (21.1 g, 98%); mp 100–101° C.

O-Benzyl-N-(3-fluoro-4-butoxycarbonylphenyl) carbamate

Benzyl chloroformate (15.9 ml, 0.112 mol) was added dropwise with stirring to a mixture of tert-butyl-2-fluoro-4-aminobenzoate (21.5 g, 0.102 mol) and pyridine (16.5 ml, 0.204 mol) in dichloromethane (200 ml) at 0° C. The reaction mixture was stirred for 30 minutes at 0° C., allowed to warm up to room temperature, and then poured into water (about 300 ml). The organic layer was separated, washed with water, brine and dried (MgSO$_4$). Evaporation gave a white solid, which was washed with hexane and dried under vacuum to afford the product (32.8 g, 93%); mp 117–118° C.

5-(R)-Hydroxymethyl-3-[4'-tert-butoxycarbonyl-3'-fluorophenyl]oxazolidine-2-one

1M Lithium bis(trimethylsilyl)amide in tetrahydrofuran (104 ml, 0.104 mol) was added dropwise with stirring at −78° C. to a solution of O-benzyl-N-(3-fluoro-4-butoxycarbonylphenyl)-carbamate (32.8 g, 0.0948 mol) in tetrahydrofuran (150 ml). The mixture was stirred at −78° C. for 1 hour, and then (R)-glycidyl butyrate (15.0 g, 0.104 mol) was added dropwise with stirring. The mixture was allowed to warm to room temperature overnight, and was then quenched with saturated aqueous ammonium chloride (100 ml). The mixture was extracted with ethyl acetate, and the combined organic layers washed with water, brine, and dried (MgSO$_4$). Solvent was removed under vacuum, and the crude product purified by silica gel column chromatography (eluent: 30% ethyl acetate in hexanes) to afford the product as a white solid (20.0 g, 68%); mp 148–149° C.

5-(S)-Azidomethyl-3-[4'-tert-butoxycarbonyl-3'-fluorophenyl]oxazolidine-2-one

Methanesulfonyl chloride (2.61 ml, 0.0337 mol) was added dropwise with stirring to a solution of 5-(R)-hydroxymethyl-3-[4'-tert-butoxycarbonyl-3'-fluorophenyl] oxazolidine-2-one (10.0 g, 0.0321 mol) and triethylamine (6.71 ml, 0.0482 mol) in dichloromethane (150 ml) at 0° C. over about 15 minutes. The reaction mixture was allowed to warm up to room temperature and then poured into water. The organic layer was separated, washed with water, saturated aq. NaHCO$_3$, brine, and dried (MgSO$_4$). Solvent was removed under vacuum to afford the mesylate intermediate as an oil (11.6 g, 99%). A mixture of the mesylate (13.4 g, 0.0370 mol) and sodium azide (12.0 g, 0.185 mol) in DMF (130 ml) was heated with stirring at 75° C. for 12 h. The reaction mixture was cooled to room temperature, diluted with water (300 ml), and extracted with ethyl acetate (3×100 ml). Combined organic layers were washed with water and brine, dried (MgSO$_4$) and evaporated. The residue was washed with diethyl ether to give the pure azide as a white solid (9.76 g, 90.5%); mp 91–92° C.

Example 3

5-(S)-Azidomethyl-3-[4'-chlorocarbonyl-3'-fluorophenyl]oxazolidine-2-one

60% TFA in DCM (5 mL) was added to 5-(S)-azidomethyl-3-[4'-tert-butoxycarbonyl-3'-fluorophenyl] oxazolidine-2-one (0.336 g, 1 mmol), and the solution kept at r.t. for 1 h. Solvents were removed in vacuo to afford 5-(S)-azidomethyl-3-[4'-carboxy-3'-fluorophenyl-) oxazolidine-2-one dried (0.280 g, 99%). N-Trimethylsilyl-N,N-diethylamine (0.23 mL, 1.2 mmol) was added to above product in dry dichloromethane (3 mL) under nitrogen atmosphere, and the solution stirred for 15 min. Solvents and excess reagent were removed in vacuo, and residue dissolved in dichloromethane (4 mL). The solution was cooled to about 0° C., and oxalyl chloride (1.5 mmol, 0.13 mL) was added dropwise, followed by catalytic N,N-dimethylformamide (about 0.01 mL). The mixture was alllowed to warm up to r.t. (room temperature), and stirred at r.t. for another 2 h. Solvents were removed in vacuo to afford the product as a white solid. Yield 0.292 g (98%).

5-(S)-Azidomethyl-3-[4-(6"-chloropyridine-3"-yl) aminocarbonyl-3'-fluoro-phenyl]oxazolidine-2-one 5-(S)-Azidomethyl-3-[4'-chlorocarbonyl-3'-fluorophenyl]oxazolidine-2-one (0.298 g, 1.0 mmol) was added to a solution of 5-amino-2-chloropyridine (0.129 g, 1.0 mmol) in 20% pyridine in THF (2 mL), and the mixture stirred at r.t overnight. Solvent was removed unde vacuum, and the residue triturated with water. Resulting crude product was washed with 3% aq. citric acid, 2% aq. sodium bicarbonate, water, ethyl ether, and dried under vacuum (yield 0.357 g, 91%; $^1$H NMR).

5-(S)-Aminomethyl-3-[4'-(6"-chloropyridine-3"-yl) aminocarbonyl-3'-fluoro-phenyl]oxazolidine-2-one 5-(S)-Azidomethyl-3-[4'-(6"-chloropyridine-3"-yl) aminocarbonyl-3'-fluoro-phenyl]oxazolidine-2-one (0.35 g, 0.896 mmol) and triphenylphosphine (0.235 g, 0.896 mmol) in THF (10 mL) was stirred at r.t. for 4 h and then at 40° C. for 2 h. Water (0.5 mL) was added, and the mixture stirred at 40° C. overnight. Solvents were removed in vacuo, and resulting crude product washed with ethanol and diethyl ether. Yield 0.215 g (66%). $^1$H NMR. MS (n/z): [M+H]$^+$= 365.

5-(S)-Thioacetamidomethyl-3-[4'-(6"-chloropyridine-3"-yl)aminocarbonyl-3'-fluoro-phenyl]oxazolidine-2-one

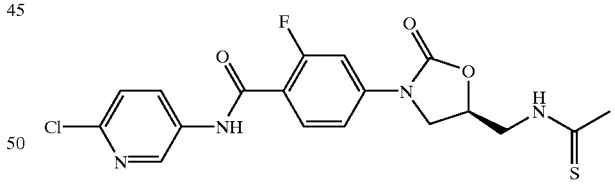

This compound was prepared analogously to Method A (Example 1) above from 5-(S)-aminomethyl-3-[4'-(2"-chloropyridine-5"-yl)aminocarbonyl-3'-fluorophenyl] oxazolidine-2-one (0.125 g, 0.343 mmol) and ethyl dithioacetate. The crude product purified by PTLC (10% MeOH in DCM). Yield 0.035 g (24%). MS (m/z): [M+H]$^+$=421.

Example 4

5-(S)-Azidomethyl-3-[4'-(5"-trifluoromethylpyridine-2"-yl)aminocarbonyl-3'-fluorophenyl]oxazolidine-2-one This compound was prepared analogously to the synthesis of 5-(S)-azidomethyl-3-[4'-(6"-chloropyridine-3"-yl)

aminocarbonyl-3'-fluorophenyl]oxazolidine-2-one from 2-amino-5-trifluoromethylpyridine (0.100 g, 0.62 mmol) and 5-(S)-azidomethyl-3-[4'-chlorocarbonyl-3'-fluorophenyl]oxazolidine-2-one (0.184 g, 0.62 mmol). Yield 0.11 g (42%). MS (m/z): [M+H]⁺=425.

5-(S)-Aminomethyl-3-[4'-(5"-trifluoromethylpyridine-2"-yl)aminocarbonyl-3'-fluorophenyl]oxazolidine-2-one Preparation was analogous to the synthesis of 5-(S)-aminomethyl-3-[4'-(6"-chloropyridine-3"-yl)aminocarbonyl-3'-fluorophenyl]oxazolidine-2-one from 5-(S)-azidomethyl-3-[4'-(5"-trifluoromethylpyridine-2"-yl)aminocarbonyl-3'-fluorophenyl]oxazolidine-2-one (0.100 g, 0.235 mmol) and triphenylphosphine (0.068 g, 0.259 mmol). Yield 0.087 g (93%). MS (m/z): [M+H]⁺=399.

5-(S)-Thioacetamidomethyl-3-[4'-(5"-trifluoromethylpyridine-2"-yl)amino-carbonyl-3'-fluorophenyl]oxazolidine-2-one

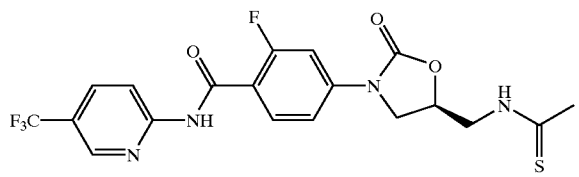

This compound was prepared analogously to the Method A of General Methods for Preparation of 5-(S)-Thioamidomethyloxazolidinones (Example 1) from 5-(S)-aminomethyl-3-[4'-(5"-trifluoromethylpyridine-2"-yl)aminocarbonyl-3'-fluorophenyl]oxazolidine-2-one (0.070 g, 0.176 mmol) and ethyl dithioacetate. The crude product was purified by PTLC (10% MeOH in DCM). Yield 0.020 g (20%). MS (m/z): [M+H]⁺=457.

Example 5

5-(S)-Azidomethyl-3-[4'-(5"-trifluoromethyl-1",3",4"-thiadiazole-2"-yl)amino-carbonyl-3'-fluorophenyl]oxazolidine-2-one Prepared analogously to the synthesis of 5-(S)-azidomethyl-3-[4'-(6"-chloropyridine-3"-yl)aminocarbonyl-3'-fluorophenyl]oxazolidine-2-one from 2-amino-5-trifluoromethyl-1,3,4-thiadiazole (0.100 g, 0.59 mmol) and 5-(S)-azidomethyl-3-[4'-chlorocarbonyl-3'-fluorophenyl] oxazolidine-2-one (0.176 g, 0.59 mmol). Yield 0.093 g (36%). MS (m/z): [M+H]⁺=432.

5-(S)-Aminomethyl-3-[4'-(5"-trifluoromethyl-1",3",4"-thiadiazole-2"-yl)ami-nocarbonyl-3'-fluorophenyl]oxazolidine-2-one Prepared analogously to the synthesis of 5-(S)-aminomethyl-3-[4'-(6"-chloropyridine-3"-yl)aminocarbonyl-3'-fluorophenyl]oxazolidine-2-one from 5-(S)-azidomethyl-3-[4'-(5"-trifluoromethyl-1",3",4"-thiadiazole-2"-yl)amino-carbonyl-3'-fluorophenyl] oxazolidine-2-one (0.090 g, 0.209 mmol) and triphenylphosphine (0.055 g, 0.209 mmol). Yield 0.010 g (12%). MS (m/z): [M+H]⁺=406.

5-(S)-Thioacetamidomethyl-3-[4'-(5"-trifluoromethyl-1",3",4"-thiadiazole-2"-yl) aminocarbonyl-3'-fluorophenyl]oxazolidine-2-one

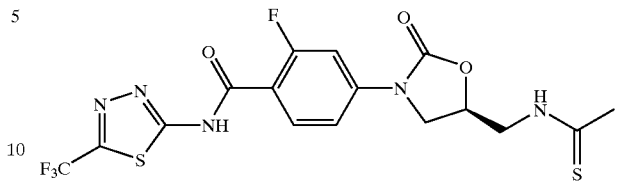

Prepared analogously to the Method A of General Methods for Preparation of 5-(S)-Thioamidomethyloxazolidinones (Example 1) from 5-(S)-aminomethyl-3-[4'-(5"-trifluoromethyl-1",3",4"-thiadiazole-2"-yl)aminocarbonyl-3'-fluorophenyl]-oxazolidine-2-one (0.010 g, 0.0247 mmol; prepared analogously to U.S. patent Ser. No. 09/235,771) and ethyl dithioacetate. The crude product purified by PTLC (10% MeOH in DCM). Yield 0.0035 g (31%). MS (m/z): [M+H]⁺=464.

Example 6

3-Fluoro-4-thiocyanoaniline

N-Bromosuccinimide (1.76 g, 9.89 mmol) and potassium thiocyanate (1.75 g, 18.0 mmol) in methanol (30 ml) were stirred for 15 minutes at room temperature. The reaction mixture was cooled to 0° C., and 3-fluoroaniline (1.00 g, 9.0 mmol) was added dropwise. The mixture was stirred at 0° C. for 2 h. Solvent was removed under vacuum, and the residue was washed with dichloromethane. The mixture was filtered to remove succinimide by-product, and the solution was washed with water, brine, and dried (MgSO₄). Solvent was removed under vacuum to afford the desired product as a colorless oil. Yield 1.45 g (96%).

O-Benzyl-N-[3-fluoro-4-(thiocyano)phenyl] carbamate

Benzyl chloroformate (1.87 ml, 13.1 mmol) was added to a mixture of 3-fluoro-4-thiocyanoaniline (2.00 g, 11.9 mmol) and pyridine (2.12 ml, 26.2 mmol) in dichloromethane (30 ml) at 0° C. The mixture was stirred for 30 minutes at 0° C., allowed to warm to room temperature, and then poured into water. The organic layer was separated, washed with brine, and dried (MgSO₄). Solvent was removed under vacuum. The crude product was washed with ether-hexanes and dried under vacuum to afford the desired product. Yield 3.64 g (92%); m.p. 74–75° C.

O-Benzyl-N-[3-fluoro-4-(triphenylmethylthio) phenyl]carbamate

Sodium sulfide nonahydrate (0.794 g, 3.31 mmol) in water (3 ml) was added dropwise at room temperature to a solution of O-benzyl-N-[3-fluoro-4-(thiocyano)phenyl] carbamate (1.00 g, 3.31 mmol) in ethanol (10 ml). The reaction mixture was stirred at room temperature for 30 minutes, and then triphenylmethyl bromide (1.07 g, 3.31 mol) in 1,4-dioxane (5 ml) was added dropwise. The reaction was stirred overnight. Organic solvent was removed under vacuum, and the residue taken up in ethyl acetate. The solution was washed with water, brine, and dried (MgSO₄). Solvent was removed under vacuum, and the crude product purified by silica gel column chromatography (eluent: 10% ethyl acetate in hexanes) to give the desired compound as a white solid. Yield 1.10 g, (64%); mp 152–153° C.

5-(R)-Hydroxymethyl-3-[4'-triphenylmethylthio-3'-fluorophenyl]oxazolidine-2-one

1M Lithium bis(trimethylsilyl)amide in tetrahydrofuran (54 mL, 69.9 mmol) was added dropwise with stirring at −78° C. to a solution of O-benzyl-N-[3-fluoro-4-(triphenylmethylthio)phenyl]carbamate (33.0 g, 63.5 mmol) in tetrahydrofuran (250 ml). The mixture was stirred at −78° C. for 1 hour, and then (R)-glycidyl butyrate (11.0 g, 76.2 mmol) was added dropwise with stirring. The mixture was allowed to warm up to room temperature overnight, and then quenched with saturated aq. ammonium chloride (125 ml). The mixture was extracted with ethyl acetate, and combined organic layers washed with water, brine, and dried (MgSO$_4$). Solvent was removed under vacuum, and the crude product purified by silica gel column chromatography (gradient from 30% to 75% of ethyl acetate in hexane) to afford the product. TLC: R$_f$ 0.2 (ethyl acetate-hexanes 1:1). MS 486 [M+H]$^+$.

5-(S)-Azidomethyl-3-[4'-triphenylmethylthio-3'-fluorophenyl]oxazolidine-2-one

Methanesulfonyl chloride (3.91 mL, 50.6 mmol) was added dropwise with stirring to a solution of 5-(R)-hydroxymethyl-3-[4'-triphenylmethylthio-3'-fluorophenyl]oxazolidine-2-one (23.4 g, 48.2 mmol) and triethylamine (10.1 mL, 73.8 mmol) in dichloromethane (200 mL) at 0° C. over about 10 minutes. The reaction mixture was allowed to warm up to room temperature and then poured into water. The organic layer was separated, washed with water, saturated aq. NaHCO$_3$, brine, and dried (MgSO$_4$). Solvent is removed under vacuum to afford the mesylate intermediate as an oil (27.2 g, 99%). The mesylate (27.2 g, 48.2 mmol) and sodium azide (15.7 g, 241.0 mmol) in DMF (150 ml) was heated with stirring at 70° C. for 12 h. The reaction mixture was cooled to r.t., diluted with water (750 mL), and extracted with ethyl acetate. Combined organic layers were washed with water, brine, and dried (MgSO$_4$). Solvent was removed under vacuum and the crude product purified by silica gel column chromatography (eluent: 30% ethyl acetate in hexanes) to afford the azide product as a white solid. Yield 18.1 g (73%). M.p. 77–79° C.

5-(S)-Aminomethyl-3-[4'-triiphenylmethylthio-3'-fluorophenyl]oxazolidine-2-one

Triphenylphosphine (2.82 g, 10.8 mmol) was added portionwise to a solution of 5-(S)-azidomethyl-3-[4'-triphenylmethylthio-3'-fluorophenyl]oxazolidine-2-one (5.00 g, 9.79 mmol) in THF (40 mL), and the mixture stirred for 2 h at r.t. Water (1.41 mL, 78.3 mmol) was added, and the mixture heated at 40° C. overnight. Solvent was removed under vacuum, and the oily residue purified by column chromatography (eluent: DCM, then 10% MeOH in DCM). Yield 3.56 g (75%). MS (m/z): [M+H]$^+$=485.

5-(S)-Acetamidomethyl-3-[4'-triphenylmethylthio-3'-fluorophenyl]oxazolidine-2-one Triphenylphosphine (2.82 g, 10.8 mmol) was added portionwise to a solution of 5-(S)-azidomethyl-3-[4'-triphenylmethylthio-3'-fluorophenyl]oxazolidine-2-one (5.00 g, 9.79 mmol) in THF (40 mL), and the mixture stirred for 2 h at room temperature. Water (1.41 mL, 78.3 mmol) was added, and the mixture heated at 40° C. overnight. Solvent was removed under vacuum, and the oily residue dissolved in dichloromethane (50 mL). Acetic anhydride (4.62 ml, 49.0 mmol) and pyridine (7.92 ml, 97.9 mmol) were added, and the mixture stirred for 8 h at r.t. Solvent was removed under vacuum and the crude product purified by silica gel flash column chromatography (eluent: 30% ethyl acetate in hexanes) to give the product as a foam (4.98 g, 97%); MS (m/z): [M+H]$^+$=527.

General Procedure for Preparation of 5-(S)-(N-Acylaminomethyl)-3-[4'-(substituted)thio-3'-fluorophenyl]oxazolidine-2-ones 5% TFA and 2.5% triisopropylsilane in dichloromethane (2.0 mL) was added to 5-(S)-acetamidomethyl-3-[4'-triphenylmethylthio-3'-fluorophenyl]oxazoli-dine-2-one (0.10 g, 0.19 mmol), and the mixture was stirred at r.t. for 1 h. and the mixture stirred for 1 h at room temperature. Solvent was removed under vacuum, and the residue dissolved in methanol (3 mL). An appropriate alkylating or (hetero)arylating reagent (19–0.38 mmol) was added, followed by dropwise addition of 4.37 M sodium methoxide in methanol (0.087 ml, 0.380 mmol). Optionally, an organic base was used instead of sodium methoxide (e.g., tetramethylguanidine or alkylamine). The mixture was stirred at 20–70° C. for 2–24 h (typically, 2 h at r.t.). Solvent was removed under vacuum and the crude product purified by TLC (methanol-dichloromethane mixtures).

Example 7

5-(S)-Acetamidomethyl-3-[4'-(2"-chloroethyl)thio-3'-fluorophenyl]oxazolidi-ne-2-one Prepared according to the General Procedure for Preparation of 5-(S)-(N-Acylaminomethyl)-3-[4'-(substituted)thio-3'-fluorophenyl]oxazolidine-2-ones (Example 6) from 5-(S)-acetamidomethyl-3-[4'-(triphenylmethyl)thio-3'-fluorophenyl]-oxazolidine-2-one with 1-bromo-2-chloroethane (0.055 g, 0.38 mmol) in N-methylpyrrolidine-2-one (1 mL). The synthesis was performed at r.t. for 2 h. The crude product was purified by TLC (eluent: 10% methanol in dichloromethane). Yield 0.047 g (72%). MS (m/z): 347 [M+H]$^+$.

5-(S)-Thioamidomethyl-3-[4'-(2"-chloroethyl)thio-3'-fluorophenyl]oxazolidine-2-one

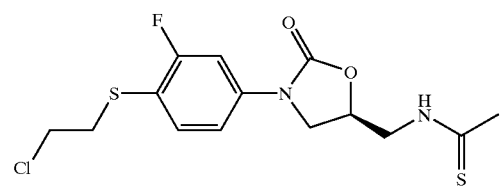

Prepared analogously to the Method B of General Methods for Preparation of 5-(S)-Thioamidomethyloxazolidinones (Example 1) from 5-(S)-acetamidomethyl-3-[4'-(2"-chloroethyl)thio-3'-fluorophenyl]oxazolidine-2-one (0.0275 g, 0.0793) and Lawesson reagent. Yield 0.027 g (94%). M.p. 134–5° C. MS (m/z): [M+H]$^+$=363.

Example 8

5-(S)-Acetamidomethyl-3-[4'-(5"-nitrothiazole-2"-yl)thio-3'-fluorophenyl]-oxazolidine-2-one Prepared according to the General Procedure for Preparation of 5-(S)-(N-Acylaminomethyl)-3-[4'-(substituted)

thio-3'-fluorophenyl]oxazolidine-2-ones (Example 6) from 5-(S)-acetamidomethyl-3-[4'-(triphenylmethyl)lthio-3'-fluorophenyl]-oxazolidine-2-one with 2-bromo-5-nitrothiazole (0.079 g, 0.38 mmol) in N-methylpyrrolidine-2-one (1 mL). The synthesis was performed at r.t. for 2 h. The crude product was purified by TLC (eluent: 10% methanol in dichloromethane). Yield 0.061 g (78%). MS (m/z): 413 [M+H]$^+$.

5-(S)-Thioamidomethyl-3-[4'-(5"-nitrothiazole-2"-yl)thio-3'-fluorophenyl]-oxazolidine-2-one

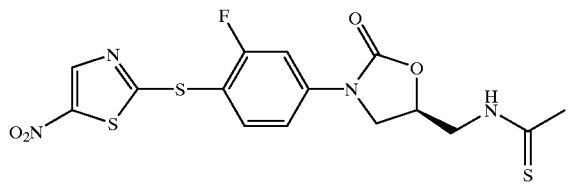

Prepared analogously to the Method B of General Methods for Preparation of 5-(S)-Thioamidomethyloxazolidinones (Example 1) from 5-(S)-acetamidomethyl-3-[4'-(5"-nitrothiazole-2"-yl)thio-3'-fluorophenyl]oxazolidine-2-one (0.028 g, 0.0736 mmol) and Lawesson reagent. Yield 0.026 g (83%). M.p. 116–7° C. MS (m/z): [M+H]$^+$=429.

Example 9

5-(S)-Acetamidomethyl-3-(4'-methylthio-3'-fluorophenyl)oxazolidine-2-one

Prepared according to the General Procedure for Preparation of 5-(S)-(N-Acylaminomethyl)-3-[4'-(substituted)thio-3'-fluorophenyl]oxazolidine-2-ones (Example 6) from 5-(S)-acetamidomethyl-3-[4'-(triphenylmethyl)lthio-3'-fluorophenyl]-oxazolidine-2-one with methyl iodide (0.05 mL, 0.81 mmol) in N-methylpyrrolidine-2-one (1 mL). The synthesis was performed at r.t. overnight, and the crude cleaved product purified by TLC (eluent: 10% methanol in dichloromethane). Yield 6.3 mg (52%). MS: 299 [M+H]$^+$.

5-(S)-Thioamidomethyl-3-[4'-methylthio-3'-fluorophenyl]-oxazolidine-2-one

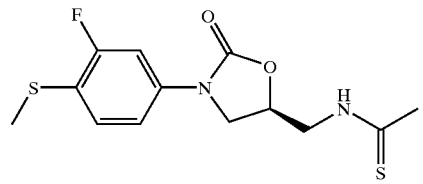

Prepared analogously to the Method B (Example 1) of General Methods for Preparation of 5-(S)-Thioamidomethyloxazolidinones from 5-(S)-acetamidomethyl-3-[4'-methylthio-3'-fluorophenyl]oxazolidine-2-one (0.100 g, 0.335 mmol) and Lawesson reagent. Yield 0.095 g (90%). M.p. 130–1° C. MS (m/z): [M+H]$^+$=315.

Example 10

5-(S)-Thioamidomethyl-3-[4'-(triphenylmethl)thio-3'-fluorophenyl]oxazoli-dine-2-one

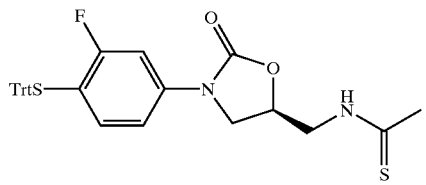

Prepared analogously to the Method A of General Methods for Preparation of 5-(S)-Thioamidomethyloxazolidinones (Example 1) from 5-(S)-aminomethyl-3-[4'-(triphenylmethyl)thio-3'-fluorophenyl]-oxazolidine-2-one (0.500 g, 1.03 mmol; prepared analogously to U.S. patent Ser. No. 09/235,771) and ethyl dithioacetate. Reaction performed in DCM overnight. Yield 0.498 g (89%). MS (m/z): [M+H]$^+$=543.

Example 11

5-(S)-Acetamidomethyl-3-[4'-(2"-hydroxyethyl)thio-3'-fluorophenyl]oxazo-lidine-2-one Prepared according to the General Procedure for Preparation of 5-(S)-(N-Acylaminomethyl)-3-[4'-(substituted)thio-3'-fluorophenyl]oxazoli-dine-2-ones (Example 6) from 5-(S)-acetamidomethyl-3-[4'-(triphenylmethyl)lthio-3'-fluorophenyl]-oxazolidine-2-one with 2-bromoethanol (0.048 g, 0.38 mmol) in N-methylpyrrolidine-2-one (1 mL). The synthesis was performed at r.t. for 2 h. The crude product was purified by TLC (eluent: 10% methanol in dichloromethane). Yield 0.045 g (72%). MS (m/z): 329 [M+H]$^+$.

5-(S)-Thioamidomethyl-3-[4'-(2"-hydroxyethyl)thio-3'-fluorophenyl]oxazo-lidine-2-one

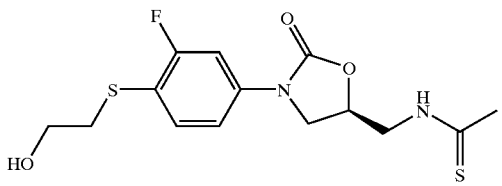

A solution of 5-(S)-thioamidomethyl-3-[4'-(triphenylmethyl)thio-3'-fluorophenyl]oxazolidine-2-one (0.100 g, 0.184 mmol) in 5% TFA and 2.5% triisopropylsilane in DCM (2 mL) is stirred at r.t. for 1 h. Solvent is removed under vacuum, and the residue is dissolved in THF (2 mL). 2-Bromoethanol (0.0196 ml, 0.276 mmol) is added followed by triethylamine (0.0513 mL, 0.368 mmol). The reaction is stirred at r.t. for 2 h, diluted with ethyl acetate, washed with water, brine, and dried Solvent is removed under vacuum and the residue is purified by PTLC (10% MeOH in DCM) to give the product.

Example 12

5-(S)-Aminomethyl-3-[4'-(tert-butoxy)carbonyl-3'-fluorophenyl]oxazolidine-2-one

A mixture of triphenylphosphine (0.521 g, 1.99 mmol) and 5-(S)-azidomethyl-3-[4'-(tert-butoxy)carbonyl-3'- fluorophenyl]]oxazolidine-2-one (0.607 g, 1.80 mmol) in THF (10 ml) was stirred at r.t. for 2 h. Water (0.259 ml, 14.4 mmol) was added, and the mixture was heated at 40° C. overnight. The reaction mixture was evaporated, the residue taken up in ethyl acetate (20 mL) and extracted with 3% aqueous citric acid (3×25 ml). Combined aqueous extracts were neutralized with saturated aqueous sodium bicarbonate and then extracted with ethyl acetate. Combined organic layers were washed with brine, dried (MgSO$_4$), and evaporated to give the product as a white solid (0.62 g, 99%). MS (m/z): [M+H]$^+$=311.

5-(S)-Thioacetamidomethyl-3-[4'-(tert-butoxy) carbonyl-3'-fluorophenyl]oxazo-lidine-2-one

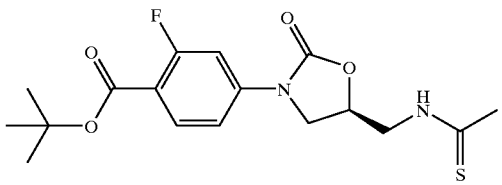

A solution of 5-(S)-aminomethyl-3-[4'-(tert-butoxy) carbonyl-3'-fluorophenyl]-oxazolidine-2-one (3.00 g, 9.66 mmol), triethylamine (1.35 ml, 19.3 mmol), and ethyl dithioacetate (1.22 ml, 10.6 mmol) in DMF (8 mL) was stirred at room temperature for 3 hours. The reaction mixture was diluted with ethyl acetate (50 ml), washed with 3% aqueous citric acid (3×30 mL), saturated aqueous sodium bicarbonate (30 mL), brine, and dried (MgSO$_4$). Evaporation afforded the product as a white solid (3.00 g, 84%). MS (m/z): [M+H]$^+$=369.

Example 13

5-(S)-Thioacetamidomethyl-3-(4'-carboxy-3'-fluorophenyl)oxazolidine-2-one

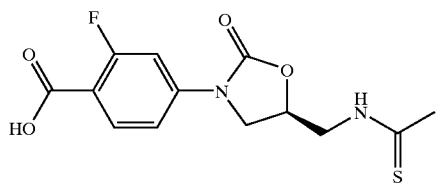

5-(S)-Thioamidomethyl-3-[4'-(tert-butoxy)carbonyl-3'-fluorophenyl]oxazolidi-ne-2-one (2.50 g, 6.79 mmol) was dissolved in 50% TFA/DCM (30 mL) and stirred for 1 h at r.t. Solvents were removed under vacuum to afford the product as a white solid (2.12 g, 99%). M.p. 180–2° C. MS (m/z): [M+H]$^+$=313.

Example 14

5-(S)-Thioacetamidomethyl-3-[4'-(thiazole-2"-yl) aminocarbonyl-3'-fluorophenyl]oxazolidine-2-one

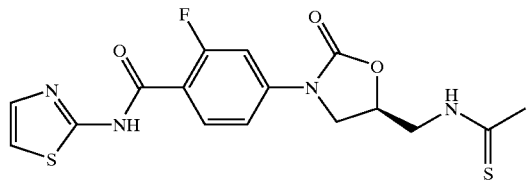

A solution of 5-(S)-thioacetamidomethyl-3-(4'-carboxy-3'-fluorophenyl)-oxazolidine-2-one (0.037 g, 0.120 mmol), O-(7-azabenzotriazol-1-yl)-N,N,N',N'-tetramethyluronium hexafluorophosphate (0.0502 g, 0.132 mmol), and DIEA (0.0627 mL, 0.360 mmol) in DMF (0.5 mL) was stirred at r.t. for 20 minutes. 2-Aminothiazole (0.0120 mg, 0.120 mmol) was added and the mixture stirred overnight. Most of the solvent was removed under vacuum and the residue purified by preparative HPLC to give pure product as a white solid (0.020 mg, 42%). MS (m/z): [M+H]$^+$=395.

Example 15

5-(S)-Thioacetamidomethyl-3-[4'-(thiazole-2"-yl) aminothiocarbonyl-3'-fluorophenyl]oxazolidine-2-one

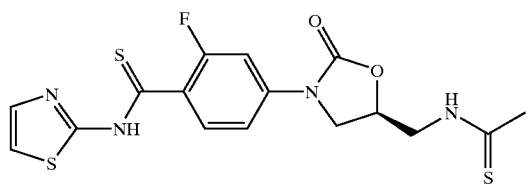

A mixture of 5-(S)-thioacetamidomethyl-3-[4'-(thiazole-2"-yl)aminocarbonyl-3'-fluorophenyl]oxazolidine-2-one (0.040 g, 0.10 mmol) and Lawesson reagent (0.020 g, 0.05 mmol) in dioxane (0.5 mL) is stirred at 60–70° C. overnight. Solvent is removed under vacuum and the crude product is purified by PTLC.

Example 16

5-(S)-Thioacetamidomethyl-3-[4'-(pentafluorophenoxy)carbonyl-3'-fluorophenyl]oxazolidine-2-one

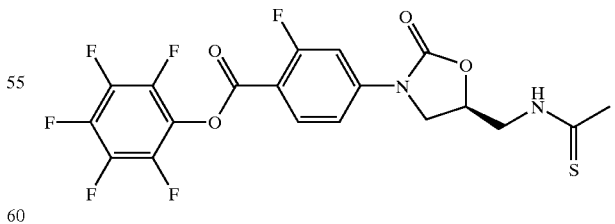

A mixture of 5-(S)-thioamidomethyl-3-(4'-carboxy-3'-fluorophenyl)oxazol-idine-2-one (0.650 g, 2.08 mmol), pyridine (0.673 ml, 8.32 mmol), and pentafluorophenyl trifluoroacetate (0.429 ml, 2.50 mmol) in DMF (8 mL) was stirred at r.t. for 3 h. The reaction mixture was diluted with ethyl acetate, washed with 3% aqueous citric acid, brine, and dried (MgSO₄). Evaporation afforded the pure product as a white solid (0.90 g, 90%). M.p. 163–4° C. ; MS (m/z): [M+H]⁺= 479.

Example 17

5-(S)-Thioacetamidomethyl-3-[4'-(N-methylamino) carbonyl-3'-fluorophenyl]-oxazolidine-2-one

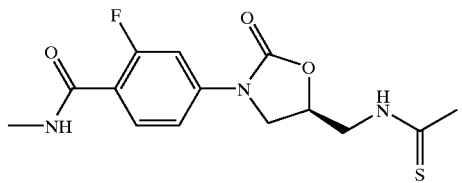

A solution of 5-(S)-thioacetamidomethyl-3-[4'-(pentafluorophenoxy)carbonyl-3'-fluorophe-nyl] oxazolidine-2-one (0.100 g, 0.209 mmol) in 2 M methylamine in THF (1.0 mL) was stirred at r.t. for 1 h. Solvent was removed under vacuum and the residue purified by PTLC (10% MeOH in DCM) to give the pure product as a white solid (0.054 g, 80%). M.p. 176–7° C. MS (m/z): [M+H]⁺=326.

Example 18

5-(S)-Thioacetamidomethyl-3-[4'-methoxycarbonyl-3'-fluorophenyl]oxazoli-dine-2-one

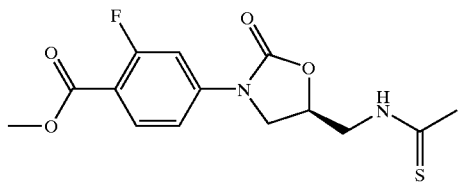

A solution of 5-(S)-thioacetamidomethyl-3-[4'-(pentafluorophenoxy)carbonyl-3'-fluorophenyl] oxazolidine-2-one (0.100 g, 0.209 mmol) and 25% sodium methoxide in methanol (0.0573 ml, 0.251 mmol) in methanol (2 mL) was stirred at r.t. for 1 h. solvent was removed under vacuum and the residue purified by PTLC (10% MeOH in DCM) to give the pure product as a white solid (0.057 g, 84%). M.p. 152–4° C. MS (m/z): [M+H]⁺=327.

Example 19

5-(S)-Thioacetamidomethyl-3-[4'-(imidazole-2"-yl) aminocarbonyl-3'-fluoro-phenyl]-oxazolidine-2-one

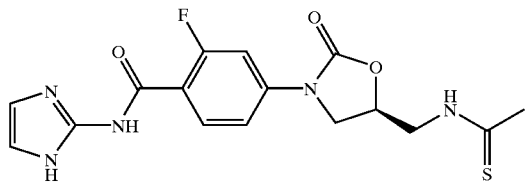

A solution of 5-(S)-thioacetamidomethyl-3-[4'-(pentafluorophenoxy)carbonyl-3'-fluorophenyl] oxazolidine-2-one (0.162 g, 0.34 mmol) and 2-aminoimidazole (0.083 mg, 1.0 mmol) in THF (5.0 mL) was stirred at r.t. for 0.5 h and then at 45° C. overnight. Solvent was removed under vacuum and the residue purified by PTLC (10% MeOH in DCM) to give the pure product as a white solid (0.058 g, 45%). MS (m/z): [M+H]⁺=378.

Example 20

5-(S)-Thioacetamidomethyl-3-[4'-(imidazole-2"-yl) thioaminocarbonyl-3'-fluorophenyl]-oxazolidine-2-one

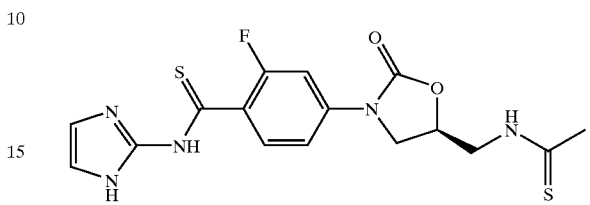

A mixture of 5-(S)-thioacetamidomethyl-3-[4'-(imidazole-2"-yl)amino-carbonyl-3'-fluorophenyl] oxazolidine-2-one (0.038 g, 0.10 mmol) and Lawesson reagent (0.020 g, 0.05 mmol) in dioxane (0.5 mL) is stirred at 60–70° C. overnight. Solvent is removed under vacuum and the crude product is purified by PTLC.

Example 21

5-(S)-Azidomethyl-3-[4'-(tert-butoxycarbonvl) amino-3'-fluorophenyl]-oxazolidine-2-one TFA (30 mL) was added to a solution of 5-(S)-azidomethyl-3-[4'-(tert-butoxy)carbonyl-3'-fluorophenyl] oxazolidine-2-one (6.72 g, 20 mmol) in DCM (20 mL), and the solution was kept at r.t. for 1 h. Solvents were removed under vacuum to afford 5-(S)-azidomethyl-3-(4'-carboxy-3'-fluorophenyl)oxazolidine-2-one. THF (75 mL) was added, followed by t-butanol (9.5 mL, 100 mmol), triethylamine (3.6 mL, 26 mmol), and diphenylphosphoryl azide (5.6 mL, 26 mmol). The mixture was stirred at r.t. under nitrogen atmosphere for 2 h, and then at 70° C. overnight. Solvent was removed under vacuum, and the residue distributed between ethyl acetate (150 mL) and aq. saturated sodium bicarbonate (100 mL). Aq. phase was washed with ethyl acetate (2×50 mL). Combined organic layers were washed with aq. saturated sodium bicarbonate, water, brine, and dried (MgSO₄). Solvent was removed under vacuum, and the product purified by silica gel column chromatography (eluent: DCM). Yield 4.1 g (58%). MS (m/z): [M+H]⁺=352.

5-(S)-Aminomethyl-3-[4'-(tert-butoxycarbonyl) amino-3'-fluorophenyl]-oxazolidine-2-one A mixture of triphenylphosphine (0.521 g, 1.99 mmol) and 5-(S)-azidomethyl-3-[4'-(tert-butoxycarbonyl)amino-3'-fluorophenyl]]oxazolidine-2-one (0.632 g, 1.80 mmol) in TBF (10 ml) was stirred at r.t. for 2 h. Water (0.259 ml, 14.4 mmol) was added, and the mixture was heated at 40° C. overnight. The reaction mixture was evaporated, the residue taken up in ethyl acetate (20 mL) and extracted with 3% aqueous citric acid (3×25 ml). Combined aqueous extracts were neutralized with saturated aqueous sodium bicarbonate and then extracted with ethyl acetate. Combined organic layers were washed with brine, dried (MgSO₄), and evaporated to give the product as a white solid (0.53 g, 90%). MS (m/z): [M+H]⁺=326.

5-(S)-Acetamidomethyl-3-[4'-amino-3'-fluorophenyl]oxazolidine-2-one

Acetic anhydride (0.15 mL) was added to a solution of 5-(S)-aminomethyl-3-[4'-(tert-butoxycarbonyl)amino-3'- fluorophenyl]oxazolidine-2-one (0.325 g, 1.0 mmol) and pyridine (0.25 mL) in DCM (4.0 mL). The mixture was stirred at r.t. for 4 h, and solvent was removed under vacuum. The resulted 5-(S)-acetamidomethyl-3-[4'-(tert-butoxycarbonyl)amino-3'-fluorophenyl]oxazoli-dine-2-one was washed with water (2×3 mL), diethyl ether (3 mL), and dried under vacuum. 50% TFA in DCM (3 mL) was added, and the mixture was kept at r.t. for 1 h. Solvents were removed under vacuum, and the residue distributed between ethyl acetate (40 mL) and saturated aq. sodium bicarbonate (20 mL). Organic layer was washed with aq. sodium bicarbonate, water, brine, dried (MgSO$_4$). Solvent was removed under vacuum to afford the product as a white solid. Yield 0.25 g (95%). MS (m/z): [M+H]$^+$=268.

5-(S)-Thioacetamidomethyl-3-[4'-amino-3'-fluorophenyl]oxazolidine-2-one

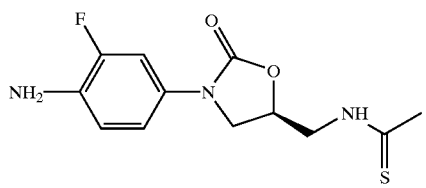

A mixture of 5-(S)-acetamidomethyl-3-[4'-amino-3'-fluorophenyl]oxazolidine-2-one. (0.100 g, 0.374 mmol) and Lawesson's reagent (0.151 g, 0.374 mol) in dioxane (2 ml) was stirred at 65° C. for 2 h. The solution was concentrated under vacuum and the residue purified by PTLC (10% methanol/dichloromethane) to give a tan solid (0.104 g, 98%); mp 137–88° C.; MS: (M+H)$^+$=284.

Example 22

5-(S)-Thioacetamidomethyl-3-[4'-acetamido-3'-fluorophenyl]oxazolidine-2-one

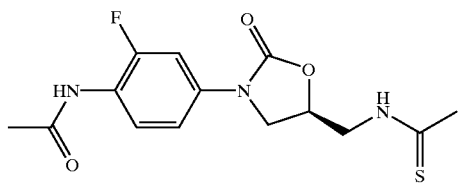

A solution of 5-(S)-thioacetamidomethyl-3-[4'-amino-3'-fluorophenyl]oxazoli-dine-2-one (0.070 g, 0.247 mmol), acetic anhydride (0.25 mL), pyridine (0.38 mL), and dichloromethane (0.75 mL) was stirred at r.t. for 4 h. Solvent was removed under vacuum and the crude prtoduct purified by PTLC (10% MeOH in DCM) to give a white solid (0.076 g, 95%). M.p. 200–1° C.; MS (m/z): (M+H)$^+$=326.

Example 23

5-(S)-Thioacetamidomethyl-3-[4'-(5"-nitro-2"-furoyl)-3'-fluorophenyl]oxazo-lidine-2-one

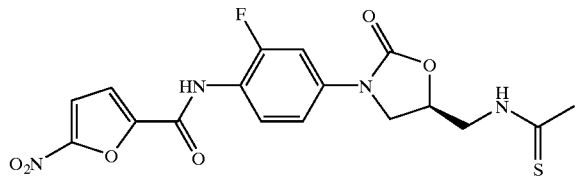

5-Nitro-2-furoyl chloride (0.069 g, 0.392 mmol) in THF (1 mL) was added dropwise to a solution of 5-(S)-thioacetamidomethyl-3-[4'-amino-3'-fluorophenyl] oxazolidine-2-one (0.111 g, 0.392 mmol) and triethylamine (0.109 ml, 0.784 mmol) in THF (3 mL) at 0° C. The mixture was stirred at r.t. for 1 h. Ethyl acetate was added, and the mixture washed with water, saturated aq. sodium bicarbonate, brine, and dried (MgSO$_4$). Solvent was removed under vacuum, and the crude material purified by PTLC (10% MeOH in DCM) to gave the pure product as an orange solid (0.079 g, 48%). M.p. 188–8° C. MS (m/z): [M+H]$^+$=423.

Example 24

5-(S)-Acetamidomethyl-3-[4'-(1",2"3"-thiadiazole-4-yl)carbonylamino-3'-fluorophenyl]oxazolidine-2-one

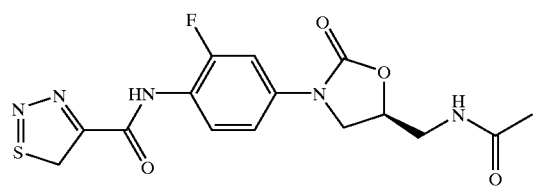

A solution of 1,2,3-thiadiazole-4-carboxylic acid (0.0731 g, 0.562 mmol), thionyl chloride (2 ml), and DMF (0.025 ml) was refluxed for 2 h. Solvent was removed under vacuum and the residue dissolved in THF (1 mL). Resulted solution was added dropwise at 0° C. to a solution of 5-(S)-acetamidomethyl-3-[4'-amino-3'-fluorophenyl] oxazolidine-2-one (0.150 g, 0.562 mmol) and triethylamine (0.157 mL, 1.12 mmol) in THF (3 mL), and the mixture stirred for 1 h at r.t. The reaction mixture was diluted with ethyl acetate and washed with water, saturated aq. sodium bicarbonate, brine, and dried (MgSO$_4$). Evaporation and purification by PTLC (10% MeOH in DCM) gave pure product as a tan solid (0.132 g, 62%); mp 233° C.; MS: (M+H)$^+$=380.

Example 25

5-(S)-Thioacetamidomethyl-3-[4'-(1",2"3"-thiadiazole-4-yl)carbonylamino-3'-fluorophenyl]oxazolidine-2-one

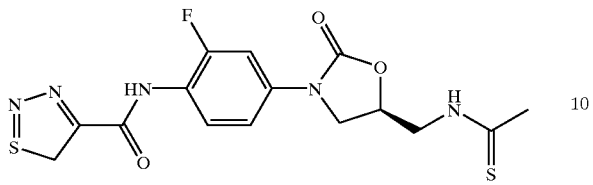

A mixture of 5-(S)-acetamidomethyl-3-[4'-(1",2"3"-thiadiazole-4-yl)carbonyl-amino-3'-fluorophenyl]oxazolidine-2-one. (0.0703 g, 0.185 mmol) and Lawesson's reagent (0.0374 g, 0.0925 mmol) in dioxane (3 mL) and sulfolane (0.02 mL) was stirred at 65° C. for 2 h. The solution was concentrated under vacuum, and the residue purified by PTLC (10% MeOH in DCM) to give a white solid (0.037 g, 51%). M.p. 203–4° C. MS (m/z): [M+H]$^+$=396.

Example 26

5-(S)-Acetamidomethyl-3-[4'-formamido-3'-fluorophenyl]oxazolidine-2-one

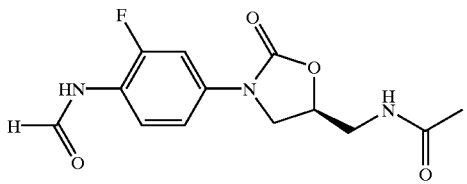

A solution of 5-(S)-acetamidomethyl-3-[4'-amino-3'-fluorophenyl]-oxazolidine-2-one (0.200 g, 0.748 mmol), p-nitrophenyl formate (0.188 g, 1.12 mmol), and 2,6-di-(tert-butyl)pyridine (0.336 mL, 1.50 mmol) in THF (4 mL) was stirred at 65° C. overnight. Solvent was removed under vacuum and the residue purified by PTLC (30% acetone in DCM) to give product as a white solid (0.188 g, 85%). M.p. 196–8° C.; MS (m/z): [M+H]$^+$=296.

5-(S)-Thioacetamidomethyl-3-[4'-formamido-3'-fluorophenyl]oxazolidine-2-one

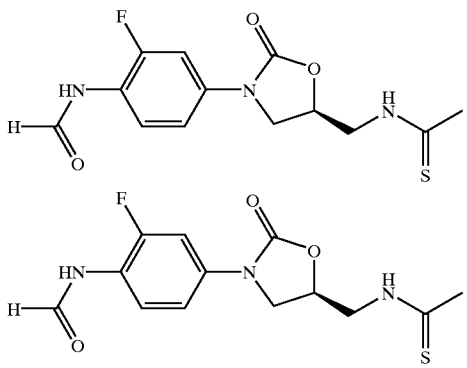

Prepared from 5-(S)-thiocetamidomethyl-3-[4'-amino-3'-fluorophenyl]oxazo-lidine-2-one (0.100 g, 0.353 mmol) as described above for the synthesis of 5-(S)-acetamidomethyl-3-[4'-formamido-3'-fluorophenyl]oxazolidine-2-one. White solid (0.0979 g, 89%). M.p. 177–8° C. MS (m/z): [M+H]$^+$=312.

Example 27

5-(S)-Acetamidomethyl-3-[4'-methylamino-3'-fluorophenyl]oxazolidine-2-one

Methyl iodide (0.86 mL, 13.8 mmol) was added dropwise to the mixture of 5-(S)-azidomethyl-3-[4'-(tert-butoxycarbonyl)amino-3'-fluorophenyl]oxazolidine-2-one (1.6 g, 4.6 mmol) and LiH (0.110 g, 13.8 mmol) in dry DMSO (15 mL). The mixture was sonicated for 1 h at r.t., and then stirred overnight. Water (200 mL) and diethyl ether (200 mL) were added, organic layer separated and aq. phase washed with ether (2×100 mL). Combined organic layers were washed with water (5×200 mL), brine, dried (MgSO$_4$). Solvent was evaporated under vacuujm to afford 5-(S)-azidomethyl-3-[4'-(tert-butoxycarbonyl)methylamino-3'-fluorophenyl]oxazolidine-2-one as a thick oil [yield 1.6 g (95%); MS (m/z): [M+H]$^+$=366]. The intermediate was converted into 5-(S)-aminomethyl-3-[4'-(tert-butoxycarbonyl)methylamino-3'-fluoro-phenyl]oxazolidine-2-one with triphenylphosphine (1.25 g, 4.8 mmol) as described above for the synthesis of 5-(S)-aminomethyl-3-[4'-(tert-butoxycarbonyl)methylamino-3'-fluorophenyl]oxazolidine-2-one. The resulted 5-(S)-aminomethyl-3-[4'-(tert-butyoxycarbonyl)methylamino-3'-fluoro-phenyl]oxazolidine-2-one was converted into 5-(S)-acetamidomethyl-3-[4'-methylamino-3'-fluorophenyl]oxazolidine-2-one via acetylation with acetic anhydride followed by TFA deprotection as described above for the synthesis of 5-(S)-acetamidomethyl-3-[4'-methylamino-3'-fluorophenyl]-oxazolidine-2-one. Yield 1.03 g (80%). R$_t$ 3.0 min. MS (m/z): [M+H]$^+$=282.

5-(S)-Thioacetamidomethyl-3-[4'-methylamino-3'-fluorophenyl]oxazolidine-2-one

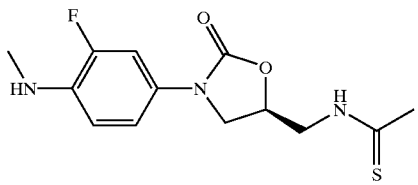

A mixture of 5-(S)-acetamidomethyl-3-[4'-methylamino-3'-fluorophenyl]oxazolidine-2-one (0.100 g, 0.356 mmol) and Lawesson reagent (0.144 g, 0.356 mmol) in dioxane (3 mL) was stirred at 65° C. for 2 h. Solvent was removed under vacuum and the residue purified by PTLC (10% methanol/dichloromethane) to give a product as foam. Yield 0.097 g (92%). MS (m/z): [M+H]$^+$=298.

Example 28

5-(S)-Thioacetamidomethyl-3-[4'-(N-methylformamido)-3'-fluorophenyl]oxa-zolidine-2-one

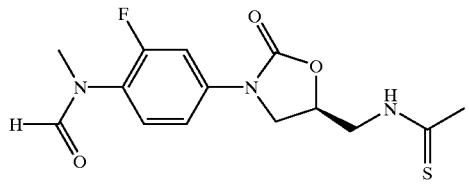

A mixture of 5-(S)-thioacetamidomethyl-3-[4'-methylamino-3'-fluorophenyl]-oxazolidine-2-one (0.100 g, 0.337 mmol) with p-nitrophenyl formate (0.084 g, 0.505 mmol), and (2,6-di-tert-butyl)pyridine (0.151 mL, 0.674 mmol) in THF (4 mL) was stirred at r.t. overnight. Solvent was removed under vacuum and the residue purified by PTLC (30% acetone in DCM) to give product as a white solid (0.089 g, 82%). M.p. 105–7° C. MS (m/z): [M+H]$^+$= 326.

5-(S)-Acetamidomethyl-3-[4'-(N-methylformamido)-3'-fluorophenyl]oxa-zolidine-2-one

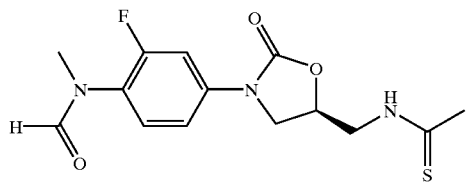

A solution of 5-(S)-acetamidomethyl-3-[4'-methylamino-3'-fluorophenyl]oxa-zolidine-2-one (0.200 g, 0.711 mmol), p-nitrophenyl formate (0.178 g, 1.07 mmol), and 2,6-di-tert-butylpyridine (0.319 mL, 1.42 mmol) in THF (4 mL) was stirred at r.t. overnight. Solvent was removed under vacuum and the residue purified by PTLC (30% acetone/dichloromethane) to give product as a white solid (0.188 g, 85%). M.p. 116–7° C.; MS (m/z): [M+H]$^+$=310.

Example 29

5-(S)-Thiocetamidomethyl-3-[4'-(N-methylthioformamido)-3'-fluorophenyl]-oxazolidine-2-one

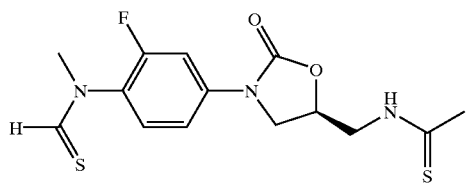

A mixture of 5-(S)-acetamidomethyl-3-[4'-(N-methylformamido)-3'-fluorophenyl]oxazolidine-2-one (0.100 g, 0.323 mmol) and Lawesson reagent (0.131 g, 0.323 mmol) in dioxane (3 mL) was stirred at 65° C. for 2 hours. Solvent was removed under vacuum and the residue purified by PTLC (10% MeOH in DCM) to give a white solid (0.101 g, 92%). M.p. 103–4° C. MS (m/z): [M+H]$^+$= 342.

Example 30

5-(S)-Acetamidomethyl-3-[4'-(5",6"-dihydro-1",4",2"-dioxazine-3"-yl)-3'-fluorophenyl]oxazolidine-2-one

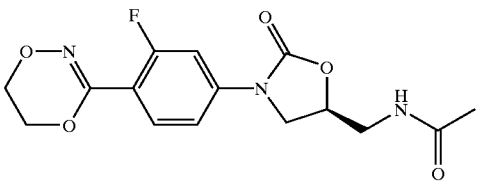

A solution of 5-(S)-acetamidomethyl-3-[4'-(N-hydroxyamino)carbonyl-3'-fluorophenyl]oxazolidine-2-one (0.100 g, 0.321 mmol; prepared as described in U.S. patent Ser. No. 09/235,771), cesium carbonate (0.209 g, 0.643 mmol), and 1,2-dibromoethane (0.0415 mL, 0.482 mmol) in 1-methyl-2-pyrrolidinone (4 mL) was heated at 100° C. overnight. The reaction mixture was diluted with ethyl acetate, washed with water, brine, dried (MgSO$_4$). Solvent was removed under vacuum, and the residue purified by PTLC (10% MeOH in DCM) to give product as a white solid (0.052 g, 48 %). M.p. 203–4° C. MS (m/z): [M+H]$^+$=338.

5-(S)-Thioacetamidomethyl-3-[4'-(5",6"-dihydro-1",4",2"-dioxazine-3"-yl)-3'-fluorophenyl]oxazolidine-2-one

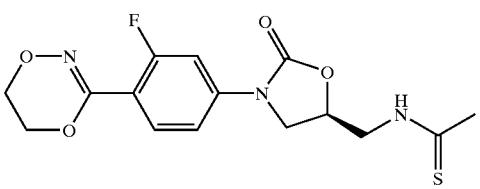

A mixture of 5-(S)-acetamidomethyl-3-[4'-(5",6"-dihydro-1",4",2"-dioxazine-3"-yl)-3'-fluorophenyl]oxazolidine-2-one (0.040 g, 0.119 mmol) and Lawesson's reagent (0.0481 g, 0.119 mmol) in dioxane (2 mL) was stirred at 65° C. for 2 hours. solvent was removed under vacuum and the residue purified by PTLC 10% MeOH in DCM) to give product as a white solid (0.034 g, 81%). M.p. 166–7° C.; MS (m/z): [M+H]$^+$=354.

Example 31

5-(S)-Thioacetamidomethyl-3-[4'-[N-methyl-(N-methylsulfonyl)amino]-3'-fluorophenyl]oxazolidine-2-one

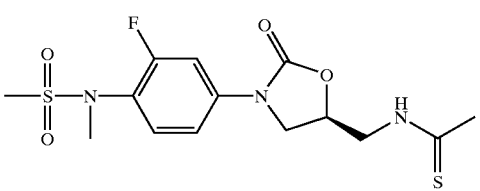

A mixture of 5-(S)-acetamidomethyl-3-[4'-[N-methyl-(N-methylsulfonyl)-amino]-3'-fluorophenyl]oxazolidine-2-one (0.100 g, 0.279 mmol; prepared analogously to U.S. patent Ser. No. 09/235,771) and Lawesson's reagent (0.113 g, 0.279 mmol) in dioxane (3 mL) was stirred and heated at 65° C. for 2 h. Solvent was removed under vacuum and the residue purified by PTLC (10% MeOH—DCM) to give a foam (0.090 g, 80%). MS (m/z): [M+H]⁺=376.

Example 32

Preparation and Use of Polymeric Thioacylating Agents

Polymeric Thioacylating Reagent: Merrifield Resin Dithioacetate.

Carbon disulfide (0.725 mL, 0.0121 mol) was added dropwise with stirring at r.t. to a solution of 3.0 M of methylmagnesium bromide in ether (3.09 mL, 9.27 mmol) in THF (15 mL), and the mixture stirred for 3 h under nitrogen atmosphere. Merrifield resin (0.74 mmol/g, 2.5 g, 1.85 mmol) was added in one portion, and the reaction agitated overnight. The resin was filtered, washed liberally with THF, MeOH, DCM, and dried under vacuum.

Thioamidation Using Merrifield Resin Dithioacetate.

Merrifield resin dithioacetate (0.458 g, 0.339 mmol) and 5-(S)-aminomethyl-3-(4'-morpholino-3'-fluorophenyl)oxazolidine-2-one (0.020 g, 0.0677 mmol) in DMF (2 ml) were agitated at 65° C. for 4 hours. Supernatant was filtered off and the solvent removed under vacuum to afford 5-(S)-thioamidomethyl-3-(4'-morpholino-3'-fluorophenyl)oxazolidine-2-one. MS (m/z): [M+H]⁺=354.

Example 33

Solid Phase Thioamide Synthesis.

A mixture of 5-(S)-aminomethyl-3-(4'-morpholino-3'-fluorophenyl)oxazolidine-2-one immobilized on BAL-linker functionalized Tentagel polymer (0.21 g, 0.06 mmol) and Lawesson reagent (0.088 g, 0.217 mmol) in dioxane (3 mL) was agitated at 60° C. for 3 h. The resin was filtered, washed liberally with DMF, DMSO, DCM, MeOH, and dried under vacuum. 40% TFA in DCM (2 mL) added, and the mixture agitated for 1 h at r.t. Supernatant was filtered off, and solvents removed under vacuum to afford 5-(S)-thioamidomethyl-3-(4'-morpholino-3'-fluorophenyl)oxazolidine-2-one. Rt 3.8 min. MS (m/z): [M+H]⁺=354.

Example 34

5-(S)-Azidomethyl-3-[4'-(5''-amino-1'',3'',4''-thiadiazole-2''-yl)-3'-fluoro-phenyl]oxazolidine-2-one

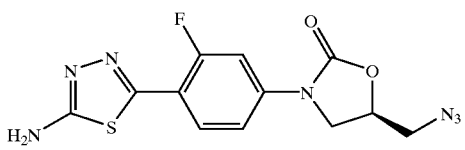

60% TFA in DCM (5 mL) was added to 5-(S)-azidomethyl-3-[4'-tert-butoxycarbonyl-3'-fluorophenyl]oxazolidine-2-one (0.336 g, 1 mmol), and the solution kept at r.t. for 1 h. Solvents were removed in vacuo to afford 5-(S)-azidomethyl-3-[4'-carboxy-3'-fluorophenyl]oxazolidine-2-one (0.280 g, 99%). A mixture of 5-(S)-azidomethyl-3-[4'-carboxy-3'-fluorophenyl]oxazolidine-2-one well stirred mixture of (0.080 g, 0.286 mmol) and thiosemicarbazide (0.0957 g, 0.286 mmol) in dioxane (2 mL) was heated until the mixture was homogeneous. Phosphorous oxychloride (0.027 ml, 0.29 mmol) was added, and the mixture heated at reflux for 1 h. The mixture was allowed to cool to r.t., and the white precipitate filtered, washed with dioxane, suspended in saturated aqueous sodium bicarbonate, and extracted with ethyl acetate. Combined oganic extracts were washed with brine, and dried (MgSO₄) Solvent was removed under vacuum, and the crude product purified by PTLC (10% MeOH in DCM) to give product as a white solid (0.038 g, 40%); MS (m/z): [M+H]⁺=336.

5-(S)-Aminomethyl-3-[4'-(5''-formamido-1'',3'',4''-thiadiazole-2''-yl)-3'-fluoro-phenyl]oxazolidine-2-one

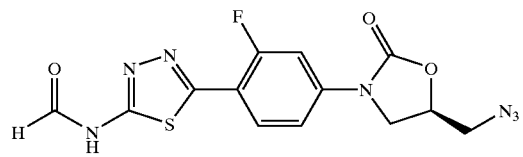

5-(S)-Azidomethyl-3-[4'-(5''-amino-1'',3'',4''-thiadiazole-2''-yl)aminocarbonyl-3'-fluorophenyl]oxazolidine-2-one (0.335 g, 1.0 mmol), p-nitrophenyl formate (0.188 g, 1.12 mmol), and 2,6-di-(tert-butyl)pyridine (0.336 mL, 1.50 mmol) in THF (4 mL) is stirred at 50–65° C. overnight. Solvent is removed under vacuum, and the resulted 5-(S)-azidomethyl-3-[4'-(5''-formamido-1'',3'',4''-thiadiazole-2''-yl)aminocarbonyl-3'-fluorophenyl]oxazolidine-2-one intermediate is purified by PTLC (MeOH—DCM). A mixture of 5-(S)-azidomethyl-3-[4'-(5''-formamido-1'',3'',4''-thiadiazole-2''-yl)aminocarbonyl-3'-fluorophenyl]oxazolidine-2-one (0.363 g, 1 mmol) and triphenylphosphine (0.262 g, 1.0 mmol) in THF (ca. 10 mL) is stirred at r.t. for 3–4 h and then at 40° C. for 2 h. Water (0.5 mL) is added, and the mixture stirred at 40° C. overnight. Solvents are removed in vacuo, and the crude product purified by PTLC (MeOH—DCM).

5-(S)-Acetamidomethyl-3-[4'-(5''-formamido-1'',3'',4''-thiadiazole-2''-yl)-3'-fluorophenyl]oxazolidine-2-one

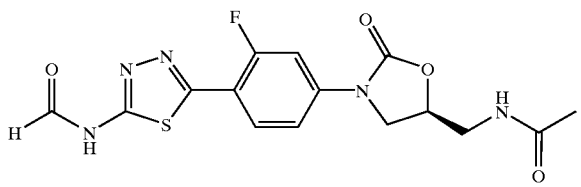

Acetic anhydride (0.14 mL, 1.5 mmol) is added to 5-(S)-aminomethyl-3-[4'-(5''-formamido-1'',3'',4''-thiadiazole-2''-yl)-3'-fluoro-phenyl]oxazolidine-2-one (0.34 g, 1 mmol) and polyvinylpyridine (0.50 g) in THF (7 mL), and the mixture is agitated at r.t. for 4 h. Supernatant is collected by filtration, and the resin washed with excess THF. Solvent is removed under vacuum to afford the product which can be further purified by PTLC (MeOH—DCM).

5-(S)-Thioacetamidomethyl-3-[4'-(5"-thioformamido-1",3",4"-thiadiazole-2"-yl)-3'-fluorophenyl]oxazolidine-2-one

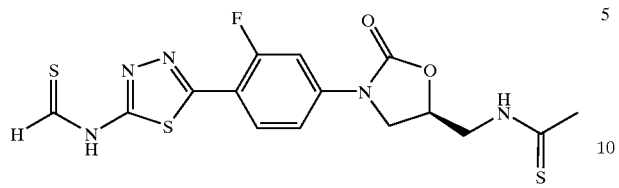

5-(S)-Acetamidomethyl-3-[4'-(5"-formamido-1",3",4"-thiadiazole-2"-yl)-3'-fluoro-phenyl]oxazolidine-2-one (0.38 g, 1.0 mmol) and Lawesson reagent (0.40 g, 1.0 mmol) in dioxane (10 mL) is stirred at 50–65° C. for 4–6 h. Solvent is removed under vacuum and the residue purified by PmC (MeOH—DCM).

Example 35

5-(S)-Azidomethyl-3-[4'-(5"-methylamino-1",3",4"-thiadiazole-2"-yl)-3'-fluoro-phenyl]oxazolidine-2-one

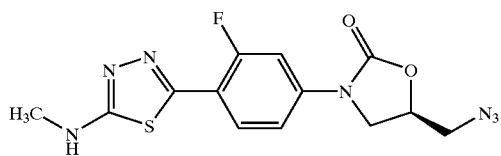

The compound is prepared analogously to described above synthesis of 5-(S)-azidomethyl-3-[4'-(5"-amino-1",3",4"-thiadiazole-2"-yl)-3'-fluorophenyl]oxazolidine-2-one from 5-(S)-azidomethyl-3-[4'-carboxy-3'-fluorophenyl]oxazolidine-2-one (0.10 g, 0.36 mmol), 4-methyl-3-thiosemicarbazide (0.038, 0.36 mmol), and phosphorus oxychloride ((0.033 mL, 0.36 mmol) in dioxane (2 mL). Crude product is purified by PTLC (MeOH—DCM).

5-(S)-Thioacetamidomethyl-3-[4'-(5"-(N-methyl)thioformamido-1",3",4"-thiadiazole-2"-yl)-3'-fluorophenyl]oxazolidine-2-one

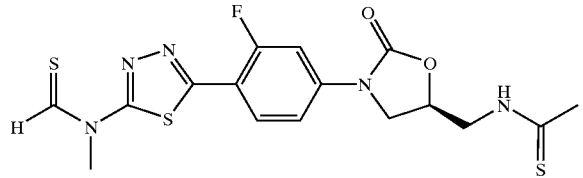

The compound is prepared from 5-(S)-azidomethyl-3-[4'-(5"-methylamino-1",3",4"-thiadiazole-2"-yl)-3'-fluorophenyl]oxazolidine-2-one analogously to described above synthesis of 5-(S)-thioacetamidomethyl-3-[4'-(5"-thioformamido-1",3",4"-thiadiazole-2"-yl)-3'-fluorophenyl]oxazolidine-2-one from 5-(S)-azidomethyl-3-[4'-(5"-amino-1",3",4"-thiadiazole-2"-yl)-3'-fluorophenyl]oxazolidine-2-one. Crude product is purified by PTLC (MeOH—DCM).

Example 36

5-(S)-Azidomethyl-3-[4'-(4"-methyl-5"-methylimino-4",5"-dihydro-1",3",4"-thiadiazole-2"-yl)-3'-fluorophenyl]oxazolidine-2-one

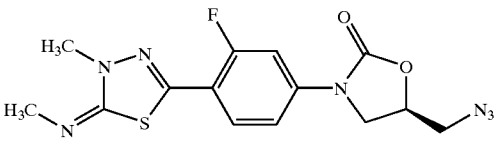

A mixture of 5-(S)-azidomethyl-3-[4'-(5"-methylamino-1",3",4"-thiadiazole-2"-yl)-3'-fluorophenyl]oxazolidine-2-one (0.10 g, 0.29 mmol) and methyl iodide (0.036 mL, 0.57 mmol) in dioxane (ca. 2 mL) is stirred under reflux overnight. Solvent is removed under vacuum, and the crude product is purified by PTLC (MeOH—DCM).

5-(S)-Aminomethyl-3-[4'-(4"-methyl-5"-methylimino-4",5"-dihydro-1",3",4"-thiadiazole-2"-yl)-3'-fluorophenyl]oxazolidine-2-one

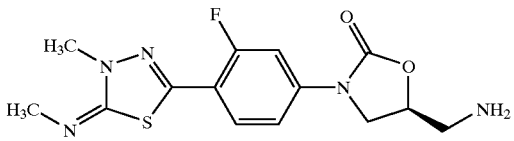

A mixture of 5-(S)-azidomethyl-3-[4'-(4"-methyl-5"-methylimino-4",5"-dihydro-1",3",4"-thiadiazole-2"-yl)-3'-fluorophenyl]oxazolidine-2-one (1.0 mmol) and triphenylphosphine (0.262 g, 1.0 mmol) in THF (ca. 10 mL) is stirred at r.t. for 3–4 h and then at 40° C. for 2 h. Water (0.5 mL) is added, and the mixture stirred at 40° C. overnight. Solvent is removed in vacuo, and the crude product purified by PTLC (MeOH—DCM).

5-(S)-Thioacetamidomethyl-3-[4'-(4"-methyl-5"-methylimino-4",5"-dihydro-1",3",4"-thiadiazole-2"-yl)-3'-fluorophenyl]oxazolidine-2-one

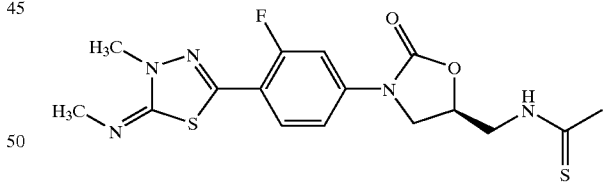

5-(S)-Aminomethyl-3-[4'-(4"-methyl-5"-methylimino-4",5"-dihydro-1",3",4"-thiadiazole-2"-yl)-3'-fluorophenyl]oxazolidine-2-one (1.0 mmol) and ethyl dithioacetate (0.130 ml, 1.13 mmol) with triethylamine (0.215 ml, 1.54 mmol) in DCM is stirred at r.t. overnight. The reaction mixture is concentrated under vacuum and the residue purified by PTLC (MeOH—DCM).

Example 37
Protocol for Assay of Antimicrobial Activity

Minimum inhibitor concentrations (MICs) were determined using the microdilution method according to National Committee for Clinical Laboratory Standards (NCCLS) procedures. Compounds were suspended in DMSO at 10 mg/ml and stored at −20° C. The range of concentrations tested was 64–0.06 μg/ml using two-fold dilutions.

To prepare the inoculum, bacterial cultures were grown overnight at 35° C. on agar plates and each organism was resuspended in 1 ml saline to obtain a 0.5 McFarlands density standard. This was subsequently diluted 1:200 into Mueller-Hinton Broth (MHB) or Haemophilus Test Medium (HTM; for Haemophilus) providing a final inoculum size of $5*10^5$ cfu/ml. After inoculation with the bacteria, assay plates were incubated at 35° C. for 18–24 h. The MIC was defined as the lowest concentration of compound that did not produce visible growth after incubation. Gram positive and gram negative strains used included *Staphylococcus aureus, Enterococcus faecium, Enterococcus faecalis, Streptococcus pneumoniae, Haemophilus influenzae, Pseudomonas aeruginosa, Escherichia coli,* and *E. coli* (acr)—an efflux pump mutant.

Example 38

5-(S)-Azidomethyl-3-[4'-aminocarbonyl-3'-fluorophenyl]oxazolidine-2-one

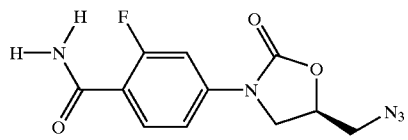

A solution of 5-(S)-azidomethyl-3-[4'-carboxy-3'-fluorophenyl-]oxazolidine-2-one (3.2 g, 11.4 mmol; prepared as described in Example 3), O-(7-azabenzotriazol-1-yl)-N,N,N',N',-tetramethyluronium hexafluorophosphate (6.5 g, 17.1 mmole) and N,N'-diisopropylethylamine (5.9 g, 7.9 ml, 45.6 mmoles) in DMF (12 ml) was stirred at room temperature for 20 min. Ammonium chloride (1.2 g, 22.8 mmol) was added, and the reaction mixture was stirred at r. t. overnight. Most of the solvent was removed under vacuum, and the residue taken up in ethyl acetate and washed twice with 3% aq. citric acid and brine. Organic layer was dried ($Na_2SO_4$) and concentrated under vacuum. Crude material was purified by silica gel chromatography eluting with 15% methanol in ethyl acetate to afford a white crystalline product (2.8 g, 91%). HPLC $R_t$=4.7, MS (m/z): $[M+H]^+$=280.

5-(S)-Aminomethyl-3-[4'-aminocarbonyl-3'-fluorophenyl]oxazolidine-2-one

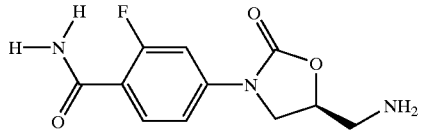

Triphenylphosphine (2.9 g, 11.0 mmol) was added portionwise to a solution of 5-(S)-azidomethyl-3-[4'-aminocarbonyl-3'-fluorophenyl]oxazolidine-2-one (2.8 g, 10.0 mmol) in THF (75 ml) under nitrogen atmosphere. The solution was stirred at 40° C. for 2 h, water (2.0 ml) added, and the reaction mixture was stirred at 40° C. overnight. Solvent was removed under vacuum, and the resulting solid was triturated with ether. Precipitated material was filtered, washed with ether and ethanol and dried under vacuum to afford the product as white crystals (1.7 g, 69%). HPLC $R_t$=5.0 min. MS (m/z): $[M+H]^+$=254.

5-(S)-Thioacetamidomethyl-3-[4'-aminocarbonyl-3'-fluorophenyl]oxazolidine-2-one

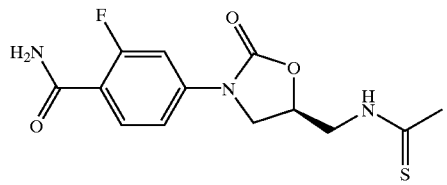

A solution of 5-(S)-aminomethyl-3-[4'-aminocarbonyl-3'-fluorophenyl]oxazolidine-2-one (1.75 g, 6.9 mmol), triethylamine (2.0 ml, 13.8 mmol) and ethyl dithioacetate (0.87 ml, 7.6 mmol) and DMF (5 ml) in acetonitrile (5 ml) was stirred at r.t. for 48 h. Solvent was removed under vacuum, and the crude material purified by silica gel chromatography (eluent: 10% methanol in ethyl acetate). White crystalline solid (1.3 g, 61%). HPLC $R_t$=4.5 min. MS (m/z): $[M+H]^+$=312.

Example 39

5-(S)-Azidomethyl-3-[4'-(pentafluorophenoxy)carbonyl-3'-fluorophenyl]-oxazolidine-2-one

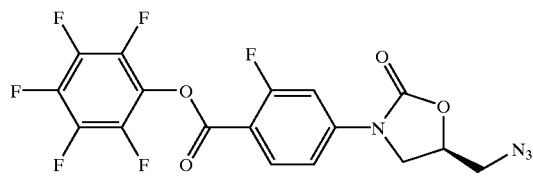

Pentafluorophenyl trifluoroacetate (2.2 ml, 12.9 mmol) was added dropwise with stirring to a solution of 5-(S)-azidomethyl-3-[4'-carboxy-3'-fluorophenyl]oxazolidine-2-one (3.0 g, 10.7 mmol; prepared as described in Example 3) and pyridine (3.5 ml, 42.8 mmol) in DMF (10 ml). The mixture was stirred at r.t. for 2.5 h, and ethyl acetate with 3% aq. citric acid added. Organic layer was washed twice with 3% citric acid, brine, and dried ($Na_2SO_4$). The crude material was washed with ether-hexanes to afford a white crystalline product (4.3 g, 90%). HPLC $R_t$=7.1. MS (m/z): $[M+H]^+$=447.

5-(S)-Azidomethyl-3-[4'-(N-methoxyamino)carbonyl-3'-fluorophenyl]-oxazolidine-2-one

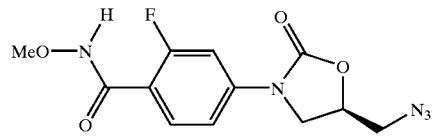

N-Methoxyamine hydrochloride (123 mg, 1.5 mmol) was added to a solution of 5-(S)-azidomethyl-3-[4'-(pentafluorophenoxy)carbonyl-3'-fluorophenyl]-oxazolidine-2-one (600 mg, 1.3 mmol) and diisopropylethylamine (0.26 ml, 1.5 mmol) in TBIF (8 ml), and the mixture stirred overnight at r.t. Solvent was removed under vacuum, and ethyl acetate with 3% aq. citric acid added. Organic layer was washed twice with 3% citric acid, brine, and dried ($Na_2SO_4$). Solvent was removed under vacuum, and the crude material crystallized from ethanol-ether to give a white crystalline product (335 mg, 83%). HPLC $R_t$=4.8. MS (m/z): $[M+H]^+$=310.

5-(S)-Aminomethyl-3-[4'-(N-methoxyamino)carbonyl-3'-fluorophenyl]-oxazolidine-2-one

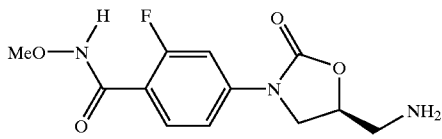

Triphenylphosphine (317 mg, 1.2 mmol) was added to a solution of 5-(S)-azidomethyl-3-[4'-(N-methoxyamino)carbonyl-3'-fluorophenyl]-oxazolidine-2-one. (0.335 g, 1.1 mmol) in THF (8 ml) under nitrogen atmosphere. The solution was stirred at 40° C. for 2 h, water (0.24 ml) was added, and the reaction mixture stirred at 40° C. overnight. Solvent was removed under vacuum, and the resulting solid was triturated with ether. Precipitated material was filtered, washed with ether and ethanol and dried under vacuum to afford the product as white crystals (120 mg, 42%). HPLC $R_t$=3.5 min. MS (m/z): [M+H]$^+$=284.

5-(S)-Thioacetamidomethyl-3-[4'-(N-hydroxyamino)carbonyl-3'-fluorophenyl]-oxazolidine-2-one

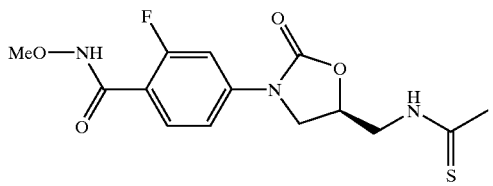

A solution of 5-(S)-aminomethyl-3-[4'-(N-methoxyamino)carbonyl-3'-fluorophenyl]-oxazolidine-2-one (0.053 ml, 0.47 mmol), triethylamine (0.12 ml, 0.84 mmol) and ethyl dithioacetate (0.87 ml, 7.6 mmol) in DMF (0.75 ml) was stirred at r.t. for 48 h. Solvent was removed under vacuum, and the crude material purified by silica gel PTLC (eluent: 5% MeOH in ethyl acetate). White crystalline solid (100 mg, 70%). HPLC $R_t$=4.6 min. MS (m/z): [M+H]$^+$=342.

Example 40

5-(S)-Acetamidomethyl-3-[4'-(N,N-dimethylamino)carbonyl-3'-fluorophenyl]-oxazolidine-2-one

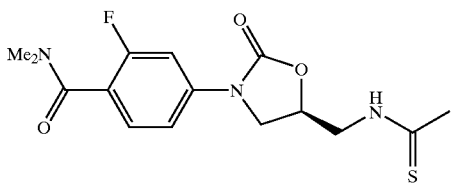

A mixture of 5-(S)-thioacetamidomethyl-3-(4'-carboxy-3'-fluorophenyl)oxazolidine-2-one (0.33 g, 1.06 mmol; prepared as described in Example 13), O-(7-azabenzotriazol-1-yl)-N,N,N',N',-tetramethyluronium hexafluorophosphate (0.428 g, 1.1 mmole) and N,N'-diisopropylethylamine (0.38 ml, 2.1 mmol) in DMF (1.5 ml) was stirred at r.t. for 20 min. Dimethylamine hydrochloride (96 mg, 1.2 mmole) was added, and the mixture stirred at r.t. overnight. Solvent was removed under vacuum, and the product purified by by silica gel PTLC (eluent: 10% MeOH in ethyl acetate). White crystals (117 mg, 33%). HPLC $R_t$=4.2. MS (m/z): [M+H]$^+$=340.

Example 41

5-(S)-Acetamidomethyl-3-[4'-(pentafluorophenoxy)carbonyl-3'-fluorophenyl]-oxazolidine-2-one

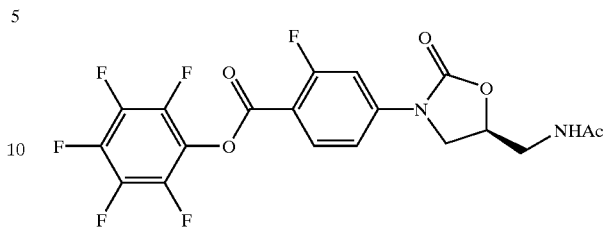

60% TFA in dichloroethane (10 ml) was added to 5-(S)-azidomethyl-3-[4'-tert-butoxycarbonyl-3'-fluorophenyl]oxazolidine-2-one (2.00 g, 5.95 mmol; prepared as described for Example 2) and the solution kept at r.t. for 1 h. Solvent was removed under vacuum to afford 5-(S)-azidomethyl-3-[4'-carboxy-3'-fluorophenyl]oxazolidine-2-one (1.65 g, 5.89 mmol, 99%). This intermediate was dissolved in DMF (15 ml), and pentafluorophenyl trifluoroacetate (1.21 ml, 7.06 mmol) and pyridine (1.91 ml, 23.6 mmol) were added with stirring. The mixture was stirred at r.t. for 3 h, most of the solvent removed under vacuum, and the residue triturated with water. The resulting precipitate was filtered, washed with water, ether, and dried under vacuum. White crystals. Yield g (2.53 g, 93%). MS (m/z): [M+H]$^+$=463.

5-(S)-Acetamidomethyl-3-[4'-(hydrazino)carbonyl-3'-fluorophenyl]oxazolidine-2-one

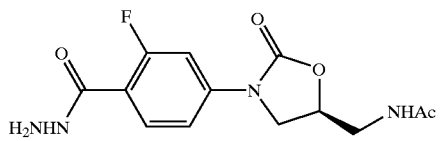

Hydrazine (0.041 ml, 1.30 mmol) was added dropwise with stirring to a solution of 5-(S)-acetamidomethyl-3-[4'-(pentafluorophenoxy)carbonyl-3'-fluorophenyl]oxazolidine-2-one (0.500 g, 1.08 mmol) in tetrahydrofuran (3 ml). The mixture was stirred at r.t. for 2 h, and the heavy white precipitate filtered, washed with ether, and dried under vacuum. Yield 0.295 g (88%). MS (m/z): [M+H]$^+$=311.

5-(S)-Thioacetamidomethyl-3-[4'-(hydrazino)carbonyl-3'-fluorophenyl]oxazolidine-2-one

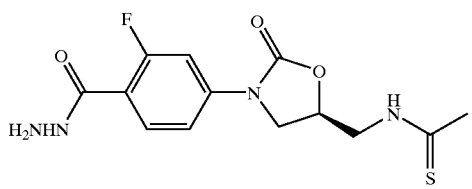

Tetrahydrofuran (5 ml) was added to a mixture of phosphorous pentasulfide (0.143 g, 0.322 mmol) and sodium carbonate (0.0341 g, 0.322 mmol) under a nitrogen atmosphere, and the mixture stirred vigorously at r.t. until a clear yellow solution was obtained. 5-(S)-Acetamidomethyl-3-[4'-(hydrazino)carbonyl-3'-fluorophenyl]oxazolidine-one (0.100 g, 0.322 mmol) was added in one portion, and the reaction stirred at r.t. overnight. Solvent was removed under vacuum, and the residue purified by PTLC (10% methanol in DCM) to give the pure product as a white solid (0.037 g, 35%). M.p. 177° C. MS (m/z): [M+H]⁺=327.

Example 42

5-(S)-Acetamidomethyl-3-[4'-(N-hydroxyamidino)-3'-fluorophenyl]oxazolidine-2-one

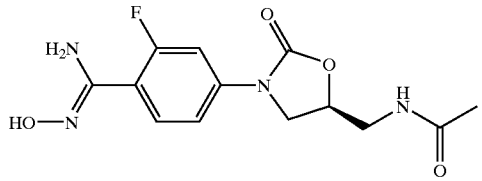

O-Trimethylsilylhydroxylamine (0.37 ml, 3.0 mmol) and 5-(S)-acetamidomethyl-3-[4'-cyano-3'-fluorophenyl] oxazolidine-2-one (0.277 g, 1.0 mmol) in ethanol (3.0 ml) were stirred at 80° C. in a sealed reaction vial for 2.5 h. The mixture was left at r.t. for 48 h, and the crystallized product filtered, rinsed with ethanol (ca. 0.75 ml), washed with ether, and dried under vacuum. Yellow crystals. Yield 0.260 g (84%). HPLC: $R_t$ 2.6 min. MS (m/z): [M+H]⁺=311.

5-(S)-Thioacetamidomethyl-3-[4'-(N-hydroxyamidino)-3'-fluorophenyl]oxazolidine-2-one

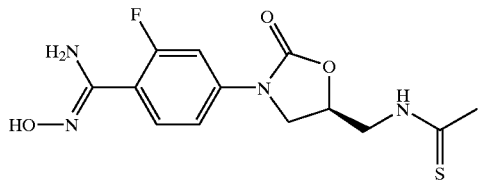

The compound is made analogously to that described above for Example 42 from 5-(S)-acetamidomethyl-3-[4'-(N-hydroxyamidino)-3'-fluorophenyl]oxazolidine-2-one (0.100 g, 0.32 mmol), phosphorous pentasulfide (0.143 g, 0.322 mmol) and sodium carbonate (0.0341 g, 0.322 mmol). The reaction is performed at r.t. overnight. Solvent is removed under vacuum, and the product isolated by preparative reverse phase HPLC.

Example 43

5-(S)-Acetamidomethyl-3-[4'-(N-methoxyamidino)-3'-fluorophenyl]oxazolidine-2-one

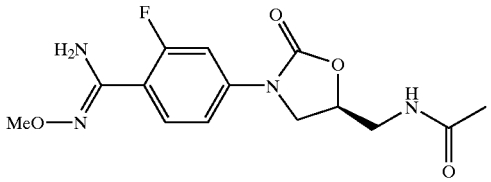

Iodomethane (0.02 ml, 0.39 mmol) was added to a solution of 5-(S)-acetamidomethyl-3-[4'-(N-hydroxyamidino)-3'-fluorophenyl]oxazolidine-2-one (0.080 g, 0.26 mmol) and tert-butyl-1,1,3,3-tetramethylguanidine (0.058 ml, 0.39 mmol) in DMF (1.0 ml), and the mixture was stirred at r.t. overnight. Solvent was removed under vacuum, and the crude product purified by silica gel PTLC (10% methanol in DCM). HPLC: $R_t$ 3.6 min. MS (m/z): [M+H]⁺=325.

5-(S)-Thioacetamidomethyl-3-[4'-(N-methoxyamidino)-3'-fluorophenyl]oxazolidine-2-one

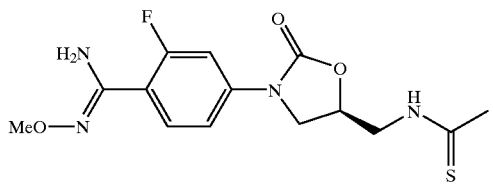

The compound is made analogously to that described above for Example 42 from 5-(S)-acetamidomethyl-3-[4'-(N-methoxyamidino)-3'-fluorophenyl]oxazolidine-2-one, phosphorous pentasulfide, and sodium carbonate in THF. The reaction is performed at r.t. overnight. Solvent is removed under vacuum, and the product isolated by preparative reverse phase HPLC.

Example 44

5-(S)-Acetamidomethyl-3-[4'-(N,N,N-trimethylaminimido)carbonyl-3'-fluorophenyl]-oxazolidine-2-one

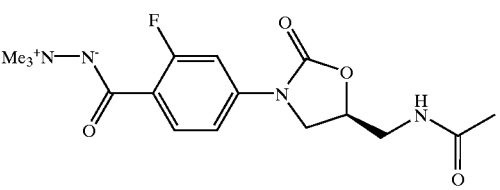

LiH (0.008 g, 1.1 mmol) was added to a solution of 5-(S)-acetamidomethyl-3-[4'-(hydrazino)carbonyl-3'-fluorophenyl]oxazolidine-2-one (0.018 g, 0.058 mmol) and methyl iodide (0.062 ml, 1.0 mmol) in dry DMSO (0.50 ml), and the mixture was stirred at r.t. overnight. The reaction was quenched with methanol (1.0 ml) and water (1.0 ml), and the product was purified by preparative reverse phase HPLC (gradient from 100% of 0.1% aq. TFA (solvent A) to 60% 0.1% TFA in acetonitrile—40% of solvent A over 40 min). White solid. Yield 0.005 g (25%). HPLC: $R_t$ 2.9 min. MS (m/z): [M+H]⁺=353.

5-(S)-Thioacetamidomethyl-3-[4'-(N,N,N-trimethylaminimido)carbonyl-3'-fluorophenyl]-oxazolidine-2-one

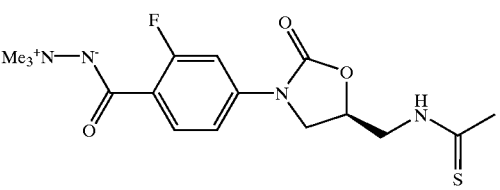

The compound is made analogously to that described above for Example 42 from 5-(S)-acetamidomethyl-3-[4'-(N,N,N-trimethylaminimido)carbonyl-3'-fluorophenyl]

oxazoli-dine-2-one, phosphorous pentasulfide and sodium carbonate in THF. The reaction is performed at r.t. overnight. Solvent is removed under vacuum, and the product isolated by preparative reverse phase HPLC.

Example 45

5-(S)-Thioacetamidomethyl-3-[4'-(6"-methylsulfinylpyridine-3"-yl)aminocarbonyl-3'-fluorophenyl]oxazolidine-2-one

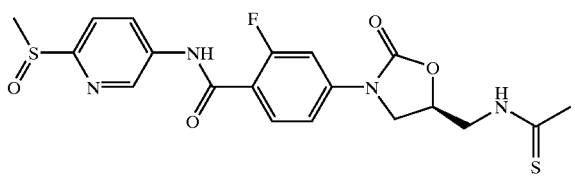

A solution of 5-(S)-thioacetamidomethyl-3-[4'-(pentafluorophenoxy)carbonyl-3'-fluorophenyl]oxazolidine-2-one (0.478 g, 1.0 mmol; prepared as described for Example 16), 3-amino-6-methylsulfinylpyridine (0.156 g, 1.0 mmol), triethylamine (0.202 g, 2.0 mmol) and 4-dimethylaminopyridine (0.012 g, 0.1 mmol) in dry acetonitrile is agitated at 50–60° C. overnight. Volatiles are removed under vacuum, and the crude product purified by PTLC (eluent: methanol-DCM).

Example 46

5-(S)-Thioacetamidomethyl-3-[4'-(5"-methylsulfinylthiazole-2"-yl)aminocarbonyl-3'-fluorophenyl]oxazolidine-2-one

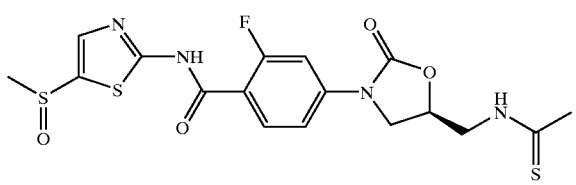

A solution of 5-(S)-thioacetamidomethyl-3-[4'-(pentafluorophenoxy)carbonyl-3'-fluorophenyl]oxazolidine-2-one (0.478 g, 1.0 mmol; prepared as described for Example 16), 2-amino-5-methylsulfinylthiazole (0.162 g, 1.0 mmol), triethylamine (0.202 g, 2.0 mmol) and 4-dimethylaminopyridine (0.012 g, 0.1 mmol) in dry acetonitrile is agitated at 50–60° C. overnight. Volatiles are removed under vacuum, and the product purified by PTLC (eluent: methanol-DCM).

Example 47

5-(S)-Thioacetamidomethyl-3-[4'-(5"-methylsulfinyl-1",3",4"-thiadiazole-2"-yl)aminocarbonyl-3'-fluorophenyl]oxazolidine-2-one

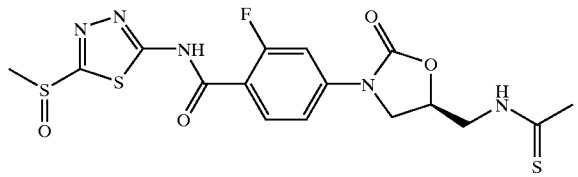

A solution of 5-(S)-thioacetamidomethyl-3-[4'-(pentafluorophenoxy)carbonyl-3'-fluorophenyl] oxazolidine-2-one (0.478 g, 1.0 mmol; prepared as described for Example 16), 2-amino-5-methylsulfinylthiazole (0.163 g, 1.0 mmol), triethylamine (0.202 g, 2.0 mmol) and 4-dimethylaminopyridine (0.012 g, 0.1 mmol) in dry acetonitrile is agitated at 50–60° C. overnight. Volatiles are removed under vacuum, and the product purified by PTLC (eluent: methanol-DCM).

Example 48

5-(S)-Acetamidomethyl-3-[4'-(3"-ethoxycarbonyl)thioureido-1"-yl)-3'-fluorophenyl]-oxazolidine-2-one

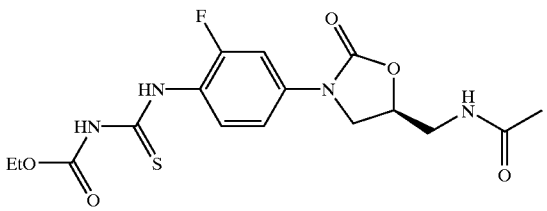

Ethoxycarbonyl isothiocyanate (0.50 ml, 4.1 mmol) was added to a solution of 5-(S)-acetamidomethyl-3-[4'-amino-3'-fluorophenyl]oxazolidine-2-one (0.50 g, 1.87 mmol; prepared as described for Example 21) in a mixture of NMP and DCM (1:1; 7 ml). Reaction was stirred at r.t. for 3 h, and the solvent was removed under vacuum. The residue was triturated with excess of hexanes and then ether. Resulted precipitate was filtered, washed with ether and dried under vaccum. Yield 0.73 g (98%). HPLC $R_t$ 4.2 min. MS (m/z) :[M+H]$^+$=399.

5-(S)-Thioacetamidomethyl-3-[4'-(3"-ethoxycarbonyl)thioureido-1"-yl)-3'-fluorophenyl]-oxazolidine-2-one

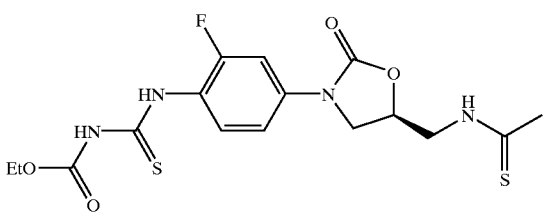

A mixture of 5-(S)-acetamidomethyl-3-[4'-(3"-ethoxycarbonyl)thioureido-1"-yl)-3'-fluorophenyl]-oxazolidine-2-one (0.200 g, 0.50 mmol) and the Lawesson's reagent (0.155 g, 0.38 mmol) in 1,4-dioxane (6 ml) was stirred at 65° C. overnight. Solvent was removed under vacuum, and the crude product purified by silica gel PTLC (eluent: 10% acetone in DCM). White solid. Yield 0.124 g (60%). HPLC $R_t$ 4.7 min. MS (m/z):[M+H]$^+$=415.

Example 49

5-(S)-Acetamidomethyl-3-[4'-(3"-ethoxycarbonyl) ureido-1"-yl)-3'-fluorophenyl]-oxazolidine-2-one

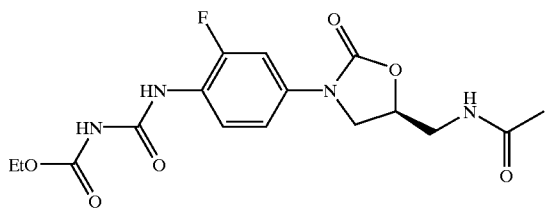

Ethoxycarbonyl isocyanate (0.29 ml, 2.8 mmol) was added to a solution of 5-(S)-acetamidomethyl-3-[4'-amino-3'-fluorophenyl]oxazolidine-2-one (0.50 g, 1.87 mmol; prepared as described for Example 21) in a mixture of NMP and DCM (1:1; 7 ml). Reaction was stirred at r.t. for 3 h, and the solvent was removed under vacuum. The residue was triturated with excess of hexanes and then ether. Resulted precipitate was filtered, washed with ether and dried under vaccum. Yield 0.65 g (91%). HPLC $R_t$ 4.0 min. MS (m/z):[M+H]$^+$=383.

5-(S)-Thioacetamidomethyl-3-[4'-(3"-ethoxycarbonyl)ureido-1"-yl)-3'-fluorophenyl]-oxazolidine-2-one

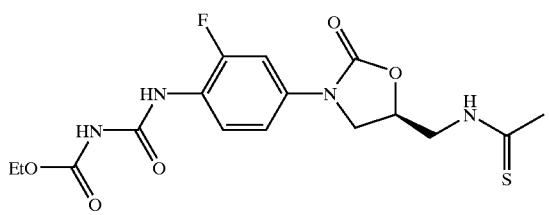

A mixture of 5-(S)-acetamidomethyl-3-[4'-(3"-ethoxycarbonyl)ureido-1"-yl)-3'-fluorophenyl]oxazolidine-2-one (0.300 g, 0.79 mmol) and the Lawesson's reagent (0.32, 0.79 mmol) in 1,4-dioxane (6 ml) was stirred at 65° C. overnight. Precipitated product was filtered, washed with 1,4-dioxane, ether, and dried under vacuum. White solid. Yield 0.299 g (95%). HPLC $R_t$ 4.5 min. MS (m/z):[M+H]$^+$=399.

Example 50

5-(S)-Acetamidomethyl-3-[4'-(3"-methoxycarbonyl) thioureido-1"-yl)-3'-fluorophenyl]-oxazolidine-2-one

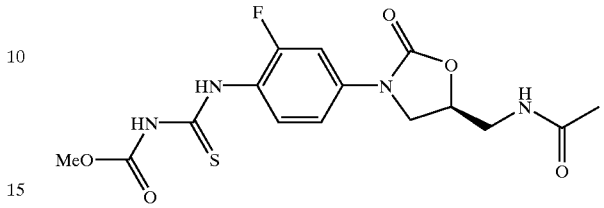

A solution of 5-(S)-acetamidomethyl-3-[4'-amino-3'-fluorophenyl]oxazolidine-2-one (0.50 g, 1.87 mmol; prepared as described for Example 21) in NMP (2 ml) was added dropwise with stirring to a solution of methoxycarbonyl isothiocyanate (generated in situ from methyl chloroformate (0.300 ml, 3.8 mmol) and Bu$_4$NCS (1.25 g, 4.16 mmol) in acetonitrile (8 ml), r.t., 6 h under nitrogen atmosphere), and the mixture was stirred at r.t. overnight. Solvents were removed under vacuum, the residue dissolved in a mixture of MeOH and DCM (1:1, 30 ml), and stirred with excess of the cation exchange resin IR 120 Plus overnight. Supernatant was filtered, solvents removed under vacuum, and the crude product purified by silica gel PTLC (eluent: 30% acetone in DCM). Yield 0.359 g (50%). HPLC $R_t$ 3.9 min. MS (m/z):[M+H]$^+$=385.

Example 51

5-(S)-Thioacetamidomethyl-3-[4'-(3"-methoxycarbonyl)thioureido-1"-yl)-3'-fluorophenyl]-oxazolidine-2-one

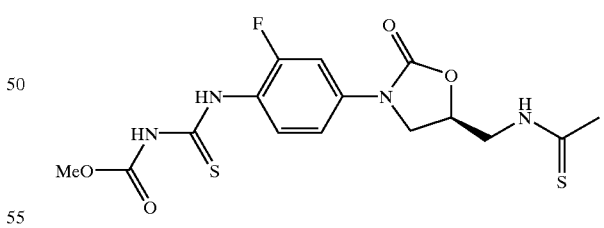

A mixture of 5-(S)-acetamidomethyl-3-[4'-(3"-methoxycarbonyl)thioureido-1"-yl)-3'-fluorophenyl] oxazolidine-2-one (0.24 g, 0.63 mmol) and the Lawesson's reagent (0.24, 0.60 mmol) in 1,4-dioxane (6 ml) was stirred at 70° C. overnight. Solvent was removed under vacuum, and the crude product purified by silica gel PTLC (eluent: hexanes-EtOAc 1:1). Yield 0.359 g (80%). HPLC $R_t$ 4.4 min. MS (m/z):[M+H]$^+$=401.

Example 52

5-(S)-Acetamidomethyl-3-[4'-(3"-methoxycarbonyl) ureido-1"-yl)-3'-fluorophenyl]-oxazolidine-2-one

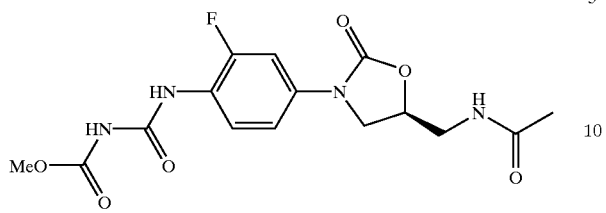

Methoxycarbonyl isocyanate (0.20 ml, 2.47 mmol) was added to a solution of 5-(S)-acetamidomethyl-3-[4'-amino-3'-fluorophenyl]oxazolidine-2-one (0.525 g, 1.96 mmol; prepared as described for Example 21) in a mixture of NMP and DCM (1:1; 10 ml). Reaction was stirred at r.t. for 4 h. The precipitated product was filtered, washed with excess of hexanes and ether, and dried under vacuum. White solid, yield 0.541 g (75%). HPLC $R_t$ 3.7 min. MS (m/z):[M+H]$^+$= 369.

5-(S)-Thioacetamidomethyl-3-[4'-(3"-methoxycarbonyl)ureido-1"-yl)-3'-fluorophenyl]-oxazolidine-2-one

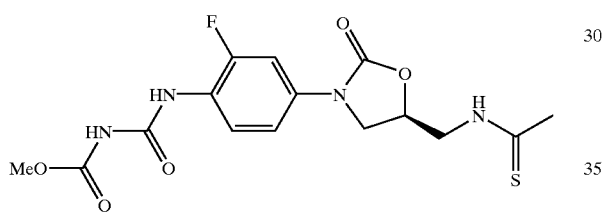

A mixture of 5-(S)-acetamidomethyl-3-[4'-(3"-methoxycarbonyl)ureido-1"-yl)-3'-fluorophenyl] oxazolidine-2-one (0.291 g, 0.79 mmol) and the Lawesson's reagent (0.32, 0.79 mmol) in 1,4-dioxane (6 ml) was stirred at 70° C. overnight. Precipitated product was filtered, washed with 1,4-dioxane, ether, and dried under vacuum. White solid. Yield 0.212 g (70%). HPLC $R_t$ 4.2 min. MS (m/z):[M+H]$^+$=385.

Example 53

5-(S)-Azidomethyl-3-[4'-methylthio-3'-fluorophenyl] oxazolidine-2-one

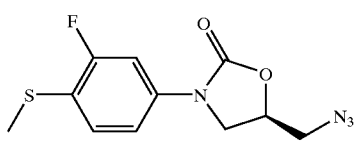

5% TFA and 2.5% triisopropylsilane in DCM (4 ml) was added to 5-(S)-azidomethyl-3-[4'-triphenylmethylthio-3'-fluorophenyl]oxazolidine-2-one (0.250 g, 0.490 mmol; prepared as described above for Example 6), and the mixture stirred for 1 h at r.t. Solvent was removed under vacuum and the residue dissolved in DMF (2 ml). Iodomethane (0.046 ml, 0.735 mmol) was added followed by dropwise addition of triethylamine (0.136 ml, 0.979 mmol). The mixture was stirred at r.t. for 2 h, evaporated, and the residue purified by PTLC (50% ethyl acetate in DCM) to give the product as a white solid (0.124 g, 90%). MS (m/z): [M+H]$^+$=283.

5-(S)-Azidomethyl-3-[4'-methylsulfinyl-3'-fluorophenyl]oxazolidine-2-one

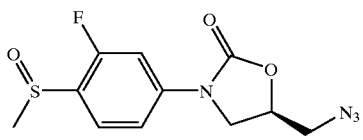

m-Chloroperoxybenzoic acid (77%, 0.079 g, 0.354 mmol) was added portionwise with stirring to a solution of 5-(S)-azidomethyl-3-[4'-methylthio-3'-fluorophenyl]oxazolidine-2-one (0.100 g, 0.354 mmol) in DCM (4 ml) at 0° C. The mixture was allowed to warm up to r.t. over 2 h. The mixture was washed with aq. saturated sodium bicarbonate, brine, dried (MgSO$_4$), and evaporated to give product as a white solid (0.100 g, 95%). MS (m/z): [M+H]$^+$=299.

5-(S)-Aminomethyl-3-[4'-methylsulfinyl-3'-fluorophenyl]oxazolidine-2-one

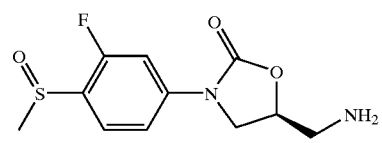

A mixture of triphenylphosphine (0.092 g, 0.352 mmol) and 5-(S)-azidomethyl-3-[4'-methylsulfinyl-3'-fluorophenyl]oxazolidine-2-one (0.100 g, 0.335 mmol) in tetrahydrofuran (2 ml) was stirred at r.t. for 4 h. Water (0.1 ml, 5.36 mmol) was added, and the mixture heated at 40° C. overnight. Solvent was evaporated under vacuum and the residue purified by PTLC (10% methanol in DCM) to give product as a white solid (0.082 g, 86%). MS (m/z): [M+H]$^+$= 273.

5-(S)-Thioacetamidomethyl-3-[4'-methylsulfinyl-3'-fluorophenyl]oxazolidine-2-one

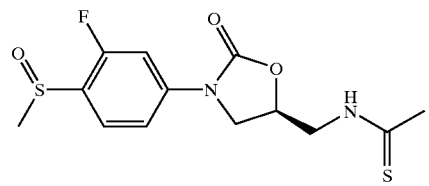

Prepared analogously to the Method A of General Methods of Preparation of 5-(S)-Thioamidomethyloxazolidinones (Example 1) from 5-(S)-aminomethyl-3-[4'-methylsulfinyl-3'-fluorophenyl] oxazolidine-2-one (0.050 g, 0.184 mmol) and ethyl dithioacetate. Reaction was performed in DMF overnight. Yield 0.058 g (96%). M.p 158–60° C. MS (m/z): [M+H]$^+$= 331.

Example 54

5-(S)-Azidomethyl-3-[4'-ethylthio-3'-fluorophenyl]oxazolidine-2-one

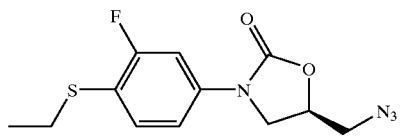

This compound was prepared analogously to the synthesis of 5-(S)-azidomethyl-3-[4'-methylthio-3'-fluorophenyl]oxazolidine-2-one from iodoethane (0.117 ml, 1.47 mmol) and 5-(S)-azidomethyl-3-[4'-triphenylmethylthio-3'-fluorophenyl]oxazolidine-2-one (0.500 g, 0.979 mmol). Yield 0.267 g (92%). MS (m/z): [M+H]$^+$=297.

5-(S)-Azidomethyl-3-[4'-ethylsulfinyl-3'-fluorophenyl]oxazolidine-2-one

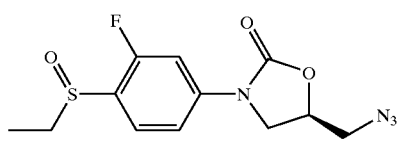

This compound was prepared analogously to the synthesis of 5-(S)-azidomethyl-3-[4'-methylsulfinyl-3'-fluorophenyl]oxazolidine-2-one from 5-(S)-azidomethyl-3-[4'-ethylthio-3'-fluorophenyl]oxazolidine-2-one (0.250 g, 0.844 mmol) and m-chloroperoxybenzoic acid (77%, 0.189 g, 0.844 mmol). Yield 0.235 g (89%). MS (m/z): [M+H]$^+$=313.

5-(S)-Aminomethyl-3-[4'-ethylsulfinyl-3'-fluorophenyl]oxazolidine-2-one

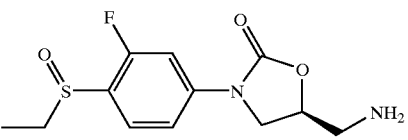

This compound was prepared analogously to the synthesis of 5-(S)-aminomethyl-3-[4'-methylsulfinyl-3'-fluorophenyl]oxazolidine-2-one from 5-(S)-azidomethyl-3-[4'-ethylsulfinyl-3'-fluorophenyl]oxazolidine-2-one (0.235 g, 0.752 mmol) and triphenylphosphine (0.207 g, 0.790 mmol). Yield 0.177 g (82%). MS (m/z): [M+H]$^+$=287.

5-(S)-Thioacetamidomethyl-3-[4'-ethylsulfinyl-3'-fluorophenyl]oxazolidine-2-one

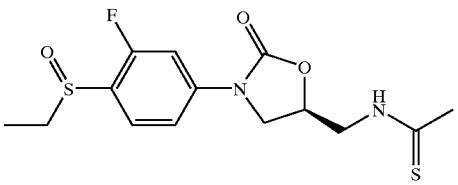

Prepared analogously to the Method A of General Methods of Preparation of 5-(S)-Thioamidomethyloxazolidinones (Example 1) from 5-(S)-aminomethyl-3-[4'-ethylsulfinyl-3'-fluorophenyl]oxazolidine-2-one (0.0885 g, 0.309 mmol) and ethyl dithioacetate. Reaction was performed in DMF overnight. Yield 0.104 g (98%). M.p. 138–9° C. MS (m/z): [M+H]$^+$=345.

Example 55

5-(S)-Azidomethyl-3-[4'-(2''-fluoroethyl)thio-3'-fluorophenyl]oxazolidine-2-one

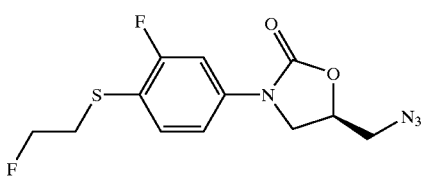

This compound was prepared analogously to the synthesis of 5-(S)-azidomethyl-3-[4'-methylthio-3'-fluorophenyl]oxazolidine-2-one from 1-bromo-2-fluoroethane (0.109 ml, 1.47 mmol) and 5-(S)-azidomethyl-3-[4'-triphenylmethylthio-3'-fluorophenyl]-oxazolidine-2-one (0.500 g, 0.979 mmol). Yield 0.280 g (91%). MS (m/z): [M+H]$^+$=315.

5-(S)-Azidomethyl-3-[4'-(2''-fluoroethyl)sulfinyl-3'-fluorophenyl]oxazolidine-2-one

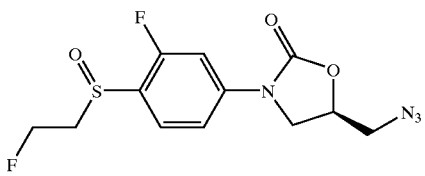

This compound was prepared analogously to the synthesis of 5-(S)-azidomethyl-3-[4'-methylsulfinyl-3'-fluorophenyl]oxazolidine-2-one from 5-(S)-azidomethyl-3-[4'-(2''-fluoroethyl)thio-3'-fluorophenyl]oxazolidine-2-one (0.280 g, 0.891 mmol) and m-chloroperoxybenzoic acid (77%, 0.200 g, 0.891 mmol). Yield 0.280 g (95%). MS (m/z): [M+H]$^+$=331.

5-(S)-Aminomethyl-3-[4'-(2''-fluoroethyl)sulfinyl-3'-fluorophenyl]oxazolidine-2-one

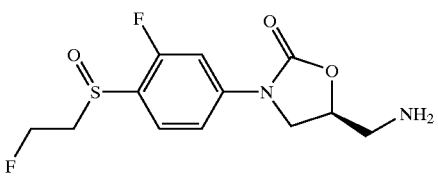

This compound was prepared analogously to the synthesis of 5-(S)-aminomethyl-3-[4'-methylsulfinyl-3'-fluorophenyl]oxazolidine-2-one from 5-(S)-azidomethyl-3-[4'-(2''-fluoroethyl)sulfinyl-3'-fluorophenyl]oxazolidine-2-one (0.275 g, 0.833 mmol) and triphenylphosphine (0.229 g, 0.874 mmol). Yield 0.253 g (80%). MS (m/z): [M+H]$^+$=305.

5-(S)-Thioacetamidomethyl-3-[4'-(2"-fluoroethyl) sulfinyl-3'-fluorophenyl]-oxazolidine-2-one

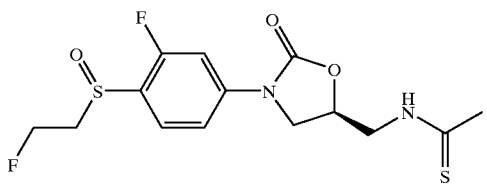

Prepared analogously to the Method A of General Methods of Preparation of 5-(S)-Thioamidomethyloxazolidinones (Example 1) from 5-(S)-aminomethyl-3-[4'-(2"-fluoroethyl)sulfinyl-3'-fluorophenyl]oxazolidine-2-one (0.100 g, 0.329 mmol) and ethyl dithioacetate. Reaction was performed in DMF overnight. Yield 0.114 g (96%). M.p. 161° C. MS (m/z): [M+H]$^+$=363.

Example 56

5-(S)-Acetamidomethyl-3-[4'-methylsulfinyl-3'-fluorophenyl]oxazolidine-2-one

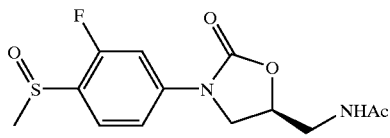

Acetic anhydride (0.173 ml, 1.83 mmol) and pyridine (0.296 ml, 3.67 mmol) were added to a solution of 5-(S)-aminomethyl-3-[4'-methylsulfinyl-3'-fluorophenyl] oxazolidine-2-one (0.100 g, 0.367 mmol) in DCM (3 ml). The reaction mixture was stirred for 4 h at r.t. and then evaporated to dryness under vacuum. The residue was purified by PTLC (10% methanol in DCM) to give product as a white solid (0.115 g, 99%). M.p. 143–5° C. MS (m/z): [M+H]$^+$=315.

5-(S)-Acetamidomethyl-3-[4'-methylsulfonyl-3'-fluorophenyl]oxazolidine-2-one

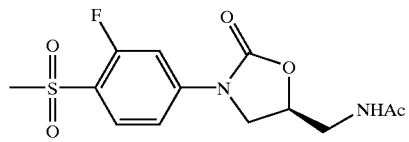

m-Chloroperoxybenzoic acid (77%, 0.0784 g, 0.350 mmol) was added portionwise to a solution of 5-(S)-Acetamidomethyl-3-[4'-methylsulfinyl-3'-fluorophenyl] oxazolidine-2-one (0.110 g, 0.350 mmol) in DCM (20 ml) at r.t. The mixture was stirred for 2 h, then washed with aq. saturated sodium bicarbonate, brine, dried (MgSO$_4$), and evaporated to give product as a white solid (0.106 g, 92%). MS (m/z): [M+H]$^+$=331.

5-(S)-Thioamidomethyl-3-[4'-methylsulfonyl-3'-fluorophenyl]oxazolidine-2-one

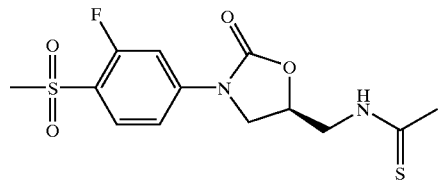

Prepared analogously to the Method B (Example 1) of General Methods for Preparation of 5-(S)-Thioamidomethyloxazolidinones from 5-(S)-acetamidomethyl-3[4'-methylsulfonyl-3'-fluorophenyl] oxazolidinone (0.100 g, 0.303 mmol) and Lawesson's reagent. Yield 0.078 g (75%). M.p. 177° C. MS (m/z): [M+H]$^+$=347.

Example 57

5-(S)-Aminomethyl-3-[4'-(5"-amino-1",3",4"-thiadiazole-2"-yl)-3'-fluorophenyl]-oxazolidine-2-one

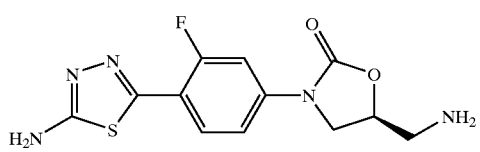

Triphenylphosphine (0.376 g, 1.4 mmol) was added to a mixture of 5-(S)-azidomethyl-3-[4'-(5"-amino-1",3",4"-thiadiazole-2"-yl)-3'-fluorophenyl]oxazolidine-2-one (0.402 g, 1.3 mmol; prepared as described for Example 34) in DMF (7 ml) under nitrogen atmosphere. The solution was stirred at 40° C. for 6 h, then water (0.7 ml) was added, and the reaction mixture stirred at 55° C. overnight. Most of solvent was removed under vacuum, and the resulting solid was triturated with ether. Precipitated material was filtered, washed with MeOH, excess of ether, and dried under vacuum to afford the product as a white solid (0.320 g, 80%). MS (m/z): [M+H]$^+$=310.

5-(S)-Thioacetamidomethyl-3-[4'-(5"-amino-1",3", 4"-thiadiazole-2"-yl)fluorophenyl]-oxazolidine-2-one

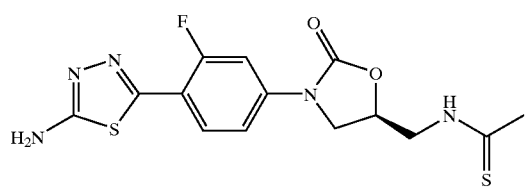

A solution of 5-(S)-aminomethyl-3-[4'-(5"-amino-1",3", 4"-thiadiazole-2"-yl)-3'-fluorophenyl]oxazolidine-2-one (0.155 g, 0.5 mmol) and ehyl dithioacetate (0.093 ml, 0.67 mmol) with triethylamine (0.080 ml, 0.67 mmol) in DMF (2 ml) was stirred at r.t. overnight. Most of the solvent was removed under vacuum, residue washed with ether, and the crude product purified by silica gel PTLC (eluent: 10% MeOH in DCM). White crystals, yield 0.92 g (50%). HPLC R$_t$=3.8 min. MS (m/z): [M+H]$^+$=368.

Example 58

5-(S)-Azidomethyl-3-[4'-(thiosemicarbazide-1"-yl)carbonyl-3'-fluorophenyl]-oxazolidine-2-one

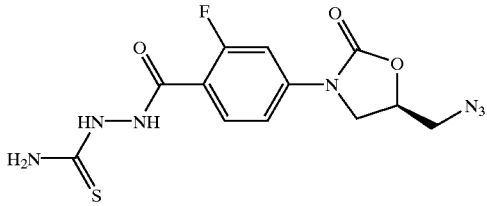

A solution of 5-(S)-azidomethyl-3-[4'-carboxy-3'-fluorophenyl]oxazolidine-2-one (1.0 g, 3.6 mmol; prepared as described in Example 3), O-(7-azabenzotriazol-1-yl)-N,N,N',N',-tetramethyluronium hexafluorophosphate (1.5 g, 3.9 mmol) and N,N'-diisopropylethylamine (1.9 ml, 10.8 mmol) in DMF (4 ml) was stirred at r.t. for 20 minutes. Thiosemicarbazide (0.351 g, 3.9 mmol) was added, and the reaction mixture was stirred at r.t. overnight. Most of the solvent was removed under vacuum, and the crude material purified by silica gel chromatography eluting with 20% hexanes in ethyl acetate to afford the white crystalline product (0.460 g, 36%). HPLC $R_t$=3.4. MS (m/z): [M+H]$^+$=354.

5-(S)-Aminomethyl-3-[4'-(thiosemicarbazide-1"-yl)carbonyl-3'-fluorophenyl]-oxazolidine-2-one

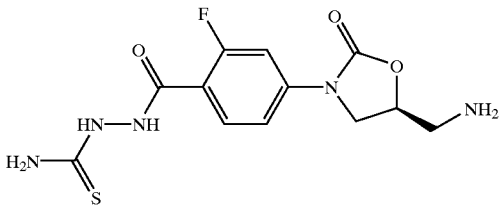

Triphenylphosphine (0.376 g, 1.4 mmol) was added to a solution of 5-(S)-azidomethyl-3-[4'-(thiosemicarbazide-1-yl)carbonyl-3'-fluorophenyl]-oxazolidine-2-one (0.46 g, 1.3 mmol) in THF (15 ml) under nitrogen atmosphere. The solution was stirred at 40° C. for 3 h, water (1.5 ml) was added, and the reaction mixture stirred at 40° C. overnight. Solvent was removed under vacuum, and the resulting solid was triturated with ether. Precipitated material was filtered, washed with ether and ethanol and dried under vacuum to afford the product as white crystals (0.370 g, 87%). HPLC $R_t$=3.2 min. MS (m/z): [M+H]$^+$=328.

5-(S)-(tert-Butoxycarbonyl)aminomethyl-3-[4'-(thiosemicarbazide-1"-yl)carbonyl-3'-fluorophenyl]-oxazolidine-2-one

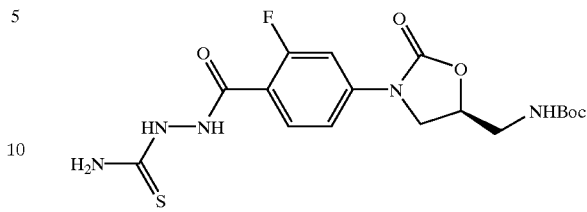

di-tert-Butyl dicarbonate (0.288 g, 1.3 mmol) was added with stirring at 5° C. to the mixture of 5-(S)-aminomethyl-3-[4'-(thiosemicarbazide-1-yl)carbonyl-3'-fluorophenyl]-oxazolidine-2-one (0.370 g, 1.1 mmol) and triethylamine (0.31 ml, 2.2 mmol) in THF (30 ml) with DMF (5 ml). The mixture was stirred overnight at r.t., and solvent was removed under vacuum. The residue was partitioned between EtOAc and water, and resulted emulsion filtered through Celite. Organic layer was separated and dried (Na$_2$SO$_4$). Evaporation of solvent afforded a white crystalline product (0.480 g, quant.). HPLC $R_t$=4.3 min. MS (m/z): [M+H]$^+$=428.

5-(S)-(tert-Butoxycarbonyl)aminomethyl-3-[4'-(5"-amino-1",3",4"-oxadiazole-2"-yl)-3'-fluorophenyl]-oxazolidine-2-one

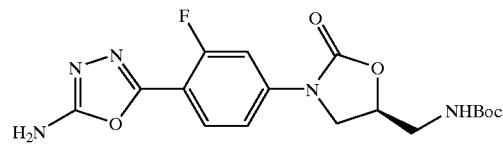

A mixture of 5-(S)-(tert-butoxycarbonyl)aminomethyl-3-[4'-(thiosemicarbazide-1"-yl)carbonyl-3'-fluorophenyl]-oxazolidine-2-one (0.425 g, 1.0 mmol) and red mercury (II) oxide (0.432 g, 2.0 mmol) in DMF (3 ml) was stirred at 60° C. for 2 h. Solvent was removed under vacuum, and the crude material purified by silica gel chromatography (eluent: EtOAc) to afford a white crystalline product (0.160 g, 41%). HPLC $R_t$+4.5 min. MS (m/z): [M+H]$^+$=394.

5-(S)-Thioacetamidomethyl-3-[4'-(5"-amino-1",3",4"-oxadiazole-2"-yl)-3'-fluorophenyl]-oxazolidine-2-one

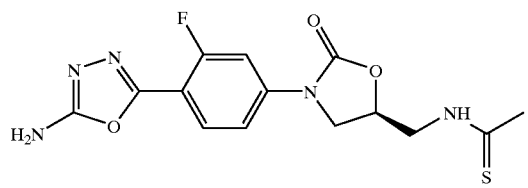

A solution of 5-(S)-(tert-butoxycarbonyl)aminomethyl-3-[4'-(5"-amino-1",3",4"-oxadiazole-2"-yl)fluorophenyl]-oxazolidine-2-one. (0.160 g, 0.41 mmol) in 40% trifluoroacetic acid in DCM (8 ml) was stirred at r.t. for 1.5 h. Volatiles were removed under vacuum at r.t., and the gummy residue redissolved in MeOH and evaporated to afford the intermediate 5-(S)-aminomethyl-3-[4'-(5"-amino-1",3",4"-oxadiazole-2"-yl)fluorophenyl]-oxazolidine-2-one trifluoroacetate as a white crystalline solid (HPLC $R_t$=3.1 min. MS (m/z): [M+H]$^+$=294). A solution of above intermediate and ehyl dithioacetate (0.093 ml, 0.67 mmol) with triethylamine (0.080 ml, 0.67 mmol) in DMF (2 ml) was stirred at r.t. for 3 h. Solvent was removed under vacuum, and the product was purified by silica gel column chromatography (eluted with a mixture of 1% AcOH and 15% MeOH in DCM). White crystals (0.051 g, 36%). HPLC $R_t$=4.0 min. MS (m/z): [M+H]$^+$=352.

Although the foregoing invention has been described in some detail by way of illustration and example for purposes of clarity and understanding, it will be apparent to those skilled in the art that certain changes and modifications may be practical. Therefore, the description and examples should not be construed as limiting the scope of the invention.

What is claimed is:

1. A compound of formula 1:

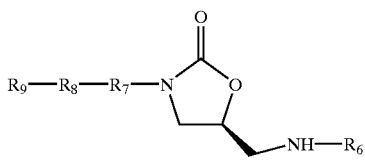

wherein:

$R_6$ is thioacyl, aminothiocarbonyl, alkoxythiocarbonyl, alkylthio(carbonyl), or alkylthio(thiocarbonyl);

$R_7$ is aryl or monocyclic heteroaryl;

$R_8$ is $C_4$–$C_7$ alkyl, $C_2$–$C_7$ alkynyl, O, OC(=O), OC(=O)NR, NRC(=O)O, C(=S)NR, NRC(=S), C(=S), C(=S)O, OC(=S), OC(=S)NR, NRC(=S)O, NRCONR', NRC(=S)NR', or (CH$_2$)$_n$O, wherein n=2–6, and wherein R and R' are independently H, alkyl, heteroalkyl, aryl or heteroaryl; and $R_9$ is hydrogen, OH, OR", SR", NR"R'", alkyl, aryl, heteroalkyl, or heteroaryl, and wherein R" and R'" are independently H, alkyl, heteroalkyl, aryl or heteroaryl, with the proviso that when $R_7$ is aryl, $R_6$ is different from alkylthio(carbonyl).

2. The compound of claim 1 wherein:

$R_8$ is OC(=O), OC(=O)NR, C(=S)NR, NRC(=S), OC(=S)NR, NRC(=S)O, or NRC(=S)NR', wherein R and R' are independently H, alkyl, heteroalkyl, aryl or heteroaryl; and $R_9$ is hydrogen, OR", SR", NR"R'", alkyl, aryl, or heteroaryl, wherein each R" and R'" are independently H, alkyl, aryl or heteroaryl.

3. The compound of claim 1 wherein $R_6$ is a thioacyl group.

4. A compound of claim 3 wherein the thioacyl group is selected from the group consisting of C(=S)CH$_3$, C(=S)CH$_2$CH$_3$, C(=S)H, and C(=S) cyclopropyl.

5. A compound of formula 3:

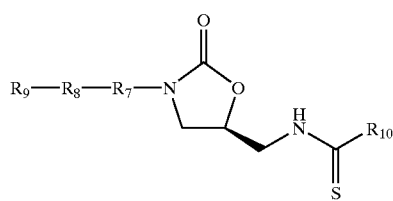

wherein:

$R_7$ is aryl or monocyclic heteroaryl;

$R_8$ is $C_1$–$C_7$ alkyl, $C_2$–$C_7$ alkenyl, $C_2$–$C_7$ allynyl, NR, O, S, C(=O)NR, NRC(=O), C(=O), C(=O)O, OC(=O), OC(=O)NR, NRC(=O)O, C(=S)NR, NRC(=S), C(=S), C(=S)O, OC(=S), OC(=S)NR, NRC(=S)O, S(=O), SO$_2$, SO$_2$NR, NRSO$_2$, NRCONR', NRC(=S)NR', or (CH$_2$)$_n$O, wherein n=2–6, and wherein each R and R' are independently H, alkyl, heteroalkyl, aryl or heteroaryl;

$R_9$ is hydrogen, OH, OR", SR", NR"R'", alkyl, aryl, heteroalkyl, or heteroaryl, and wherein each R" and R'" are independently H, alkyl, heteroalkyl, aryl or heteroaryl; and $R_{10}$ (is heteroalkyl, aryl, heteroaryl, or $C_{1-4}$ alkyl substituted with one or more NO$_2$.

6. The compound of claim 5, wherein:

$R_8$ is NR, S, C(=O)NR, NRC(=O), C(=O)O, OC(=O), OC(=O)NR, C(=S)NR, NRC(=S), OC(=S)NR, NRC(=S)O, or NRC(=S)NR', wherein R and R' are independently H, alkyl, heteroalkyl, aryl or heteroaryl; and $R_9$ is hydrogen, OR", SR", NR"R'", alkyl, aryl, or heteroaryl, wherein R' and R'" are independently H, alkyl, aryl or heteroaryl.

7. A compound of formula 6:

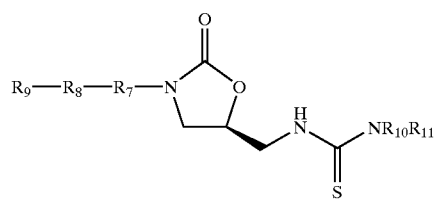

wherein:

$R_7$ is aryl or monocyclic heteroaryl;

$R_8$ is $C_1$–$C_7$ alkyl, $C_2$–$C_7$ alkenyl, $C_2$–$C_7$ alkynyl, NR, O, S, C(=O)NR, NRC(=O), C(=O), C(=O)O, OC(=O), OC(=O)NR, NRC(=O)O, C(=S)NR, NRC(=S), C(=S), C(=S)O, OC(=S), OC(=S)NR, NRC(=S)O, S(=O), SO$_2$, SO$_2$NR, NRSO$_2$, NRCONR', NRC(=S)NR', or (CH$_2$)$_n$O, wherein n=2–6, and wherein R and R' are independently H, alkyl, heteroalkyl, aryl or heteroaryl;

$R_9$ is hydrogen, OH, OR", SR", NR"R'", alkyl, aryl, heteroalkyl, or heteroaryl, and wherein R" and R'" are independently H, allyl, heteroalkyl, aryl or heteroaryl;

$R_{10}$ and $R_{11}$ are independently aryl or heteroaryl.

8. The compound of claim 7, wherein:

$R_8$ is NR, S, C(=O)NR, NRC(=O), C(=O)O, OC(=O), OC(=O)NR, C(=S)NR, NRC(=S),

OC(=S)NR, NRC(=S)O, or NRC(=S)NR', wherein R and R' are independently H, alkyl, heteroalkyl, aryl or heteroaryl; and $R_9$ is hydrogen, OR", SR", NR"R''', alkyl, aryl, or heteroaryl, wherein R" and R''' are independently H, alkyl, aryl or heteroaryl.

9. A compound of formula 7:

$$R_9-R_8-R_7-N\underset{S}{\overset{O}{\bigcirc}}\overset{H}{\underset{}{N}}OR_{10}$$ (7)

wherein.

$R_7$ is aryl or monocyclic heteroaryl;

$R_8$ is $C_2$–$C_7$ alkyl, $C_2$–$C_7$ alkenyl, $C_2$–$C_7$ alkynyl, NR, O, S, C(=O)NR, NRC(=O), C(=O), C(=O)O, OC(=O), OC(=O)NR, NRC(=O)O, C(=S)NR, NRC(=S), C(=S), C(=S)O, OC(=S), OC(=S)NR, NRC(=S)O, S(=O), SO$_2$, SO$_2$NR, NRSO$_2$, NRCONR', NRC(=S)NR', or (CH$_2$)$_n$O, wherein n=2–6, and wherein R and R' are independently H, alkyl, heteroalkyl, aryl or heteroaryl;

$R_9$ is hydrogen, OH, OR", SR", NR"R''', alkyl, aryl, heteroalkyl, or heteroaryl, and wherein R" and R''' are independently H, alkyl, heteroalkyl, aryl or heteroaryl; and $R_{10}$ is heteroalkyl, aryl or heteroaryl.

10. The compound of claim 9, wherein:

$R_8$ is NR, S, C(=O)NR, NRC(=O), C(=O)O, OC(=O), OC(=O)NR, C(=S)NR, NRC(=S), OC(=S)NR, NRC(=S)O, or NRC(=S)NR', wherein R and R' are independently H, alkyl, heteroalkyl, aryl or heteroaryl; and $R_9$ is hydrogen, OR", SR", NR"R''', alkyl, aryl, or heteroaryl, wherein R" and R''' are independently H, alkyl, aryl or heteroaryl.

11. A compound of the structure 1b:

<chemical structure 1b: benzene ring with R$_1$, R$_2$, R$_4$ substituents connected to N of oxazolidinone with CH$_2$NH—R$_6$> wherein:

$R_2$ and $R_4$ are, independently, hydrogen, alkyl, heteroalkyl, heteroaryl or an electron withdrawing group;

$R_6$ is thioacyl, aminothiocarbonyl, alkoxythiocarbonyl, or alkylthio(thiocarbonyl); and $R_1$ is:

C(O)NR$_7$R$_8$, C(S)NR$_7$R$_8$, OC(O)NR$_7$R$_8$, OC(S)NR$_7$R$_8$, NR$_7$C(O)NR$_7$R$_8$, NR$_7$C(S)NR$_7$R$_8$, C(O)OR$_7$, C(O)R$_7$, S(O)$_2$R$_7$, or S(O)R$_7$, wherein R$_7$ and R$_8$ are, independently, $C_{5-12}$alkyl, heteroalkyl, aryl or heteroaryl;

SR$_{12}$, wherein R$_{12}$ is hydrogen, alkyl, heteroalkyl, aryl or heteroaryl;

NR$_{13}$R$_{14}$ or CH$_2$NR$_{13}$R$_{14}$, wherein R$_{13}$ is hydrogen, acyl, methylsulfonyl, alkyl, heteroalkyl, aryl or heteroaryl, and R$_{14}$ is acyl, methylsulfonyl, $C_{5-12}$alkyl, heteroalkyl, aryl or heteroaryl;

NR$_{30}$C(O)R$_{31}$ or NR$_{30}$(SO$_2$)R$_{31}$, wherein R$_{30}$ is hydrogen, alkyl, heteroalkyl, aryl, or heteroaryl, and R$_{31}$ is hydrogen, $C_{5-12}$alkyl, heteroalkyl, aryl, or heteroaryl;

2-oxazolyl comprising R$_{15}$ at the 4-position and R$_{16}$ at the 5-position of the oxazolyl, wherein R$_{15}$ and R$_{16}$ are, independently, hydrogen, alkyl, heteroalkyl, aryl, heteroaryl or an electron withdrawing group;

2-aminothiazolyl comprising R$_{17}$ at the 4-position and R$_{18}$ at the 5-position of the thiazole, wherein R$_{17}$ and R$_{18}$, are, independently, hydrogen, alkyl, heteroalkyl, aryl, heteroaryl or an electron withdrawing group; and 2-(1,3,4-thiadiazolyl) comprising R$_{21}$ at the 5-position of the 1,3,4-thiadiazole, wherein R$_{21}$ is hydrogen, alkyl, heteroalkyl, amino($C_{1-4}$ alkyl), acylamino ($C_{1-4}$ alkyl), thioacylamino($C_{1-4}$ alkyl), sulfonamido ($C_{1-4}$ alkyl), heterocarbonylamino($C_{1-4}$ alkyl), aryl, heteroaryl, an electron withdrawing group, or NR$_{22}$R$_{23}$, wherein R$_{22}$ and R$_{23}$ are, independently, acyl, thioacyl, methylsulfonyl, heteroalkyl, aryl or heteroaryl;

CH=CHR$_{24}$ or C≡CR$_{24}$, wherein R$_{24}$ is C(O)NR$_7$R$_8$, C(S)NR$_7$R$_8$, OC(O)NR$_7$R$_8$, OC(S)NR$_7$R$_8$, NR$_7$C(O) NR$_7$R$_8$, NR$_7$C(S)NR$_7$R$_8$, C(O)OR$_{10}$, C(O)R$_{11}$, SR$_{12}$, S(O)$_2$R$_{12}$, S(O)R$_{12}$, NR$_{13}$R$_{14}$, CH$_2$NR$_{13}$R$_{14}$, alkyl, aryl, or heteroaryl; or 5,6-dihydro-1,4,2-dioxazine-3-yl, wherein R$_{25}$ is at the 5-position of dioxazine, and R$_{26}$ is at the 6-position of dioxazine, and wherein R$_{25}$ and R$_{26}$, are, independently, hydrogen, alkyl, heteroalkyl, aryl, heteroaryl or an electron withdrawing group;

wherein optionally R$_1$ and R$_2$ together are a quinolone heterocycle C(=O)C(COOH)=CHNR$_{27}$, or R$_1$ and R$_2$ together are a benzotriazole heterocycle NNNR$_{27}$ or NN(R$_{27}$)N, wherein R$_{27}$ is alkyl, aryl, or heteroaryl, with the proviso that when R$_1$ is 2-(1,3,4-thiadiazolyl) and R$_{21}$ is hydrogen, alkyl, heteroalkyl, amino($C_{1-4}$ alkyl), acylamino($C_{1-4}$ alkyl), sulfonamido($C_{1-4}$ alkyl), an electron withdrawing group, or NR$_{22}$R$_{23}$, then R$_2$ and R$_4$ are different from hydrogen or an electron withdrawing group.

12. A compound of claim 11, wherein R$_1$ is C(O)NR$_7$R$_8$, C(S)NR$_7$R$_8$, C(O)OR$_7$, C(O)R$_7$, SR$_{12}$, S(O)$_2$R$_7$, S(O)R$_7$, or NR$_{13}$R$_{14}$.

13. A compound according to claim 11, wherein R$_1$ is C(O)NR$_7$R$_8$.

14. A compound according to claim 11, wherein R$_1$ is C(O)OR$_7$.

15. A compound according to claim 11, wherein R$_1$ is C(O)R$_7$.

16. A compound according to claim 11, wherein R$_1$ is SR$_{12}$.

17. A compound according to claim 11, wherein R$_1$ is NR$_{13}$R$_{14}$.

18. A compound according to claim 11, wherein R$_1$ is 2-oxazolyl, wherein R$_{15}$ is at the 4-position and R$_{16}$ is at the 5-position of the oxazole group.

19. A compound according to claim 11, wherein R$_1$ is 2-aminothiazolyl, wherein R$_{17}$ is at the 4-position and R$_{18}$ is at the 5-position of the aminothiazolyl group.

20. A compound according to claim 11, wherein R$_1$ is CH$_2$NR$_{13}$R$_{14}$.

21. A compound according to claim 12, wherein $R_4$ is hydrogen.

22. A compound according to claim 21, wherein $R_2$ is fluorine.

23. A compound according to claim 22, wherein, $R_6$ is $C(S)C_{1-7}$ alkyl or $C(S)C_{3-6}$ cycloalkyl.

24. A compound according to claim 23, wherein $R_1$ is $C(O)NR_7R_8$.

25. A compound according to claim 24, wherein $R_8$ is heteroaryl.

26. A compound according to claim 13, wherein $R_4$ is hydrogen.

27. A compound according to claim 26, wherein $R_2$ is fluorine.

28. A compound according to claim 27, wherein $R_6$ is $C(S)CH_3$, and $NR_7R_8$ is NH(5'-(5-aminopyridine-2-yl)thiopyridine-3'-yl) or NH(pyridine-3-yl) or NH(5-chloropyridine-3-yl).

29. A compound selected from the group consisting of:

[chemical structures]

30. A compound of formula 3c:

[structure 3c]

wherein:

$R_2$ and $R_4$ are, independently, hydrogen, alkyl, heteroalkyl, heteroaryl or an electron withdrawing group;

$R_6$ is thioacyl, aminothiocarbonyl, alkoxythiocarbonyl, or alkylthio(thiocarbonyl);

$R_8$ is $C_4$–$C_7$ alkyl, $C_2$–$C_7$ alkynyl, O, C(=S)NR, NRC(=S), C(=S)O, OC(=O), OC(=S), NRCONR', NRCSNR', or $(CH_2)_nO$, wherein n=2–6, and wherein R and R' are independently H, alkyl, heteroalkyl, aryl or heteroaryl; and $R_9$ is hydrogen, OH, OR", SR", NR"R'", alkyl, aryl, heteroalkyl, or heteroaryl, and wherein R" and R'" are independently H, alkyl, heteroalkyl, aryl or heteroaryl.

31. The compound of claim 30, wherein:

$R_6$ is $C(S)C_{1-7}$ alkyl or $C(S)C_{3-6}$ cycloalkyl;

$R_8$ is OC(=O); and $R_9$ is alkyl.

32. A compound selected from the group consisting of

[chemical structure]

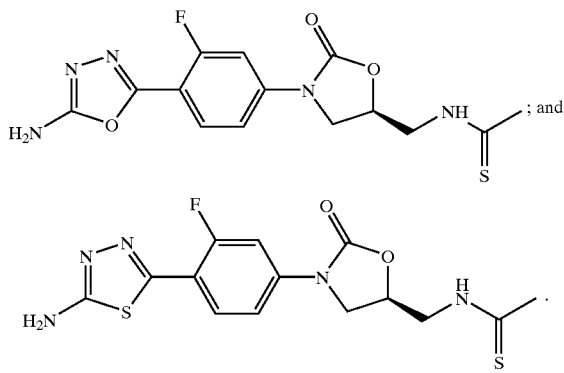

33. The compound of claim 30 selected from the group consisting of

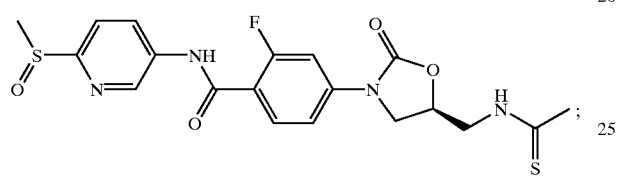

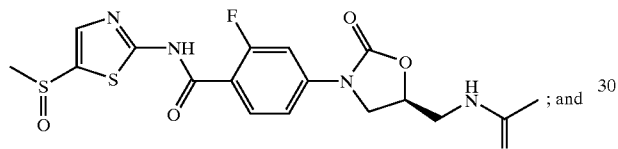

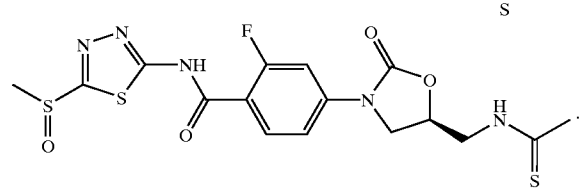

34. A compound selected from the group consisting of

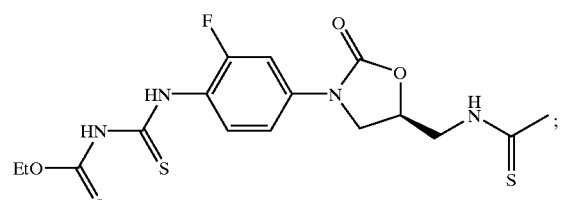

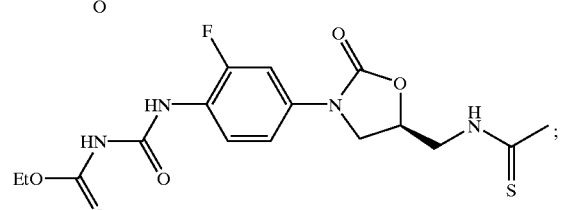

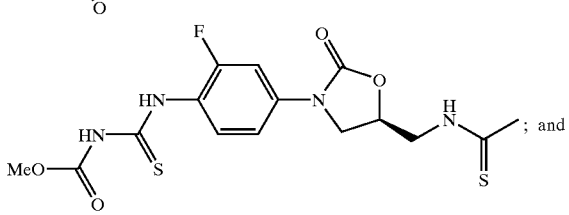

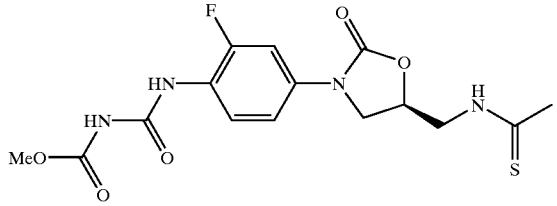

35. A compound of formula 5c:

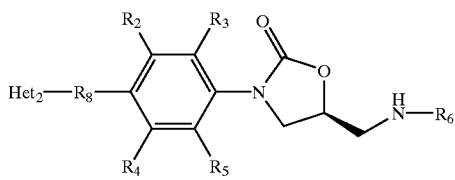

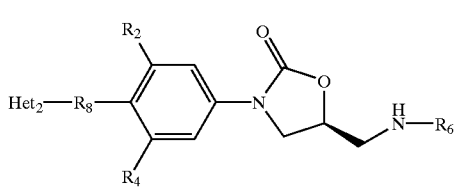

wherein:

$R_2$ and $R_4$ are, independently, hydrogen, alkyl, heteroalkyl, heteroaryl or an electron withdrawing group;

$R_6$ is thioacyl, aminocarbonyl, alkoxycarbonyl, aminothiocarbonyl, alkoxythiocarbonyl, alkylthio(carbonyl), or alkylthio(thiocarbonyl);

$R_8$ is $C_1$–$C_7$ alkyl, $C_1$–$C_7$ alkenyl, $C_1$–$C_7$ alkynyl, NR, O, S, C(=O)NR, C(=S)NR, NRC(=O), NRC(=S), C(=O), C(=O)O, C(=S)O, OC(=O), OC(=S), S(=O), $SO_2$, $SO_2$NR, $NRSO_2$, NRCONR', NRCSNR', or $(CH_2)_nO$, wherein n=0–6, and wherein R and R' are independently H, alkyl, heteroalkyl, aryl or heteroaryl; and $Het_2$ is a heterocyclic group.

36. The compound of claim 35, wherein
$R_6$ is $C(S)C_{1-7}$ alkyl or $C(S)C_{3-6}$ cycloalkyl;
$R_8$ is S; and
$Het_2$ is a thienylphenyl or thiazolyl group.

37. The compound of claim 35, wherein:
$R_6$ is $C(S)C_{1-7}$ alkyl or $C(S)C_{3-6}$ cycloalkyl;
$R_8$ is NH; and
$Het_2$ is 1,3,5-triazinyl.

38. The compound of claim 35 having the structure:

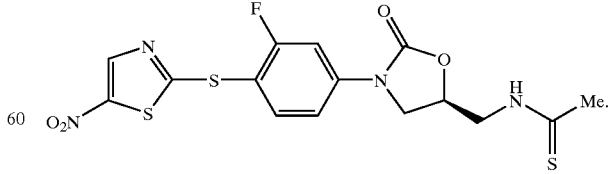

39. A composition for the treatment or prevention of an infectious disorder comprising an effective amount of a compound of claim 1 and a pharmaceutically acceptable carrier.

40. The composition of claim 39 wherein the compound is selected from the group consisting of:

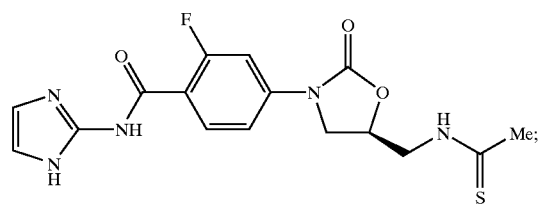

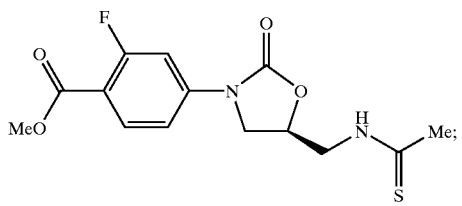

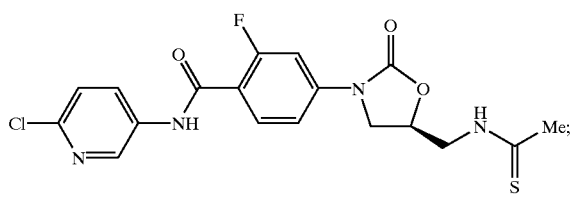

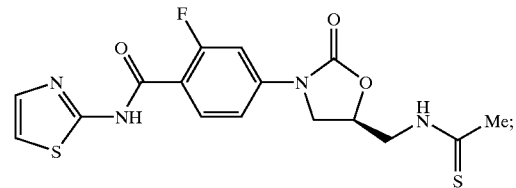

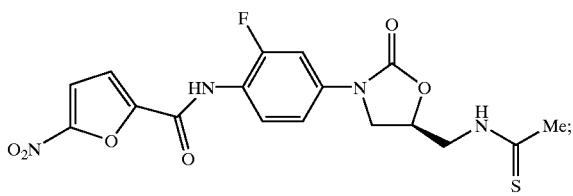

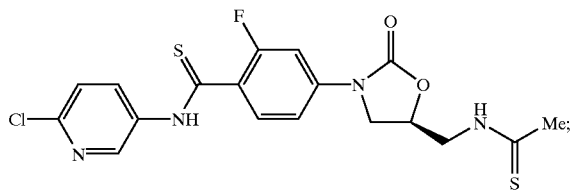

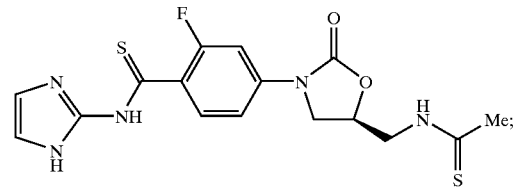

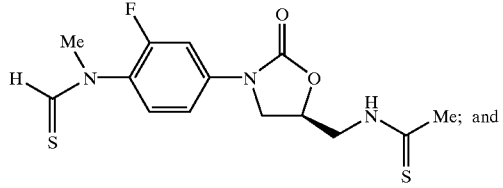

-continued

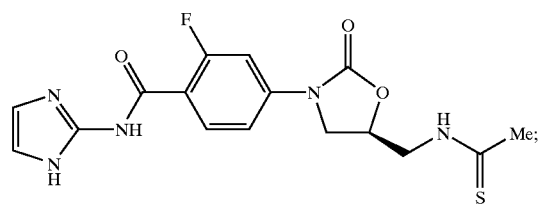

41. A composition for the treatment or prevention of an infectious disorder comprising an effective amount of a compound of claim 5 and a pharmaceutically acceptable carrier.

42. A composition for the treatment or prevention of an infectious disorder comprising an effective amount of a compound of claim 7 and a pharmaceutically acceptable carrier.

43. A composition for the treatment or prevention of an infectious disorder comprising an effective amount of a compound of claim 9 and a pharmaceutically acceptable carrier.

44. A composition for the treatment or prevention of an infectious disorder comprising an effective amount of a compound of claim 11 and a pharmaceutically acceptable carrier.

45. A composition for the treatment or prevention of an infectious disorder comprising an effective amount of a compound of claim 30 and a pharmaceutically acceptable carrier.

46. A method of treating or preventing an infectious disorder in a human or other animal subject, comprising administering to the subject an effective amount of a compound of claim 1.

47. A method of treating or preventing an infectious disorder in a human or other animal subject, comprising administering to the subject an effective amount of a compound of claim 5.

48. A method of treating or preventing an infectious disorder in a human or other animal subject, comprising administering to the subject an effective amount of a compound of claim 7.

49. A method of treating or preventing an infectious disorder in a human or other animal subject, comprising administering to the subject an effective amount of a compound of claim 9.

50. A method of treating or preventing an infectious disorder in a human or other animal subject, comprising administering to the subject an effective amount of a compound of claim 11.

51. A method of treating or preventing an infectious disorder in a human or other animal subject, comprising administering to the subject an effective amount of a compound of claim 30.

52. A method for a solid phase synthesis of the compounds of claim 5 comprising the treatment of an amide precursor comprising a group $NC(O)R_{10}$, immobilized on a support, wherein $R_{10}$ is alkyl, heteroalkyl, aryl or heteroaryl, with a thionation reagent; and release of a compound of formula 3 from the support.

53. A compound of formula 1:

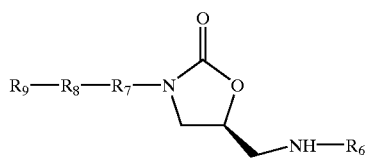

wherein:

$R_6$ is thioacyl, aminothiocarbonyl, alkoxythiocarbonyl, alkylthio(carbonyl), or alkylthio(thiocarbonyl);

$R_7$ is monocyclic heteroaryl;

$R_8$ is $C_4$–$C_7$ alkyl, $C_2$–$C_7$ alkynyl, O, OC(=O), OC(=O)NR, NRC(=O)O, C(=S)NR, NRC(=S), C(=S), C(=S)O, OC(=S), OC(=S)NR, NRC(=S)O, NRCONR', NRC(=S)NR', or $(CH_2)_nO$, wherein n=2–6, and wherein R and R' are independently H, alkyl, heteroalkyl, aryl or heteroaryl; and $R_9$ is hydrogen, OH, OR", SR", NR"R'", alkyl, aryl, heteroalkyl, or heteroaryl, and wherein R" and R'" are independently H, alkyl, heteroalkyl, aryl or heteroaryl.

54. The compound of claim 53 wherein:

$R_8$ is OC(=O), OC(=O)NR, C(=S)NR, NRC(=S), OC(=S)NR, NRC(=S)O, or NRC(=S)NR', wherein R and R' are independently H, alkyl, heteroalkyl, aryl or heteroaryl; and $R_9$ is hydrogen, OR", SR", NR"R'", alkyl, aryl, or heteroaryl, wherein each R" and R'" are independently H, alkyl, aryl or heteroaryl.

55. A composition for the treatment or prevention of an infectious disorder comprising an effective amount of a compound of claim 53 and a pharmaceutically acceptable carrier.

56. A composition for the treatment or prevention of an infectious disorder comprising an effective amount of a compound of claim 7 a pharmaceutically acceptable carrier.

57. A composition for the treatment or prevention of an infectious disorder comprising an effective amount of a compound of claim 35 and a pharmaceutically acceptable carrier.

58. A method of treating or preventing an infectious disorder in a human or other animal subject, comprising administering to the subject an effective amount of a compound of claim 53.

59. A method of treating or preventing an infectious disorder in a human or other animal subject, comprising administering to the subject an effective amount of a compound of claim 7.

60. A method of treating or preventing an infectious disorder in a human or other animal subject, comprising administering to the subject an effective amount of a compound of claim 35.

* * * * *

UNITED STATES PATENT AND TRADEMARK OFFICE
CERTIFICATE OF CORRECTION

PATENT NO. : 6,441,005 B1
DATED : August 27, 2002
INVENTOR(S) : Gordeev et al.

It is certified that error appears in the above-identified patent and that said Letters Patent is hereby corrected as shown below:

Column 80,
Line 15, please delete "$C_2$-$C_7$ allynyl," and insert -- $C_2$-$C_7$ alkynyl, -- in its place.
Line 27, please delete "$R_{10}$ (is heteroalkyl" and insert -- $R_{10}$ is heteroalkyl -- in its place.
Line 36, please delete "wherein R´ and R˝ are" and insert -- wherein R˝ and R‴ are -- in its place.
Line 62, please delete "H, allyl, heteroalkyl" and insert -- H, alkyl, heteroalkyl -- in its place.

Column 81,
Line 19, please delete "wherein." and insert -- wherein: -- in its place.
Line 21, please delete "$R_8$ is $C_2$-$C_7$ alkyl," and insert -- $R_8$ is $C_1$-$C_7$ alkyl, -- in its place.

Signed and Sealed this

Fourth Day of May, 2004

JON W. DUDAS
*Acting Director of the United States Patent and Trademark Office*